(12) United States Patent
Pendergast et al.

(10) Patent No.: US 11,883,401 B2
(45) Date of Patent: Jan. 30, 2024

(54) COMPOSITIONS FOR THE TREATMENT OF PATHOGENIC- AND/OR CHEMICAL-INDUCED LUNG INJURY AND FOR THE TREATMENT OF CANCER AND METHODS OF USING SAME

(71) Applicant: Duke University, Durham, NC (US)

(72) Inventors: Ann Marie Pendergast, Durham, NC (US); Aaditya Khatri, Durham, NC (US)

(73) Assignee: Duke University, Durham, NC (US)

( * ) Notice: Subject to any disclaimer, the term of this patent is extended or adjusted under 35 U.S.C. 154(b) by 1014 days.

(21) Appl. No.: 16/737,855

(22) Filed: Jan. 8, 2020

(65) Prior Publication Data

US 2020/0215066 A1 Jul. 9, 2020

Related U.S. Application Data

(60) Provisional application No. 62/789,809, filed on Jan. 8, 2019.

(51) Int. Cl.
| | | |
|---|---|---|
| *A61K 31/433* | (2006.01) | |
| *A61K 31/506* | (2006.01) | |
| *A61K 31/337* | (2006.01) | |
| *A61K 31/475* | (2006.01) | |
| *A61P 11/00* | (2006.01) | |
| *A61K 33/243* | (2019.01) | |

(52) U.S. Cl.
CPC .......... *A61K 31/506* (2013.01); *A61K 31/337* (2013.01); *A61K 33/243* (2019.01); *A61P 11/00* (2018.01)

(58) Field of Classification Search
CPC .. A61K 31/506; A61K 31/337; A61K 31/433; A61K 31/475
USPC .................................................. 514/275, 363
See application file for complete search history.

(56) References Cited

U.S. PATENT DOCUMENTS

| | | | |
|---|---|---|---|
| 5,843,509 | A | 12/1998 | Calvo et al. |
| 6,649,192 | B2 | 11/2003 | Alonso et al. |

FOREIGN PATENT DOCUMENTS

| | | |
|---|---|---|
| WO | WO9119813 | 12/1991 |
| WO | WO9932619 | 7/1999 |
| WO | WO0129058 | 4/2001 |

OTHER PUBLICATIONS

Abbas-Terki, et al., "Lentiviral-mediated RNA interference," Hum Gene Ther. 13:2197-201 (2002).
Barton and Medzhitov, "Retroviral delivery of small interfering RNA into primary cells," Proc Natl Acad Sci USA. 99: 14943-5 (2002).
Bernstein, et al., "Role for a bidentate ribonuclease in the initiation step of RNA interference," Nature 409, 363-366 (2001).
Borkhardt, A., "Blocking oncogenes in malignant cells by RNA interference—new hope for a highly specific cancer treatment?" Cancer Cell. 2: 167-8 (2002).
Cancer Genome Atlas Research N., "Comprehensive molecular profiling of lung adenocarcinoma," Nature, 511 (7511):543-50 (2014).
Castanotto D, Rossi JJ., "The promises and pitfalls of RNA-interference-based therapeutics," Nature, 457(7228):426-433 (2009).
Czauderna et al., "Structural variations and stabilizing modifications of synthetic siRNAs in mammalian cells," Nucleic Acids Res. 31:2705-2716 (2003).
Devroe and Silver, "Retrovirus-delivered siRNA," BMC Biotechnol. 2:15 (2002).
Dzau et al., "Gene therapy for cardiovascular disease," Trends in Biotechnology 11, 205-210 (2003).
Elbashir et al., "RNA interference is mediated by 21- and 22-nucleotide RNAs," Genes Dev. 15, 188-200 (2001).
Elbashir SM, et al., "Duplexes of 21-nucleotide RNAs mediate RNA interference in cultured mammalian cells," Nature 411: 494-498 (2001).
Fire A, et al., "Potent and specific genetic interference by double-stranded RNA in Caenorhabditis elegans," Nature 391:806-811 (1998).
Fire, "RNA-triggered gene silencing," Trends Genet. 15, 358-363 (1999).
Fulcher ML & Randell SH, "Human nasal and tracheo-bronchial respiratory epithelial cell culture," Methods Mol Biol 945: 109-121 (2013).
Gomez JC, et al., "Nrf2 Modulates Host Defense during *Streptococcus pneumoniae* Pneumonia in Mice," Journal of Immunology 197(7):2864-2879 (2016).
Hamilton, A et al., "A species of small antisense RNA in post-transcriptional gene silencing in plants," Science 286, 950-952 (1999).
Hammond, S. M., et al., "An RNA-directed nuclease mediates post-transcriptional gene silencing in *Drosophila* cells," Nature 404, 293-296 (2000).
Hammond, S. M., et al., "Post-transcriptional gene silencing by double-stranded RNA," Nature Rev. Genet. 2, 110-9 (2001).
Hannon, G. J., "RNA interference," Nature. 418:244-51 (2002).
Heiman M, et al., "Cell type-specific mRNA purification by translating ribosome affinity purification (TRAP)," Nature protocols 9(6):1282-1291 (2014).

(Continued)

*Primary Examiner* — Raymond J Henley, III
(74) *Attorney, Agent, or Firm* — Polsinelli PC

(57) ABSTRACT

The present disclosure provides compositions and methods for the treatment of pathogen-induced and/or chemical-induced lung injury, for regenerating lung epithelial cells following lung injury, for treating cancer, and for sensitizing a subject suffering from cancer to a chemotherapeutic agent.

10 Claims, 88 Drawing Sheets

Specification includes a Sequence Listing.

(56) References Cited

OTHER PUBLICATIONS

Hogan BL, et al., "Repair and regeneration of the respiratory system: complexity, plasticity, and mechanisms of lung stem cell function," Cell stem cell 15(2):123-138 (2014).
John et al., "Human MicroRNA targets," PLOS Biology, 11(2), 1862-1879 (2004).
Kim et al., "Identification of bronchioalveolar stem cells in normal lung and lung cancer," Cell 121(6):823-835 (2005).
Kumar, et al., "Distal airway stem cells yield alveoli in vitro and during lung regeneration following H1N1 influenza infection," Cell. 147(3):525-38 (2011).
Lewis, et al., "Efficient delivery of siRNA for inhibition of gene expression in postnatal mice," Nat Genet. 32:107-8 (2002).
Lori, et al., "Gene therapy approaches to HIV infection," Am J Pharmacogenomics. 2:245-52 (2002).
Matta, et al., "Use of lentiviral vectors for delivery of small interfering RNA," Cancer Biol Ther. 2:206-10 (2003).
McManus and Sharp, "Gene silencing in mammals by small interfering RNAs," Nat Rev Genet. 3:737-47 (2002).
Moresco EM, et al., "Integrin-mediated dendrite branch maintenance requires Abelson (Abl) family kinases," J Neurosci 25(26):6105-6118 (2005).
Morris, et al., "Translocating peptides and proteins and their use for gene delivery," Curr Opin Biotechnol. 11:461-6 (2000).
Myers et al., "Recombinant Dicer efficiently converts large dsRNAs into siRNAs suitable for gene silencing," Nature Biotechnology 21:324-328 (2003).
Paul, et al., "Effective expression of small interfering RNA in human cells," Nat Biotechnol. 20:505-8 (2002).
Rawlins EL, et al., "The role of Scgb1a1+ Clara cells in the long-term maintenance and repair of lung airway, but not alveolar, epithelium," Cell Stem Cell 4(6):525-534 (2009).
Qin, et al., "Inhibiting HIV-1 infection in human T cells by lentiviral-mediated delivery of small interfering RNA against CCR5," Proc Natl Acad Sci USA 100:183-8 (2003).
Scherr, et al., "Gene silencing mediated by small interfering RNAs in mammalian cells," Curr Med Chem 10:245-56 (2003).
Scherr, et al., "Modulation of gene expression by lentiviral-mediated delivery of small interfering RNA," Cell Cycle. 2:251-7 (2003).
Sharp, "RNA interference," Genes Dev. 15, 485-490 (2001).
Shen, et al., "Gene silencing by adenovirus-delivered siRNA," FEBS Lett, 539(1-3)111-4 (2003).
Shin et al., "Optimization of linear double-stranded RNA for the production of multiple siRNAs targeting hepatitis C virus," RNA, 15(5): 898-910 (2009).
Shinagawa et al., "Generation of Ski-knockdown mice by expressing a long double-strand RNA from an RNA polymerase II promoter," Genes and Dev., 17, 1340-5 (2003).
Shuey, et al., "RNAi: gene-silencing in therapeutic intervention," Drug Discov Today. 7: 1040-6 (2002).
Simeoni, et al., "Insight into the mechanism of the peptide-based gene delivery system MPG: implications for delivery of siRNA into mammalian cells," Nucleic Acids Res. 31 :2717-24 (2003).
Song, et al., "RNA interference targeting Fas protects mice from fulminant hepatitis," Nat Med. 9:347-51 (2003).
Sorensen, et al., "Gene silencing by systemic delivery of synthetic siRNAs in adult mice," J Mol Biol. 327:761-6 (2003).
Suliman HB et al., "Mitochondrial quality control in alveolar epithelial cells damaged by S. aureus pneumonia in mice," American journal of Physiology Lung Cellular and Molecular Physiology 313(4):L699-L709 (2017).
Tadokoro T, et al., "IL-6/STAT3 promotes regeneration of airway ciliated cells from basal stem cells," Proceedings of the National Academy of Sciences of the US.A., 111 (35):E3641-9 (2014).
Tuerk et al., "Systematic evolution of ligands by exponential enrichment: RNA ligands to bacteriophage T4 DNA polymerase," Science; 249(4968):505-10 (1990).
Tuschl, T., "RNA interference and small interfering RNAs," Chem Biochem. 2, 239-245 (2001).
Wang et al., "Delivery of siRNA therapeutics: barriers and carriers," AAPS J.; 12(4): 492-503 (2010).
Gao X, et al., "GRHL2 coordinates regeneration of a polarized mucociliary epithelium from basal stem cells," J Cell Biol (2015) 211:669-682.
Xu X, et al., "Evidence for type II cells as cells of origin of K-Ras-induced distal lung adenocarcinoma," Proc Natl Acad Sci USA 109(13):4910-4915 (2012).
Zamore, P. D., et al., "RNAi: double-stranded RNA directs the ATP-dependent cleavage of mRNA at 21 to 23 nucleotide intervals," Cell 101, 25-33 (2000).
Zhang J, et al., "Targeting Bcr-Abl by combining allosteric with ATP-binding-site inhibitors," Nature 463(7280):501-506 (2010).
Zuo W, et al., "p63(+)Krt5(+) distal airway stem cells are essential for lung regeneration," Nature. 517(7536):616-20 (2015).
Elbashir SM, et al. (2001) Functional anatomy of siRNAs for mediating efficient RNAi in *Drosophila melanogaster* embryo lysate. EMBO J. 20(23):6877-88.
Kwon et al., "Mouse models for lung cancer," Molecular Oncology 7 (2013):165-177.
Khatri et al., "ABL kinase inhibition sensitizes primary lung adenocarcinomas to chemotherapy by promoting tumor cell differentiation," Oncotarget (2019); 10(20):1874-1886.

Timeline for primary HBEC experiments

Seed 3 X $10^5$ cells — Day 0
Switch to air-liquid interface culture — Day 3
Exposure to 1 X $10^8$ cfu *S. aureus* — Day 28
Harvest cells — Day 29-33

FIG. 1A

**Timeline for *Abl1* knockdown experiment**

Tamoxifen 200mg/kg 4 times — 1 week | Nasal *S. aureus* 5 X 10⁶ CFU — 2 weeks | 3 Days | Sac

FIG. 2A

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ggctgtgagt accttgctgc                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
ggcgctcatc ttcattcagg c                                            21

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
```
agtttagcac cagggttcat cag    23

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
cttcctatcc ctggtgaagc at    22

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
aggtcggtgt gaacggattt g    21

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
tgtagaccat gtagttgagg tca    23

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
aacgccttct catcgtggt    19

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
tagatatagt agagtggtag ct    22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
cccggatgca ctcttctcta tg    22

<210> SEQ ID NO 10
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 10
tcggattctg ccttcaggaa                                                    20

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
tggagcatat ttgaccatct ca                                                 22

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
caaaggcctg aaggtggata                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ctgtcccaag gaatccagag                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ccgtctgagt agcggaagtc                                                    20
```

COMPOSITIONS FOR THE TREATMENT OF PATHOGENIC- AND/OR CHEMICAL-INDUCED LUNG INJURY AND FOR THE TREATMENT OF CANCER AND METHODS OF USING SAME

CROSS-REFERENCE TO RELATED APPLICATIONS

This application claims priority to U.S. Provisional Patent Application No. 62/789,809, filed Jan. 8, 2019, the disclosure of which is hereby incorporated by reference in its entirety.

INCORPORATION BY REFERENCE OF SEQUENCE LISTING PROVIDED ELECTRONICALLY

This application contains a Sequence Listing submitted as an electronic .txt file named "19-2447-US_Seq_Listing", having a size of 3.1 KB and created on Jan. 8, 2020. The information contained in this electronic .txt file is incorporated herein by reference in its entirety.

FEDERAL FUNDING LEGEND

This invention was made with Government support under Federal Grant No. 5R01 HL151782 awarded by the National Institutes of Health. The Federal Government has certain rights to this invention.

BACKGROUND

Field of the Invention

The present disclosure provides compositions and methods for the treatment of pathogen-induced and/or chemical-induced lung injury, for regenerating lung epithelial cells following lung injury, for treating cancer, and for sensitizing a subject suffering from cancer to a chemotherapeutic agent.

Description of Related Art

Damage to the lung epithelium in response to pathogens and chemical exposure are major health problems worldwide. In particular, arenchymal lung infections disrupt lung epithelial architecture and function by eliciting destruction of airway and alveolar cell populations.

Approximately 50,000 cases of lung infection by *Staphylococcus aureus* (*S. aureus*) occur per year in the United States. *S. aureus* pneumonia has high morbidity and mortality rates, as it frequently presents in the context of hospital-acquired pneumonia and patients frequently progress to sepsis and multi-organ system failure. Treatment is limited to antibiotics and supportive care. Currently there are no approved drugs that directly prevent or repair epithelial cell damage following pathogen-induced lung injury. Current therapeutic interventions for the treatment of respiratory infections are hampered by the evolution of multidrug resistance in pathogens as well as the lack of effective cellular targets. Despite the identification of multiple region-specific lung progenitor cells, the identity of molecules that might be therapeutically targeted in response to infections to promote activation of progenitor cell types remains elusive. Therapeutic strategies to protect or promote lung epithelial cell regeneration following injury could profoundly improve patient outcomes when used in combination with antibiotics and supportive care, particularly in the context of infections caused by resistant bacterial strains.

Furthermore, civilians in war-zones are sometimes exposed to chemical agents such as chlorine gas while soldiers are frequently exposed to noxious substances such as mineralized dust or chemicals (i.e. sulfur dioxide) released from burn pits. Chlorine gas induces significant injury to all epithelial cell layers of the human and mouse airway.

Lung epithelial cells are the first line of defense against foreign agents such as pathogens and chemicals. The lung epithelium is comprised of airway and alveolar cells. In the airway epithelium, studies have identified both basal and secretory cells as critical cell types for regeneration during normal cell turnover and following injury. In the alveoli, Type II alveolar epithelial cells (AECs) give rise to Type I AECs during regeneration following injury. Other reports have implicated a small subpopulation of cells at the bronchioalveolar duct junction (BADJ) expressing markers of both secretory cells (SCGB1A1+) from the airway and Type II AECs (SPC+, expressed by Sftpc) as progenitor cells for epithelial cells in both the distal airway and alveoli. However, at baseline, the contribution of this putative "bronchioalveolar stem cell" (BASC) population is small with on average <1 cell per BADJ (Hogan B L. et al. (2014) *Cell stem cell* 15(2): 123-138).

Additionally, with an estimated 234,000 new cases and 154,000 deaths in 2018, lung cancer is the leading cause of cancer deaths in the United States, accounting for one-quarter of all cancer deaths. Approximately, 80% of deaths are associated with smoking, which confers a 25-fold increase in relative risk. Smoking-associated lung cancer has one of the highest mutational burdens of all cancers. Despite advancements in molecularly targeted therapies for patients harboring actionable genetic abnormalities such as mutations in EGFR, ALK, RET, or BRAF, the majority of lung cancers lack identifiable driver oncogenes or harbor mutations in KRAS, TP53, or other clinically inactionable genetic abnormalities.

The $KRAS^{LSL-G12D}$; $p53^{fl/fl}$ mouse model was developed as a powerful model for studying lung adenocarcinomas (Jackson E L, et al. (2001) Genes Dev. 15(24):3243-8; DuPage M, et al. (2009) Nature protocols. 4(7):1064-72). Tumor protein p53 (TP53 or p53) (46%) and Kirsten rat sarcoma viral oncogene homolog (KRAS) (33%) are the most commonly mutated genes in human lung adenocarcinomas (Cancer Genome Atlas Research N. (2014) Nature. 511(7511):543-50). Because neither genetic alteration is clinically actionable, chemotherapy remains the mainstay of treatment in patients with oncogenic KRAS driver mutations. However, chemoresistance to genotoxic agents such as docetaxel and cisplatin remains the most important clinical problem facing lung cancer patients.

Thus, there is a need for novel treatment and strategies to treat and/or prevent epithelial cell damage following pathogen-induced and chemical-induced lung injury, as well as a need for improved treatments for lung cancer. The work described herein identifies new Abl-regulated pathways in (1) lung regeneration following bacterial and viral infections, (2) airway epithelium regeneration following chemical injury, and (3) lung cancer cell sensitization to chemotherapy.

Targeting pathways such as the Abl pathway that promote expansion progenitor cells after lung injury can ameliorate the morbidity and mortality associated with pathogen-induced infections that cause lung damage and chemical-induced lung injury. Targeting the same pathways can also enhance response rates to chemotherapy in patients with lung adenocarcinomas.

BRIEF SUMMARY OF THE DISCLOSURE

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, the present invention provides a method of treating lung injury in a subject in need thereof, comprising administering to the subject a therapeutically effective amount of an Abelson ("Abl") kinase inhibitor. In certain embodiments of the first aspect of the invention, the lung injury is a pathogen- or chemical-induced lung injury.

In a second aspect, the present invention provides a method of regenerating lung epithelial cells following lung injury in a subject, comprising administering to the subject a therapeutically effective amount of Abl kinase inhibitor. In certain embodiments of the second aspect of the invention, the lung injury is a pathogen- or chemical-induced lung injury.

In a third aspect, the present invention provides a method of treating cancer in a subject in need thereof, comprising administering to the subject a therapeutically effective amount of an Abl kinase inhibitor in combination with a chemotherapeutic agent. In certain embodiments of the third aspect of the invention, the cancer is lung cancer.

In a fourth aspect, the present invention provides a method of sensitizing a subject suffering from cancer to a chemotherapeutic agent comprising administering to the subject a therapeutically effective amount of an Abl kinase inhibitor. In certain embodiments of the fourth aspect of the invention, the cancer is lung cancer.

In a fifth aspect, the present invention provides a composition comprising an Abl inhibitor and a pharmaceutically acceptable carrier or excipient.

Additional features and advantages are described herein, and will be apparent from the following detailed description, drawings, and the claims.

BRIEF DESCRIPTION OF THE DRAWINGS

The foregoing aspects and other features of the disclosure are explained in the following description, taken in connection with the accompanying drawings, wherein:

FIGS. 1A-1E show that Abl kinases are upregulated in primary human lung bronchial epithelial cells (HBECs) and GFP-labeled cells from CC10 (Scgb1a1)-CreERT; Rosa26-fGFP; Abl1 WT mice following exposure to $S.$ $aureus$. FIG. 1A is a timeline of air-liquid interface cultures: Primary HBECs are seeded on polyester inserts in a transwell chamber. Media from the top chamber is removed once the cells are confluent to promote differentiation of basal cells to luminal cells. Cells are exposed to $S.$ $aureus$ at day 28 once they have fully differentiated into a pseudostratified layer of ciliated, secretory, and basal cells and are then harvested one, two, and five days after injury. FIG. 1B is a graph showing mRNA expression of ABL kinases, predominantly ABL1, increases by 20 to 30-fold following exposure to $S.$ $aureus$. n=3 patients, each run in triplicate. FIG. 1C is a gel of immunoblotting with ABL1 and ABL2 specific antibodies shows an increase in ABL1 and ABL2 protein expression 24 hours after exposure to $S.$ $aureus$. FIG. 1D is a timeline of mouse experiment: Two weeks prior to nasal insufflation of $5 \times 10^8$ CFU $S.$ $aureus$, mice were treated with tamoxifen to induce excision of $Abl1^{fl/fl}$ in CC10 (Scgb1a1)-CreERT mice. FIG. 1E is a graph showing analysis of isolated GFP-labeled cells from mice showed that Abl1 mRNA expression increases by >10-fold in GFP-labeled cells 72 hours after exposure to $S.$ $aureus$ and is decreased in $Abl1^{fl/fl}$ mice compared to wild-type control mice (n=4-8 animals per group; each sample run in triplicate). Graphs represent means with S.E.M.

FIGS. 2A-2G show inactivation of Abl1 in Scgb1a1+ lung epithelial cells protects mice from $S.$ $aureus$ induced lung injury. FIG. 2A is a timeline of experiment: Two weeks prior to nasal insufflation of $5 \times 10^8$ CFU $S.$ $aureus$, both wild-type and $Abl1^{fl/fl}$ mice were treated with tamoxifen in CC10 (Scgb1a1)-CreERT2 mice. FIG. 2B is a screenshot of a movie of wild-type and knockout mice 24 hours after nasal insufflation of $S.$ $aureus$. FIG. 2C is an image of two-minute tracing of mice performed on Adobe Premiere Pro showing a dramatic increase in mouse movement in knockout compared to wild-type mice. FIG. 2D is a graph showing bronchioalveolar lavage (BAL) showing reduced protein in knockout mice compared wild-type mice. FIG. 2E is a graph of bronchioalveolar lavage (BAL) showing reduced LDH in knockout mice compared wild-type mice. FIG. 2F is an image of H&E staining three days following nasal insufflation of $S.$ $aureus$ in wild-type and knockout mice showing increased protein and cell infiltrates in the airspace of wild-type mice compared to knockout mice. FIG. 2G is a graph showing quantification of alveolar space infiltrates on H&E sections of wild-type vs knockout mice normalized to a healthy, non-infected mouse. Graphs depict means and S.E.M. of "n" mice, where "n" represents each individual animal used (i.e. n=37 represents 37 individual mice).

FIG. 3A is a timeline of experimental protocol: Two weeks prior to nasal insufflation of $5 \times 10^8$ PFU $S.$ $aureus$, $Abl1^{fl/fl}$ mice were administered intranasal Adenovirus5-CC10-Cre virus to induce excision of Abl1 in CC10 (Scgb1a1)-expressing cells. FIG. 3B is a graph of bronchioalveolar lavage showing decreased protein accumulation in the airspace in Abl1 knockout mice (induced by either tamoxifen delivery in CC10-CreERT2 mice or Ad5-CC10-Cre virus) compared to wild-type mice.

FIG. 4A is a graph showing that 72 hours after exposure to $S.$ $aureus$, CC10 (Scgb1a1)-CreER; $Abl1^{fl/fl}$ mice demonstrate a dramatic reduction in leukocyte counts in the BAL fluid compared to wild-type mice. FIG. 4B is an image of H&E sections showing neutrophilic influx in the lungs of both wild-type and knockout mice (arrows) three days after exposure to $S.$ $aureus$, but infiltration of immune cells into the alveolar space was reduced in knockout mice compared to wild-type mice. FIG. 4C is a graph of FACS quantification of cells from BAL fluid 24 hours and 72 hours after injury. FIG. 4D is a graph of FACS quantification of cells from BAL fluid 24 hours after injury, which showed decreases in neutrophil populations without changing the proportion of neutrophil cells in the BAL fluid in knockout mice compared to wild type mice. FIG. 4E is a graph of FACS quantification of cells from BAL fluid 24 hours after injury, which showed decreases in total immune cell populations without changing the proportion of neutrophil cells in the BAL fluid in knockout mice compared to wild type mice.

FIG. 5A is a graph of FACS quantification of the non-BAL lung cell populations (interstitial and parenchymal cells) without injury and 6 h, 24 h, and 72 h after injury showing no significant changes in CD45+ cells in wild-type versus knockout mice. FIG. 5B is a graph of FACS quantification of the non-BAL lung cell populations (interstitial and parenchymal cells) without injury and 6 h, 24 h, and 72 h after injury showing no significant changes in neutrophils (Ly6G+) in wild-type versus knockout mice. FIG. 5C is a pie chart demonstrating non-BAL lung cell populations (interstitial and parenchymal cells) 24 h after injury showed no significant changes in neutrophils (Ly6G+), macrophages (F4/80+), and T-cells (CD3+) in wild-type versus knockout mice. FIG. 5D is a graph showing that BAL showed no significant difference in *S. aureus* CFU counts 24 h and 72 h after injury in wild-type versus knockout mice. FIG. 5E is a graph of non-BAL whole lung cell isolation showing no significant difference in *S. aureus* CFU counts 24 h and 72 h after injury in wild-type versus knockout mice.

FIG. 7A is a schematic of distal lung epithelial cell populations in the bronchial tree. FIG. 7B are immunofluorescence stains for RAGE (Type I alveolar epithelial cell marker), SPC (Type II alveolar epithelial cell marker), and Hoechst33342 (nuclear stain) showing that Type I alveolar epithelial cells are the most common site of injury (yellow dotted lines) following exposure to *S. aureus* in wild-type mice for 3 days. CC10 (Scgb1a1)-CreER; Rosa26-fGFP; Abl1$^{wt}$ or Abl1$^{fl/fl}$ mice that were given tamoxifen four times two weeks prior to nasal insufflation of *S. aureus* to induce excision of Abl1 and/or expression of GFP in Scgb1a1+ cells. Scale bar=100 μm. FIG. 7C are immunofluorescence staining images for the Type I cell marker, RAGE, four hours, three days, and six days following nasal insufflation of *S. aureus* showing widespread damage (loss of RAGE expression and reduced alveolar volume) to the alveolar epithelium in wild-type (WT) mice that peaks at three days and resolves in one week compared to damage in Abl1$^{fl/fl}$ (KO) mice at four hours that completely resolves by day 3. Scale bar=50 μm. FIG. 7D is a graph showing reduced damage (as measured by loss of alveolar area/volume calculated across an entire section of the left lung compared to uninfected mice) in Abl1$^{fl/fl}$ mice compared to wild-type mice three days after injury. Graphs depict means and S.E.M. of "n" mice, where "n" represents each individual animal used (i.e. n=6 represents 6 individual mice).

FIG. 8A are microscopy images for CC10 (Scgb1a1)-CreER; Rosa26-fGFP; Abl1$^{wt}$ (left panels) or Abl1$^{fl/fl}$ (right panels) mice that were given tamoxifen four times two weeks prior to nasal insufflation of *S. aureus* to induce excision of Abl1 and/or expression of GFP in Scgb1a1+ cells. Three days after exposure to the live bacteria, knockout mouse lungs demonstrated a dramatic increase in the GFP+ cell population in the alveolar space extending out from the bronchioles (Br) and BADJ. Scale bar=70 μm. FIG. 8B show microscopy images of whole left lungs from wild-type and Abl1$^{fl/fl}$ mice were sectioned and stained with a GFP antibody 24 or 72 hours following nasal insufflation of *S. aureus*. Zoomed in subsets provided for visualization of GFP+ (Scgb1a1 driver) cells in the alveolar space. FIG. 8C is a magnified subset at the 72-hour time point (a, see white box) with co-staining for GFP and SPC antibodies showing that GFP+ cell population in the alveolar space express the Type II alveolar epithelial cell marker, SPC. Scale bar=20 μm. FIG. 8D is microscopy images showing co-staining with SPC and GFP antibodies that show a dramatic expansion of GFP+ (Scgb1a1 driver) SPC+ cells throughout the alveolar space following injury. FIG. 8E is a graph of quantification of the percent of SPC+ cells expressing GFP in the entire left lungs of mice infected with *S. aureus*, which shows a doubling of the double positive, GFP+ SPC+, cell population in knockout (n=9 mice) compared to wild-type mice treated with tamoxifen (n=16 mice) 72 hours after injury. Graph represents means with S.E.M. FIG. 8F is microscopy images of staining with an antibody for CC10 (Scgb1a1) showing high expression of CC10 in cells in close proximity to the BADJ with progressively lower expression further away from the BADJ.

FIG. 9A is a timeline of the experiment: CC10 (Scgb1a1)-CreER, Rosa26-fGFP mice were treated with an Abl kinase inhibitor or vehicle control b.i.d. starting one hour after nasal insufflation of *S. aureus*. Mice were evaluated 4h, 24h, and 72h after injury. FIG. 9B is movement tracings of a 30-second video of vehicle and GNF5 treated mice 24h after induction showing faster recovery in mice treated with GNF5.

FIG. 9C is H&E staining of the left lung of vehicle and GNF5 treated mice three days after injury. FIG. 9D is a graph showing quantification of lung injury in H&E sections in vehicle and GNF5 treated mice. FIG. 9E is a graph of bronchioalveolar lavage performed three days after injury that shows a reduction in protein in the airspace in mice treated with GNF5 starting 24h before injury (Pre) or 24h after injury (Post) compared to control mice. FIG. 9F is a graph of bronchoalveolar lavage performed three days after injury that shows a reduction in protein in the airspace in mice treated with nilotinib or GNF5 24h after injury compared to control mice. FIG. 9G is microscopy images showing that three days after injury, mice treated with GNF5 (right) demonstrated an increase in the GFP+ cell population in the alveolar epithelium compared to vehicle treated mice (left). FIG. 9H is microscopy images of co-staining for GFP and SPC antibodies showed an induction of SPC expression, a marker for Type II AECs, in both the GFP+ cells of the bronchiolar (Br) and alveolar epithelium in GNF5-treated mice. FIG. 9I is a graph of quantification of the percentage of SPC+ cells from the entire left lung that were also GFP+ in mice with genetic inactivation or pharmacological inhibition of Abl kinases compared to control mice. FIG. 9J is immunofluorescence staining for the Type I AEC marker, RAGE, three days after injury showing widespread damage to the alveolar epithelium (dotted yellow lines) in untreated mice that is resolved in mice treated with GNF5. Graphs depict means and S.E.M. of "n" mice, where "n" represents each individual animal used (i.e. n=6 represents 6 individual mice).

FIG. 10A is microscopy images of CC10 (Scgb1a1)-CreER, Rosa26-fGFP, Abl1$^{wt}$ or Abl1$^{fl/fl}$ mice that were given tamoxifen four times two weeks prior to nasal insufflation of *S. aureus* to induce excision of Abl1 and/or expression of GFP in Scgb1a1+ cells. 4 hours after exposure to *S. aureus*, GFP+ cells in knockout mice (KO) exhibited increased rates of proliferation as measured by Ki67staining compared to wild-type mice (WT) Scale bar=40 µm. FIG. 10B is a graph showing the quantification of the experiment in FIG. 10A. FIG. 10C is immunofluorescence staining images that revealed an increased expression of the proliferation marker, Ki67, 24 hours following injury in the bronchioles (Br) of Abl1$^{fl/fl}$ mice compared to Abl1 $^{wt}$ mice. FIG. 10D is a graph of quantification of the fraction of GFP+ cells that were also Ki67+ in Abl1 $^{wt}$ and Abl1$^{fl/fl}$ mice without injury and 4 hours and 24 hours after delivery of *S. aureus* showing an increase in GFP+Ki67+ cells in knockout mice compared to wild-type mice (n=5-8 mice per group). FIG. 10E is microscopy images of co-staining for GFP and SPC that showed a significant increase in expression of SPC within the bronchiolar secretory cell population of Abl1 knockout mice compared to wild-type mice. Scale bar=100m. FIG. 10F is a graph of RT-PCR of lysates from isolated cells, which showed a significant increase in expression of four genes highly expressed in Type II cells in knockout mice compared to wild-type mice (n=4 mice per group). GFP+ cells were isolated from the lungs of CC10 (Scgb1a1)-CreER; Rosa26-fGFP mice by FACS sorting. FIG. 10G is a graph of RT-PCR quantification of Sftpc mRNA expression from CC10 (Scgb1a1)-CreER; L10a-eGFP mice showing an increase in actively translated Sftpc mRNA pulled down from GFP-labeled ribosomes in knockout mice compared to wild-type control mice (n=3 mice per group). Graphs represent means with S.E.M.

FIG. 11A is microscopy images 3 days after exposure to *S. aureus*. Increased damage (dotted lines) to the alveolar epithelium was observed in SPC-CreERT2; Rosa26-tdTomato; Abl1$^{wt}$ and Abl1$^{fl/fl}$ mice compared to SPC-CreERT2; Rosa26-tdTomato mice treated with the Abl kinase inhibitor, GNF5. FIG. 11B is a graph of quantification showing reduced damage (as measured by loss of alveolar area/volume compared to uninfected mice) in GNF5-treated mice compared to Abl1$^{wt}$ or Abl1$^{fl/fl}$ mice 3 days after injury. FIG. 11C is microscopy images of untreated, wild-type and knockout mice cells. No RAGE+ cells were observed that were also tdTomato+ (stained by RFP). By contrast, RAGE+, tdTomato+, SPC− cells (Cell 1) derived from RAGE−, tdTomato+, SPC+ cells (Cell 2) were observed at areas of damage in SPC-CreERT2; Rosa26-tdTomato mice treated with GNF5 three days following exposure to *S. aureus*.

FIG. 12A is microscopy images of immunofluorescence staining that showed a significant increase in the number of double positive, GFP+ SPC+, cells in GNF5 treated mice compared to vehicle treated mice 72 hours after injury. Scale bar=50 µm. FIG. 12B is a graph of quantification of the proportion of double positive cells was performed over 5 µm sections of the entire left lungs of mice (n=5 mice per group).

FIG. 13A is microscopy images three days following exposure to *S. aureus*, CC10 (Scgb1a1)-CreER; Rosa26-fGFP; Abl1$^{wt}$ mouse lungs (top) exhibiting large areas of alveolar epithelial damage shown by staining for the Type I AEC marker, RAGE. There is an accumulation of Type II AECs, indicated by staining for SPC, at sites of damage. Knockout mouse lungs (KO) (bottom) exhibit regenerated alveolar epithelium with regions of hyper-cellularity and reduced area of alveolar loss/volume. In areas of repair, a dramatic increase in double-positive GFP+ SPC+ cells were observed. FIG. 13B is lower magnification images of knockout (right) mouse lungs three days after exposure to *S. aureus* demonstrate the enhanced proliferation and differentiation of Scgb1a1+ cells to Scgb1a1+ SPC+ cells compared to wild-type (left) mouse lungs. Scale bar=50 µm. FIG. 13C is larger magnification images of cells expanded from the BADJ to sites of damage (boxes in panel B). Scale bar=20 µm. FIG. 13D is microscopy images of staining for antibodies to GFP (Scgb1a1 driver), SPC (Type II AEC marker), and RAGE (Type I AEC marker), which revealed the presence of small clusters of GFP+ RAGE+ cells that were not observed at earlier time points. Lineage tracing of Scgb1a1-expressing cells in CC10 (Scgb1a1)-CreERT2 mice using the Rosa26-fGFP reporter revealed the presence of small clusters of GFP+ RAGE+ cells at Day 30 following infection in wild-type mice. FIG. 13E is a schematic showing that following injury to the alveolar epithelium, wild-type mice (left) initiate regeneration through expansion of a rare population of double-positive Scgb1a1+(CC 10+) SPC+ cells at the BADJ and local differentiation of Type II AECs. By contrast, knockout of Abl1 in Scgb1a1-expressing cells in the bronchioles and BADJ promotes proliferation and differentiation into double-positive Scgb1a1+ SPC+ cells, which in turn mobilize to sites of injury to indirectly promote regeneration of Type I AECS from resident Type II AECS.

FIG. 14A is a graph showing reduced weight loss in knockout mice three days after injury compared to wild-type mice (n=8-14 mice per group). FIG. 14B is a graph of quantification of RAGE staining showing reduced alveolar damage (as measured by alveolar area/volume) in knockout mice compared to wild-type mice three days after infection with *S. pneumoniae* (n=5 mice per group). FIG. 14C is a graph showing that a significant expansion of double positive GFP+ SPC+ cells was observed within 6 hours after injury in knockout mice compared to wild-type mice (n=4 mice per group). Scale bar=50 µm.

FIG. 15A is a graph showing that three days after nasal insufflation of 35 PFU PR8-influenza, knockout mice showed reduced weight loss compared to wild-type, control mice (n=6 mice per group). FIG. 15B is a graph showing that three days after nasal insufflation of 35 PFU PR8-influenza, knockout mice showed a significant expansion of GFP+ SPC+ cells compared to wild-type, control mice (n=6 mice per group).

FIG. 16A is a graph of GFP+ cells were isolated from the lungs of CC10 (Scgb1a1)-CreER; Rosa26-fGFP mice through FACS sorting. RT-PCR of lysate from isolated cells showing a significant increase in expression of Yap1 and its downstream transcriptional target, Birc5 (n=3 mice per group, each sample run in triplicate). FIG. 16B is a Western blot showing protein expression of primary HBECs pre-treated with the Abl kinase inhibitor, nilotinib (N), 24 hours prior to exposure to S. aureus.

FIG. 18A is a schematic of the trophic diagram of the respiratory tree. FIG. 18B is a schematic of the cell types defining each section of the respiratory tree.

FIG. 19A is a timeline of in vitro basal cell differentiation in primary human bronchial epithelial cells (HBECs). FIG. 19B is a 3D reconstructions of air-liquid interface cultures using primary HBECs showing an increase in expression of acetylated α-tubulin (red), a marker of ciliated cells, in cells treated with the Abl inhibitor, nilotinib, compared to vehicle-treated cells 7 days after plating the cells (n=3 human patients per group, each run in triplicate). FIG. 19C is a Western blot analysis of primary HBECs showing an increase in protein expression of acetylated α-tubulin in cells treated with nilotinib (N) compared to vehicle-treated cells (CL) 7 days after plating the cells (n=3 patients per group, each run in triplicate). FIG. 19D is a graph of RT-PCR analysis of primary HBECs showing an increase in expression of SNTN, a structural protein in cilia, in cells treated with the Abl inhibitor, GNF5, compared to vehicle-treated cells 7 days after plating the cells (n=3 patients per group, each run in triplicate).

FIG. 21A is brightfield images of cells treated with vehicle, GNF5, nilotinib (not shown), or DPH two and five days after plating the cells (n=2 patients per group, each run in duplicate). FIG. 21B is immunoblots of differentiation and proliferation markers showing an increase in the ciliated cell marker, acetylated α-tubulin, a decrease in the basal cell marker, SOX2, and an increase in the proliferation marker, Ki67, in GNF5 and nilotinib treated cells compared to untreated or DPH treated cells (n=2 patients per group, each run in duplicate).

FIG. 23A is microscopy images showing pre-treatment with GNF5 24 hours before induction with sulfur dioxide protects Scgb1a1+ Club cells and acetylated α-tubulin+ ciliated cells from damage. FIG. 23B is a graph of quantification of acetylated α-tubulin+ ciliated cells 24 hours after induction with sulfur dioxide in whole tracheas from the tracheoesophageal junction to distal trachea, which shows protection of ciliated cells in mice treated with GNF5 compared to control mice (n=3 mice per group).

FIG. 26A is 3D-reconstructions of μ-CT scans of mice before and after 14 days of treatment with vehicle, GNF5, standard dose of docetaxel (20 mg/kg, biweekly), or GNF5+ sub-therapeutic dose of docetaxel (4 mg/kg, biweekly). FIG. 26B is the corresponding H&E sections of mouse lungs after 14 days of treatment. FIG. 26C is a graph of quantification of tumor volumes in each treatment group.

FIG. 27A is IHC for Ki67+ cells in sections of mouse lungs from mice treated with vehicle control, docetaxel, GNF5, or combination (docetaxel+GNF5) treatment showing a decrease in Ki67 staining, particularly in the combination therapy group. FIG. 27B is a graph of immunofluorescence analysis showing an increased in the percentage of Ki67+ tumor cells (labeled with farnesylated GFP) in control mice compared to mice given a combination therapy of GNF5 and docetaxel. FIG. 27C is an immunoblot of lysates showing a decrease in Ki67 expression and increase in cleaved caspase 3 expression in mice given combination therapy compared to control mice.

FIG. 28A is a schematic model showing: SPC (Sftpc)-CreERT2; $KRAS^{LSL-G12D}$; $p53^{fl/fl}$; Rosa26-tdTomato mice were given tamoxifen to induce tumor formation. Tomato+ cells were then isolated from mice after tumor formation and grown in Matrigel in transwell inserts in the presence of primary mouse fibroblasts (derived from PDGFRα-H2B: GFP mice) to evaluate tumor organoid formation. Organoids were treated with vehicle, GNF5, docetaxel, or combination treatment for 2 weeks and assessed for organoid size. FIG. 28B is a graph showing that 2 weeks after treatment, a significant reduction in organoid size was observed in organoids given combination treatment compared to vehicle, GNF5, or docetaxel.

FIG. 30A is graphs of RT-qPCR analysis of cell lysate from each group shows an increase in expression of terminal cell markers (SPC: Type II cell marker and CC10: secretory cell marker) with a corresponding decrease in expression of basal cell markers (p63) in mice treated with the combination therapy compared to control or single agent treatment. FIG. 30B is Western blots showing the change in protein expression of differentiation and basal markers in mice treated with docetaxel and GNF5. Phospho-CrkL is shown as a surrogate marker for Abl kinase activity along with the loading control, GAPD.

DETAILED DESCRIPTION OF THE DISCLOSURE

Figure 1B:
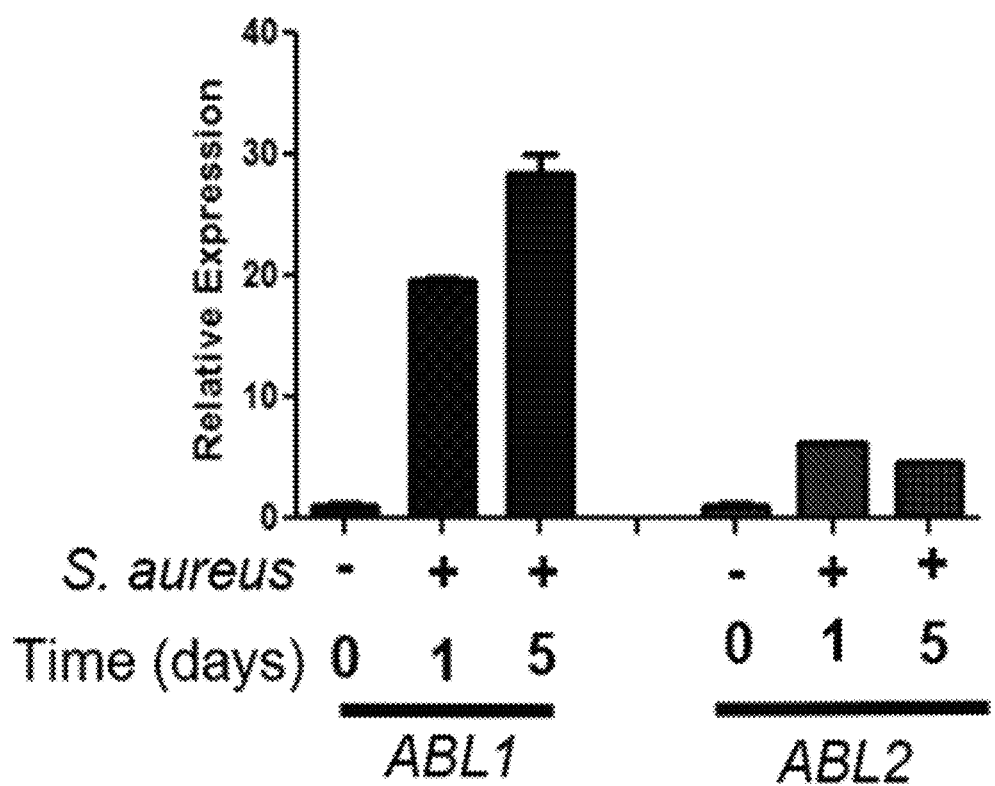

For the purposes of promoting an understanding of the principles of the present disclosure, reference will now be made to embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.
Definitions Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In certain embodiments, the subject comprises a human having a pathogenic-induced and/or chemically-induced lung injury.

"Administration" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

As used herein, "Abl kinase inhibitor" refers to any compound capable of disrupting, blocking, or inhibiting the expression and/or function (including the signal transduction pathway) of Abl kinase(s) (e.g., Abl1), in a cell, including the Bcl-Abl pathway. The term "Abl kinase inhibitor" is meant to include one or more compounds capable of disrupting, blocking, or inhibiting the expression and/or function, i.e. the term may include two or more inhibitors that may be used in combination, including sequential or concomitant administration. The Abl kinase inhibitors as used with the present invention may be Abl kinase specific inhibitors. The Abl kinase inhibitors may be allosteric inhibitors.

As used herein, "an interfering oligonucleotide" refers to any oligonucleotide that interferes with, i.e. reduces, inhibits, or eliminates, the expression of an Abl kinase. Interfering oligonucleotides include aptamers and other oligonucleotide molecules as described herein.

Unless otherwise defined, all technical terms used herein have the same meaning as commonly understood by one of ordinary skill in the art to which this disclosure belongs.

Inhibition of Abl Kinases for the Treatment of Lung Injury and the Regeneration of Lung Epithelial Cells Following Lung Injury The inventors have surprisingly discovered that Abelson (Abl) kinases may serve as therapeutic targets in the treatment of lung injury, including pathogen-induced and chemical-induced lung-injury. In particular, the inventors have discovered a previously unknown role for Abl kinases in the regulation of regeneration in the lung epithelium after pathogen- or chemical-induced injury. The Abl kinases, Abl1 and Abl2, are a family of non-receptor tyrosine kinases that regulate a wide variety of cellular processes during development and normal homeostasis, but can have deleterious effects on cell survival, proliferation, and cell-cell junction adhesion upon their upregulation following inflammation, tumorigenesis, and oxidative stress.

The inventors have discovered that genetic and pharmacological inactivation of Abl kinases enhances proliferation and differentiation of a subpopulation of lung epithelial cells following lung injury and mobilizes secretory cells from the distal airway and bronchioalveolar duct junction to promote the expansion of double-positive SCGB1A1+ SPC+ cells, leading to enhanced regeneration of the damaged lung alveolar epithelium following lung injury, e.g. bacterial infection induced by live *S. aureus* and other bacterial and viral pathogens.

Accordingly, Abl kinase inhibitors, including Abl kinase specific inhibitors, which have been used for treating leukemia, can be re-purposed to treat the damaged lung following pathogen or chemical exposure, and therapeutic strategies to promote lung epithelial cell regeneration after injury could profoundly improve patient outcomes when used in combination with antibiotics and supportive care.

In particular, the inventors have found that treatment of mice with an Abl kinase inhibitor promotes recovery following *Staphylococcus aureus*-, *Streptococcal pneumonia*-, and influenza-induced pneumonia, even in the absence of antibiotics. The inventors have further found that conditional knockout of Abl1 in a single airway cell-type, Scgb1a1-expressing epithelial cells in mouse lungs, is sufficient to recapitulate the phenotype observed in mice treated with an Abl kinase inhibitor, as mice knockout for Abl1 in Scgb1a1-expressing cells exhibit accelerated regeneration of the alveolar epithelium following bacterial pneumonia compared to control mice. The inventors have additionally found that knockout of Abl1 in Scgb1a1 (but not Sftpc)-expressing cells, greatly enhances the expansion of double-positive cells co-expressing the secretory cell marker, Scgb1a1, and the Type II alveolar marker, SPC (Sftpc), which expand to sites of injury to promote alveolar regeneration. Further, the inventors have found that treatment of SOX2-eGFP mice with an Abl allosteric inhibitor resulted in dramatic expansion of GFP+ cells from the airways to the alveolar space after pathogen exposure. Unlike Scgb1a1 (also known as CC10), SOX2 is not expressed outside of the airway compartment in the lung. Thus, inactivation of Abl1 specifically in Scgb1a1+ SOX2+ airway cells contributes to the regeneration phenotype after lung injury. In addition, the inventors have found that knockout of Abl1 in Scgb1a1/CC10+ epithelial cells does not confer differential susceptibility to *S. aureus* infection or alter the immune response compared to wild type mice. Rather, epithelial regeneration occurs within hours after injury and precedes the immune response.

Accordingly, in a first aspect the present invention provides a method of treating lung injury in a subject in need thereof, comprising administering to the subject a therapeutically effective amount of an Abl kinase inhibitor.

In a second aspect, the present invention provides a method of regenerating lung epithelial cells following lung injury in a subject, comprising administering to the subject a therapeutically effective amount of Abl kinase inhibitor.

In certain embodiments of the above aspects of the invention, the lung injury comprises lung epithelial cell damage. In some embodiments, the lung injury is a pathogen-induced lung injury. In certain embodiments, the pathogen-induced lung injury is bacterial or viral pneumonia.

The pathogen responsible for the pathogen-induced lung injury can be any pathogen that may infect the upper or lower airway, and/or any pathway known to damage lung tissue and/or cells, including lung epithelial cells, or any combination thereof. Such pathogens would be known to one of skill in the art. Exemplary pathogens responsible for the pathogen-induced lung injury include, but are not limited to, methicillin-resistant bacteria and other multi-dug resistant pathogens, *Staphylococcus aureus*, *Streptococcal pneumoniae*, and influenza strains. In certain embodiments, the pathogen responsible for the pathogen-induced lung injury is *Staphylococcus aureus*, *Streptococcal pneumoniae*, or influenza.

In other embodiments, the lung injury is a chemical-induced lung injury. The chemical responsible for the chemical-induced lung injury can be any chemical known to harm or destroy airways, and/or damage lung tissue and/or cells, including lung epithelial cells, or any combination thereof. The chemical-induced lung injury may arise from exposure to toxic levels of the chemical, e.g. from an acute exposure to the chemical, or from a sustained exposure to the chemical over time. Exemplary chemicals responsible for the chemical-induced lung injury include, but are not limited to, naphthalene, sulfur dioxide, atmospheric chemicals, pollutants, airborne hazards in burn pits and mineralized dust, chemicals in cigarette smoke, and chemicals in the vapors of substances associated with vaping/e-cigarette devices. In certain embodiments, the chemical responsible for the chemical-induced lung injury is sulfur dioxide.

In certain embodiments, the subject is a mammal. In some embodiments, the mammal is a human.

Abl Kinase Inhibitors

Exemplary Abl kinase inhibitors include, but are not limited to, imatinib, nilotinib, dasatinib (BMS-354825), bosutinib (SKI-606), Ponatinib (AP24534), Bafetinib (INNO-406), GNF2, GNF5, ABL001, HG-7-85-01, Tozasertib (MK-0457, VX-680), Danusertib (PHA-739358), Rebastinib (DCC-2036), Axitinhib (AG013736), Vandetanib (ZD-6474), 1,3,4-thiadiazole derivatives, and the compound having the structure

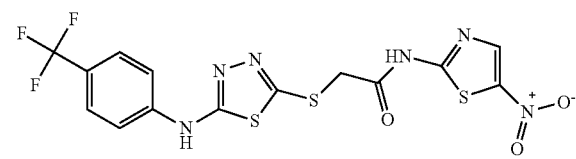

and combinations thereof and pharmaceutical compositions thereof. In certain embodiments, the Abl inhibitor is an allosteric inhibitor selected from the group consisting of GNF2, GNF5, and ABL001. In some embodiments, the Abl kinase inhibitor comprises GNF5. In other embodiments, the Abl kinase inhibitor comprises nilotinib.

Additional Abl inhibitors that may be used with the compositions and methods disclosed herein are as follows:

GNF5, ABL (T315I) kinase Inhibitor AMBIT, ABL001, ACTB1011, Admine, AEG41174, Agacel, AL18, Altanib, APG1351, APO-Imatinib, ARRY614, AT9283, AZD0424, BcrAbl/Lyn Inhibitor, AB SCIENCE, Benznib, BL001, C-Abl Inhibitors IIUM, Cadinib, Celonib, Dasanat, Dasatinib, ACCURE, Dasatinib HETERO, Dasatinib JODAS, Dasatinib LIFEPHARMA FZE, Dasatinib SRS PHARMA, Dasatinib VALEANT, DCC2036, Defect Shoe, Degrasyns CALLISTO, Enliven, Fontrax, Gelike, Gistamel, Gleevec, Gleevec KEDEM, Gleevec-NP CAPSULUTION, Glimatinib, Glinib, Glitive, GLYBULEN, HHGV678, HM95091, Hronileucem, HyNap-Nilo, I-Teenib, Iclusig, IkT-001, IkT-001Pro, Imaget, Imakrebin, Imalek, Imanib, Imanix, Imarem, Imat Imatenil, Imatenil NEUTEC, Imatib, Imatinate, Imatinb, Imatinib ACCURE, Imatinib ADMAC, Imatinib ALLERGAN, Imatinib ALVOGEN, Imatinib AQVIDA, Imatinib ASCENDIS, Imatinib COOPER, Imatinib DENK, Imatinib Ecker hydrochloride, Imatinib ERIOCHEM, Imatinib, EUROFARMA, Imatinib FARMAPROJECTS, Imatinib FLAGSHIP BIOTECH, Imatinib GENEX, Imatinib INDIAN DRUGS, Imatinib JODAS, Imatinib LAFEDAR, Imatinib LIFEPHARMA FZE, Imatinib mesylate AMNEAL, Imatinib mesylate CAMUS, Imatinib mesylate CELOGEN, Imatinib mesylate *CYGNUS*, Imatinib mesylate CYNO PHARMACEUTICALS, Imatinib, mesylate DAIICHI SANKYO, Imatinib mesylate DOC, Imatinib mesylate EUROFARMA, Imatinib mesylate EXVASTAT, Imatinib mesylate HARVEST MOON, Imatinib mesylate HETERO, Imatinib mesylate LABORATORIOS INDUQUIMICA, Imatinib mesylate MEDAC, Imatinib Mesylate NAPROD, Imatinib mesylate NICHIIKO, Imatinib mesylate PHARMERICA, Imatinib mesylate PRIME PHARMA, Imatinib mesylate SAVA, Imatinib mesylate SINO BIO, Imatinib Mesylate SRS PHARMA, Imatinib mesylate STERLING, Imatinib mesylate SYNTHON, Imatinib mesylate TAKATA, Imatinib mesylate ZENTIVA, Imatinib OSVAH Imatinib SALIUS, Imatinib UNITED BIOTECH, Imatinib VIVIMED, Imatinib WORLD MEDICINE, ImatiRel, Imatis, Imatoz, Imavec, Imavec HELM, Imicap, Imimark, Inivec INN0406, Itnib, Kimatinib, KW2449, Leukivec, Leutipol, Leuvec, Leuzek, Levin DR REDDYS, Liteda, LS 104, Lupinib, MAAC002, Matinic, Meaxin, Megavec, Mesinib, Mitinab, Nibix, Nibix SOPHARMA, Nilotinib FARMAPROJECTS, Nilotinib JODAS, Nilotinib LIFEPHARMA FZE, NRCAN019, Nutab, ON012380, ON044580, ON146040, PF114, PHA680626, Philachromin, Rembre, Sagitta, SAR103168, SGX393, SKLB1028, Sprycel, Sprytinib, Stimanib, Stritinib, SUN-K0706, SUN-K954, Supect, Tagonib, Tasigna, TG100598, Tibaldix, Timab, Tinima, Veenat NATCO, Veenat RADIANCE, Vek, VX680, Xin dimension, XL228, Zafranib, Ziatir, Zimitib and combinations thereof.

Also contemplated by the present disclosure are other types of inhibitors of Abl kinases/Bcl-Abl pathways, including but not limited to, the following:

i. Aptamers

Aptamers, also called nucleic acid ligands, are nucleic acid molecules characterized by the ability to bind to a target molecule with high specificity and high affinity. Almost every aptamer identified to date is a non-naturally occurring molecule.

Aptamers to a given target (e.g. an Abl kinase(s)) may be identified and/or produced by the method of Systematic Evolution of Ligands by EXponential enrichment (SELEX™). Aptamers and SELEX are described in Tuerk and Gold (Systematic evolution of ligands by exponential enrichment: RNA ligands to bacteriophage T4 DNA polymerase. Science. 1990 Aug. 3; 249(4968):505-10) and in WO91/19813.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesized by methods which are well known to the skilled person. For example, aptamers may be chemically synthesized, e.g. on a solid support.

Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer.

Aptamers can be thought of as the nucleic acid equivalent of monoclonal antibodies and often have $K_d$'s in the nM or pM range, e.g. less than one of 500 nM, 100 nM, 50 nM, 10 nM, 1 nM, 500 pM, 100 pM. As with monoclonal antibodies, they may be useful in virtually any situation in which target binding is required, including use in therapeutic and diagnostic applications, in vitro or in vivo. In vitro diagnostic applications may include use in detecting the presence or absence of a target molecule.

Aptamers according to the present disclosure may be provided in purified or isolated form. Aptamers according to the present disclosure may be formulated as a pharmaceutical composition or medicament.

Suitable aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

Suitable aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Suitable aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

ii. Oligonucleotide Repression of Abl Kinase Expression

Oligonucleotide molecules, particularly RNA, may be employed to regulate gene expression. These include antisense oligonucleotides, targeted degradation of mRNAs by small interfering RNAs (siRNAs), small molecules, post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for Abl kinases, oligonucleotides may be designed to repress or silence the expression of Abl kinases (e.g., those regulated by the Abl1 gene). Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the Abl1 kinase mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of Abl kinase expression will preferably result in a decrease in the quantity of Abl kinase(s) expressed by a cell. For example, in a given cell the repression of Abl kinase by administration of a suitable nucleic acid will result in a decrease in the quantity of Abl kinase expressed by that cell relative to an untreated cell. Repression may be partial. Preferred degrees of repression are at least 50%, more preferably one of at least 60%, 70%, 80%, 85% or 90%. A level of repression between 90% and 100% is considered a ' silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNAs are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

Accordingly, the present disclosure provides the use of oligonucleotide sequences for down-regulating the expression of Abl kinases.

siRNA ligands are typically double stranded and, in order to optimize the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of the Abl kinase. Preferably, the shRNA sequence is between 40 and 100 bases in length, more preferably between 40 and 70 bases in length. The stem of the hairpin is preferably between 19 and 30 base pairs in length. The stem may contain G-U pairings to stabilize the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of the Abl kinase.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific (e.g. heart, liver, kidney or eye specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of Abl kinase repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long-term expression of the therapeutic oligonucleotide. Examples include lentiviral (Nature 2009 Jan. 22; 457 (7228):426-433), adenovirus (Shen et al., FEBS Lett 2003 Mar. 27; 539(1-3)111-4) and retroviruses (Barton and Medzhitov PNAS Nov. 12, 2002 vol. 99, no. 23 14943-14945).

In other embodiments a vector may be configured to assist delivery of the therapeutic oligonucleotide to the site at which repression of Abl kinase expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations (Wang et al., AAPS J. 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methylthio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, Sethylcytosine, 5-butyluracil, 5-pentyluracil, 5-pentylcytosine, and 2,6,diaminopurine, methylpsuedouracil, 1-methylguanine, 1-methylcytosine.

Methods relating to the use of RNAi to silence genes in C. elegans, Drosophila, plants, and mammals are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619, and Elbashir S M, et al., 2001 Nature 411:494-498).

Accordingly, the present disclosure provides a nucleic acid that is capable, when suitably introduced into or expressed within a mammalian, e.g. human, cell that otherwise expresses Abl kinase(s), of suppressing Abl kinase expression by RNAi.

The nucleic acid may have substantial sequence identity to a portion of the Abl kinase mRNA, or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridize with each other. In a mammalian cell, the hairpin structure may be cleaved from the molecule by the enzyme DICER, to yield two distinct, but hybridized, RNA molecules.

Only single-stranded (i.e. non self-hybridized) regions of an mRNA transcript are expected to be suitable targets for RNAi. It is therefore proposed that other sequences very close in the Abl kinase mRNA transcript may also be suitable targets for RNAi.

Accordingly, the present disclosure provides nucleic acids that are capable, when suitably introduced into or expressed within a mammalian cell that otherwise expresses Abl kinase(s), of suppressing Abl kinase expression by RNAi, wherein the nucleic acid is generally targeted to the sequence of, or portion thereof, of the Abl kinase.

By "generally targeted" the nucleic acid may target a sequence that overlaps with the Abl kinase. In particular, the nucleic acid may target a sequence in the mRNA of human Abl kinase that is slightly longer or shorter than one of Abl kinase, but is otherwise identical to the native form.

It is expected that perfect identity/complementarity between the nucleic acid of the invention and the target sequence, although preferred, is not essential. Accordingly, the nucleic acid of the invention may include a single mismatch compared to the mRNA of the Abl kinase. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences for the Abl kinase. However, it is also expected that slightly shorter or longer sequences directed to the same region of the Abl kinase mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in *Drosophila* show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c; Czaudema et al. 2003).

Any dinucleotide overhang may therefore be used in the antisense strand of the siRNA. Nevertheless, the dinucleotide is preferably —UU or -UG (or -Tr or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The present disclosure also provides single-stranded nucleic acids (herein referred to as single-stranded siRNAs) respectively consisting of a component strand of one of the aforementioned double-stranded nucleic acids, preferably with the 3'-overhangs, but optionally without. The present disclosure also provides kits containing pairs of such single-stranded nucleic acids, which are capable of hybridizing with each other in vitro to form the aforementioned double-stranded siRNAs, which may then be introduced into cells.

The present disclosure also provides DNA that, when transcribed in a mammalian cell, yields an RNA (herein also referred to as an shRNA) having two complementary portions which are capable of self-hybridizing to produce a double-stranded motif or a sequence that differs from any one of the aforementioned sequences by a single base pair substitution.

The complementary portions will generally be joined by a spacer, which has suitable length and sequence to allow the two complementary portions to hybridize with each other. The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Wash., USA) is UUCAAGAGA. In this and other cases, the ends of the spacer may hybridize with each other.

Similarly, the transcribed RNA preferably includes a 3' overhang from the downstream complementary portion. Again, this is preferably —UU or -UG, more preferably -UU.

Such shRNA molecules may then be cleaved in the mammalian cell by the enzyme DICER to yield a double-stranded siRNA as described above, in which one or each strand of the hybridized dsRNA includes a 3' overhang.

Techniques for the synthesis of the nucleic acids of the invention are of course well known in the art.

The skilled person is well able to construct suitable transcription vectors for the DNA of the present disclosure using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-III promoter (H1) and a $T_5$ transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the present disclosure may be introduced into mammalian cells in vitro or in vivo using known techniques, as described below, to suppress expression of the Abl kinase.

Similarly, transcription vectors containing the DNAs of the present disclosure may be introduced into cells (e.g., lung cells) in vitro or in vivo using known techniques, as described below, for transient or stable expression of RNA, again to suppress expression of the Abl kinase.

Accordingly, the present disclosure also provides a method of suppressing Abl kinase expression in a mammalian, e.g. human, cell, the method comprising administering to the cell a double-stranded siRNA of the present disclosure or a transcription vector of the present disclosure.

Similarly, the present disclosure further provides a method of treating a pathogenically-induced and/or chemically-induced lung injury in the subject, the method comprising administering to a subject a double-stranded siRNA of the invention or a transcription vector of the present disclosure.

The present disclosure further provides the double-stranded siRNAs of the present disclosure and the transcription vectors of the present disclosure, for use in a method of treatment, preferably a method of treating a pathogen-induced and/or chemical-induced lung injury in a subject.

The present disclosure further provides the use of the double-stranded siRNAs of the present disclosure and the transcription vectors of the present disclosure in the preparation of a medicament for the treatment of a pathogenically-induced and/or chemically-induced lung injury in a subject.

The present disclosure further provides a composition comprising a double-stranded siRNA of the present disclosure or a transcription vector of the present disclosure in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the present disclosure are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE dextran and calcium phosphate precipitation. In vivo gene transfer techniques include transfection with viral (typically retroviral) vectors and viral coat protein-liposome mediated transfection (Dzau et al. (2003) Trends in Biotechnology 11, 205-210).

In particular, suitable techniques for cellular administration of the nucleic acids of the present disclosure both in vitro and in vivo are disclosed in the following articles:

General reviews: Borkhardt, A. 2002. Blocking oncogenes in malignant cells by RNA interference-new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCR5. Proc Natl Acad Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7. Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in U.S. Pat. Nos. 6,649,192B and 5,843,509B.

Administration of Abl Kinase Inhibitors

The Abl kinase inhibitors may be administered to a subject, either alone or as a composition comprising the Abl kinase inhibitor and a pharmaceutically acceptable carrier/excipient (i.e., a pharmaceutical composition), in an amount sufficient to induce an appropriate response in the subject.

The present disclosure further provides for the administration to a subject an effective amount of a CAR-T cell population for use with the methods disclosed herein. An "effective amount" as used herein means an amount which provides a therapeutic or prophylactic benefit. Effective amounts of the compositions/pharmaceutical compositions provided herein can be determined by a physician with consideration of individual differences in age, weight, tumor size, extent of infection or metastasis, and condition of the patient (subject). The optimal dosage and treatment regime for a particular patient can readily be determined by one skilled in the art of medicine by monitoring the patient for signs of disease and adjusting the treatment accordingly.

An effective amount of the composition(s) described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

A "pharmaceutically acceptable excipient and/or carrier" or "diagnostically acceptable excipient and/or carrier" includes but is not limited to, sterile distilled water, saline, phosphate buffered solutions, amino acid-based buffers, or bicarbonate buffered solutions. An excipient selected and the amount of excipient used will depend upon the mode of administration. Administration comprises an injection, infusion, or a combination thereof. Any suitable combination of pharmaceutically acceptable carriers or excipients may be used, and as used herein the phrase "carrier or excipient" is meant to be inclusive of any individual carrier or excipient, or any combination of carrier(s) and/or excipient(s).

An effective amount for a particular subject/patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The composition(s) according to the present disclosure may also be administered with one or more additional therapeutic agents. Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Co-administration need to refer to administration at the same time in an individual, but rather may include administrations that are spaced by hours or even days, weeks, or longer, as long as the administration of the one or more therapeutic agents is the result of a single treatment plan. The co-administration may comprise administering the composition(s) of the present disclosure before, after, or at the same time as the additional therapeutic agent. By way of example, the composition(s) of the present disclosure may be given as an initial dose in a multi-day protocol, with additional therapeutic agent(s) given on later administration days; or the additional therapeutic agent(s) given as an initial dose in a multi-day protocol, with the composition(s) of the present disclosure given on later administration days. On another hand, one or more additional therapeutic agent(s) and the composition(s) of the present disclosure may be administered on alternate days in a multi-day protocol. In still another example, a mixture of one or more additional therapeutic agent(s) and the compositions of the present disclosure may be administered comcurrently. This is not meant to be a limiting list of possible administration protocols.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

Formulations of the one or more therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Inhibition of Abl Kinases for the Treatment of Cancer and for the Sensitization of Cancer to Chemotherapy The inventors have also surprisingly discovered that the administration of Abl inhibitors renders lung adenocarcinomas susceptible to chemotherapy, thus providing for a new therapeutic approach for the treatment of lung adenocarcinomas with poor response to chemotherapy. In particular, the inventors found that the treatment of tumor-bearing mice with an Abl allosteric inhibitor promoted differentiation of lung adenocarcinomas from poorly differentiated tumors expressing basal cell markers to tumors expressing terminal differentiation markers in vivo, which rendered lung adenocarcinomas susceptible to chemotherapy.

Accordingly, in a third aspect, the present invention provides a method of treating cancer in a subject in need thereof, comprising administering to the subject a therapeutically effective amount of an Abl kinase inhibitor in combination with a chemotherapeutic agent.

In a fourth aspect, the present invention provides a method of sensitizing a subject suffering from cancer to a chemotherapeutic agent comprising administering to the subject a therapeutically effective amount of an Abl kinase inhibitor.

In certain embodiments of the third and fourth aspects of the invention, the cancer is lung cancer. In some embodiments, the lung cancer is non-small cell lung cancer, and in other embodiments, the lung cancer is lung adenocarcinoma.

In certain embodiments, the subject is a mammal. In some embodiments, the mammal is a human.

The Abl kinases that may be used with the third and fourth aspects of the invention are in accordance with the disclosure provided above.

In some embodiments, the chemotherapeutic agent is selected from the group consisting of cisplatin, carboplatin, docetaxel, gemcitabine, paclitaxel, vinorelbine, and pemetrexed, or any combination thereof. Suitable chemotherapeutic agents would be known to one of skill in the art. In certain embodiments, the chemotherapeutic agent may be docetaxel or cisplatin.

In certain embodiments, the chemotherapeutic agent may be administered at a sub-therapeutic dose, i.e. at a level less than the therapeutically effective level required for administration in the absence of an Abl kinase inhibitor.

The following Examples are provided by way of illustration and not by way of limitation.

EXAMPLES

Materials and Methods

Bacteria.

*S. aureus* (Ssp. *aureus*, No. 25923; American Type Culture Collection) was grown as previously described (Suliman H B et al. (2017) Mitochondrial quality control in alveolar epithelial cells damaged by *S. aureus* pneumonia in mice. *American journal of physiology. Lung cellular and molecular physiology* 313(4):L699-L709). Dilutions of $5 \times 10^8$ CFU were used for mouse experiments, and dilutions of $1 \times 10^8$ CFU were used for cell culture experiments. *S. pneumoniae* (serotype 19, No. 49619; American Type Culture Collection) was grown as previously described (Gomez J C, et al. (2016) *Journal of immunology* 197(7):2864-2879). Dilutions of $6 \times 10^5$ CFU were used for mouse experiments.

Cell Culture.

Primary human bronchial epithelial cells were isolated as previously described (Fulcher M L & Randell S H (2013) *Methods Mol Biol* 945:109-121) and passage 1 cells were derived from human lungs unsuitable for transplantation from non-smoker organ donors without pre-existing lung disease under protocol #03-1396 approved by the University of North Carolina at Chapel Hill Biomedical Institutional Review Board. Informed consent was obtained from authorized representatives of all organ donors. 30,000 cells were plated into each well of 6.5 mm polyester inserts containing 0.4 μm pores (Sigma-CLS3470) coated with Type IV human placenta collagen (Sigma-C7521). 100 μl of ALI medium was added to the insert and 600 μl of ALI medium was added to the well at the time of plating. At Day 3, ALI medium from the insert was removed while that in the well was changed daily for 28 days. At Day 28, the inserts containing the cells were removed from their wells, washed with PBS, and incubated at 37° C. for 30 minutes with $1 \times 10^8$ CFU *S. aureus*. Cells were then washed three times with PBS and returned to wells containing 600 μl of ALI medium to regrow. Cells were harvested at multiple time points up to five days after injury for protein or RNA extraction. All cultures were maintained at 37° C. in humidified air containing 5% $CO_2$.

Immunoblotting.

Cells were lysed in radioimmunoprecipitation assay (RIPA) buffer with protease and phosphatase inhibitors, and cell debris was removed by microcentrifugation. Protein was quantified, and equal amounts of protein was separated by SDS-polyacrylamide gel electrophoresis (BioRad-1610183) and transferred onto 0.2 μm pore nitrocellulose membranes. Membranes were probed with antibodies to ABL1 (BD-554148), ABL2 (Santa Cruz-sc 134268), and α-tubulin (Millipore-05829) overnight at 4° C., thoroughly washed, and then incubated with secondary HRP-tagged antibodies for one hour at room temperature. Blots were incubated using chemiluminescent reagents (ThermoFisher-34580) and developed using x-ray film (GE-45001).

Real-Time RT-qPCR.

RNA was isolated from cells using an RNA isolation kit (GE-25050071), and complementary DNA was synthesized using oligo(dT) primers and Moloney murine leukemia virus reverse transcriptase (Invitrogen). Real-time PCR was performed using iQ SYBR Green Supermix (BioRad-1708882). The primers used were as follows:

TABLE 1

List of RT-qPCR Primers

| Gene | Species | Sequence (5' to 3') |
| --- | --- | --- |
| ABL1 (forward) | Human | GGCTGTGAGTACCTTGCTGC (SEQ ID NO: 01) |
| ABL1 (reverse) | Human | GGCGCTCATCTTCATTCAGGC (SEQ ID NO: 02) |
| ABL2 (forward) | Human | AGTTTAGCACCAGGGTTCATCAG (SEQ ID NO: 03) |
| ABL2 (reverse) | Human | CTTCCTATCCCTGGTGAAGCAT (SEQ ID NO: 04) |
| Gapdh (forward) | Mouse | AGGTCGGTGTGAACGGATTTG (SEQ ID NO: 05) |
| Gapdh (reverse) | Mouse | TGTAGACCATGTAGTTGAGGTCA (SEQ ID NO: 06) |
| Sftpc (forward) | Mouse | AACGCCTTCTCATCGTGGT (SEQ ID NO: 07) |
| Sftpc (reverse) | Mouse | TAGATATAGTAGAGTGGTAGCT (SEQ ID NO: 08) |
| ETV5 (forward) | Mouse | CCCGGATGCACTCTTCTCTATG (SEQ ID NO: 09) |
| ETV5 (reverse) | Mouse | TCGGATTCTGCCTTCAGGAA (SEQ ID NO: 10) |
| Lamp3 (forward) | Mouse | TGGAGCATATTTGACCATCTCA (SEQ ID NO: 11) |
| Lamp3 (reverse) | Mouse | CAAAGGCCTGAAGGTGGATA (SEQ ID NO: 12) |

TABLE 1-continued

List of RT-qPCR Primers

| Gene | Species | Sequence (5' to 3') |
|---|---|---|
| Sftpa (forward) | Mouse | CTGTCCCAAGGAATCCAGAG (SEQ ID NO: 13) |
| Sftpa (reverse) | Mouse | CCGTCTGAGTAGCGGAAGTC (SEQ ID NO: 14) |

Analysis was performed using a BioRad CFX384 real-time machine and CFX Manager software. PCR assays were performed in duplicate. The expression of each gene was normalized to that of GAPDH (human) or Gapdh (mouse).

Mice.

TABLE 2

List of Employed Cre-Driven Mouse Models

| Mouse Model | Modification | Information |
|---|---|---|
| CC10-CreERT; Rosa26-fGFP | Scgb1a1$^{tm1(cre/ERT)Blh}$/J | Driver: Scgb1a1 (CC10) Reporter: farnesylated GFP |
| CC10-CreERT; L10a-eGFP | Scgb1a1$^{tm1(cre/ERT)Blh}$/J Gt(ROSA)26Sor$^{tm9(EGFP/Rpl10a)Amc}$ | Driver: Scgb1a1 (CC10) Reporter: ribosome-tagged GFP |
| Sox2-eGFP | Sox2$^{tm2Hoch}$ | Knockin/knockout mouse: ORF of Sox2 is replaced by EGFP |
| SPC-CreERT2; Rosa26-tdTomato | Sftpc$^{tm1(cre/ERT2)Blh}$ | Driver: Sftpc (SPC) Reporter: tdTomato |

CC10 (Scgb1a1)-CreERT; Rosa26R-CAG-farnesylated GFP (Rosa26-fGFP) and SPC (Sftpc)-CreERT2; Rosa26-tdTomato mice were kindly provided by Dr. Mark Onaitis and generated by Dr. Brigid Hogan at Duke University and have been previously described (Rawlins E L. et al. (2009) Cell stem cell 4(6):525-534, Xu X et al. (2012) Proc Natl Acad Sci USA 109(13):4910-4915). These mice were crossed with Abl1$^{flox/flox}$ mice (Moresco E M, et al. (2005) J Neurosci 25(26):6105-6118) into a C57BL/6 genetic background. Sox2$^{tmHoch}$/J mice (referred to as SOX2-eGFP mice in the text) were purchased from the Jackson Laboratory. Gt(Rosa)26Sor$^{tm9(EGFP/Rpl10z)Amc}$/J (referred to as L10-eGFP in the text) mice were purchased from the Jackson Laboratory and were crossed to CC10-CreERT; Abl1$^{flox/flox}$ mice into a C57BL/6 genetic background for the TRAP experiments. To induce expression of Cre-recombinase for both TRAP experiments and lineage tracing experiments, 8- to 20-week-old male and female mice were injected intraperitoneally four times every other day with 0.25 mg/g body weight Tamoxifen (Sigma-T5648) in corn oil (Spectrum-CO136). Exposure to S. aureus was initiated 15 days after the last dose of Tamoxifen. Alternatively, mice were inoculated with purified Adenovirus5-CC10-Cre virus obtained from the University of Iowa Viral Vector Core Facility and generated by Dr. Anton Berns (Netherlands Cancer Institute). 10 μl of stock virus solution was mixed in 30 μl of Minimum Essential Medium and delivered intranasally twice, three days apart, three weeks prior to induction of S. aureus pneumonia. Mice were anesthetized using 0.3 mg xylazine and 2.5 mg/kg ketamine intraperitoneally prior to intranasal inoculation with a 50 μl dilution of 5×10$^8$ S. aureus. The mice were monitored daily for weight loss and signs of respiratory distress and euthanized in an isofluorane chamber at days 0, 1, 2, and 3 after inoculation. All experiments were performed under the Duke University IACUC approved protocols: A098-16-04 and A130-16-06. Male and female mice at different ages (8 to 20 weeks old) were evaluated for differential response to drug (Abl kinase inhibitors and tamoxifen) and/or injury, and no significant effects of age and gender were observed.

Inhibitors.

GNF5 (N-(2-Hydroxyethyl)-3-(6-(4-(trifluoromethoxy) phenylamino) pyrimidin-4-yl)benzamide) was synthesized at the Duke University's Small Molecule Synthesis Facility, and validated by LC-MS and 1H-NMR/FT-IR spectra and with cell-based assays that confirm potencies and cell signaling inhibitory activities. For in vivo experiments, GNF5 was prepared in a suspension with 0.5% methylcellulose and 0.5% Tween-80 at a concentration of 10 mg/mL, and mice were treated with either 20 mg/kg, 40 mg/kg, or 100 mg/kg b.i.d. via oral gavage. Nilotinib was synthesized at the Duke University's Small Molecule Synthesis Facility, and validated by LC-MS and 1H-NMR/FT-IR spectra. For in vivo experiments, nilotinib was prepared in a suspension with 0.5% methylcellulose and 0.5% Tween-80 at a concentration of 10 mg/mL, and mice were treated with 100 mg/kg once daily via oral gavage.

Bronchoalveolar Lavage Preparation and Assays.

Bronchoalveolar lavage (BAL) fluid was collected immediately after euthanasia three days after exposure to S. aureus as previously described (Suliman H B. et al. (2017) Lung cellular and molecular physiology 313(4):L699-L709). Bilateral BAL was performed using two 1ml aliquots of sterile PBS with approximately 75-80% retrieval per mouse. 50 μl cellular BAL fluid was stained with trypan blue, and the total cell count (not including red blood cells) was manually obtained using a Neubauer hemocytometer. The remaining BAL fluid was centrifuged to remove cellular debris, and the total protein concentration was quantified. CFU loads were measured by plating 50 μL of isolated BAL fluid or homogenized lung sample into 10-cm cell culture plates with trypticase soy agar (VWR-90005-052) overnight. Biomarker analysis was performed as directed using the Essential Th1/Th2 Cytokine 6-Plex Mouse ProcartaPlex Kit (Thermo Fisher EPX060-20831-901).

Preparation of Lung Tissue Sections.

Mice were euthanized at days 0, 1, 3, 7, and 30 following exposure to S. aureus. The aorta was dissected to reduce intravascular blood volume, and the lungs were exposed through an incision across the diaphragm and the bottom half of the sternum. The trachea was exposed and cannulated with a sterile 22-gauge Abbocath-T catheter to inflation fix the mouse lungs. Fixation with 4% paraformaldehyde solution in PBS was performed for 15 minutes at room temperature by suspending fixation solution in an apparatus 40 cm above the mice. The entire mediastinum including the trachea, lungs, and heart were then carefully excised and immediately placed in 4% paraformaldehyde for 4 hours on a rotator at 4° C. The left lungs were paraffin embedded at the Duke University Immunohistopathology Core Facility and cut to 5 μm thick sections. The right lungs were sucrose protected, frozen in Optimal Cutting Temperature (OCT) compound at −80° C., and cut into 5 μm thick sections.

Hematoxylin and Eosin Staining and Quantification.

Tissue sections were deparaffinized, rehydrated, and incubated with hematoxylin staining reagent for 10 minutes followed by treatment of acid alcohol, Scott's water, and an eosin secondary counter-stain for 1 minute each. Slides were cleared by xylene, mounted with mounting medium, and analyzed on a Zeiss Axio Imager upright microscope using a 10× objective. Entire left lung coronal sections at approximately the same depth were obtained for each mouse under each experimental condition. Lung sections were imaged and stitched together using the Zeiss Zen software to produce whole left lung images. A baseline measure of cell density was determined using the Histogram function of FIJI software in the group of uninfected mice. Percent infiltration for each mouse exposed to *S. aureus* was measured as the percent decrease in free air space (measured as the decrease in number of pixels with lighter shading using the Histogram function). A one-way ANOVA followed by a post-hoc Tukey test was performed to evaluate the differences in alveolar space infiltration between each group. No image adjustments were applied to H&E images prior to quantification.

Immunofluorescence.

Left lung tissue sections were deparaffinized, rehydrated, and either heat inactivated (BioCare Medical Decloaking Chamber) or treated with 0.05% trypsin for five minutes. Right lung tissue sections were thawed at room temperature for 15 minutes. Both deparaffinized and frozen sections were then washed in PBS and blocked in 3% goat serum in PBS with 0.05% Tween-20 for one hour. Sections were incubated with primary antibodies in blocking solution overnight at 4° C. in a humidified chamber at concentrations indicated below. Sections were then washed with PBS followed by incubation with the appropriate secondary antibody in blocking solution for one hour at room temperature. Sections were then washed with PBS, incubated with the nuclear stain, Hoechst33342, and washed again with PBS before mounting using aqueous mounting media (Dako-S3025).

Quantification of Immunofluorescence Experiments.

All cell counts were evaluated for entire left lung sections using a 10× objective on the Zeiss AxioImager microscope with Zen software at the Duke Light Microscope Core Facility. Cell counts were validated, and representative high-resolution images were taken using 40× and 100× objectives on the Leica SP8 confocal microscope. Stitched images were quantified using the Analyze Particle feature in Fiji software to determine total cell counts across the entire lung for each mouse (>100,000 cells counted per section). Alveolar size (area) was used as a quantitative measure of alveolar damage, and particle analysis was performed on RAGE-stained sections to determine average alveolar size over the entire lung. No image adjustments were applied to 10× objective stitched images prior to quantification. For the representative high-resolution images shown, linear scale adjustments were applied to GFP, CC10, Ki67, SPC, and RAGE antibody stains.

Antibodies.

Antibodies for immunofluorescence experiments included: Anti-SPC (Millipore-AB3786) at a 1:1000 dilution, anti-GFP (Aves Labs-GFP-1020) at a 1:1000 dilution, anti-CCSP (SCGB1A1; CC10) (Millipore-07623) at a 1:500 dilution, anti-RAGE (R&D-MAB 1179), and anti-Ki67 (Abcam-ab16667) at a 1:500 dilution. Antibodies for Western blot analysis included: ABL1 (BD-554148), ABL2 (Santa Cruz-sc134268), and α-tubulin (Millipore-05829). Secondary antibodies with fluorescent labels were purchased from ThermoFisher (anti-mouse and anti-rabbit Alexa Fluors 488, 561, and 647) and used at 1:1000 dilutions. Secondary antibodies with HRP tags were purchased from Jackson Laboratory and used at 1:2000 dilutions.

FACS Sorting/Analysis.

Mice were euthanized 24 and 72 hours after *S. aureus* infection, and lungs were immediately harvested, cut into small pieces with scissors, and digested for 30 minutes at 37° C. using 3 mL per lung of DMEM-F12 medium containing the enzymes: Type I collagenase (450U/mL), elastase (4U/mL), dispase (5U/mL), DNase I (0.33U/mL). Enzymes were neutralized in DMEM-F12 medium with 10% fetal bovine serum. Cells were then centrifuged, resuspended, and filtered through 70 μm and 30 μm cell strainers. Red blood cells were lysed using a lysis buffer (ThermoFisher-00433357). Cells were resuspended in DMEM-F12 medium in 2% bovine serum albumin and treated with propidium iodide prior to FACS sorting using a BD-DiVa system at the Duke Flow Cytometry Core Facility. RNA was collected from isolated GFP-labeled cells using an RNA isolation kit (GE-25050071), and samples were prepared for real-time RT-qPCR as described above. For FACS analysis, following resuspension in DMEM-F12 in 2% BSA, cells were incubated for 5 minutes with an FcγRIII block (BD-53141), washed with DMEM-F12 in 2% BSA, and incubated with the appropriate antibodies: FITC anti-mouse CD45 (BioLegend-147709), PE anti-mouse Ly6G (BioLegend12-5931-81), and FITC anti-mouse F4/80 (BioLegend-53-4801-82), FITC CD3 (BioLegend-555274). Cells were washed twice with DMEM-F12 in 2% BSA and analyzed using the BD Fortessa X-20 at the Duke Flow Cytometry core facility. Data analysis was performed on FlowJo V10. Edu incorporation was assessed as directed using a Click-iT Edu Pacific Blue Flow Cytometry Assay Kit (Thermo Fisher C10418).

TRAP Experiments.

Homozygous L10a-eGFP mice were crossed with CC10-CreERT; Abl1$^{fl/fl}$ mice. Only mice heterozygous for L10a-eGFP were used for experiments. Pulldown of RNA from GFP-labeled ribosomes was performed as previously described (Heiman M, et al. (2014) Nature protocols 9(6): 1282-1291). Briefly, anti-eGFP antibody (19C8 clone from Antibody & Bioresource Core Facility, MSKCC) was coupled to beads using the Invitrogen Dynameads Antibody Coupling Kit using 10 μg purified antibody/mg beads for three days at 4° C. on a rotator. Beads were washed three times in 0.15M KCl and resuspended in 0.15M KCl with 30 mM DHPC. Lung tissue was harvested from mice three days after infection with *S. aureus* and dissociated for five seconds at the lowest setting of a tissue homogenizer (OmniKit Homogenizing Kit) in homogenization buffer (20 mM HEPES-JOH, 150 mM KCl, 4 mM MgCl$_2$, protease inhibitors, 0.5 mM DTT, RNase inhibitor, 100 μg/ml cycloheximide). Lysate was centrifuged, and the supernatant was incubated in 1% Ipegal CA-630 and 30 mM DHPC on ice for five minutes. The mixture was centrifuged and incubated with the prepared beads for one hour at 4° C. on a rotator. Beads were washed five times with 0.35M KCl and eluted with water. RNA isolation and real-time RT-qPCR was performed as described above.

Statistical Analysis.

The number of animals in each group is indicated in the figures and/or figure legends. Differences among groups for immunofluorescence and H&E experiments were assessed using one-way ANOVA followed by post-hoc Tukey tests. All quantification for these experiments was performed using stitched images for the entire left lung (>100,000 cells counted per image). Representative high-resolution images from each animal group are indicated in the figures. Results are presented as means+/−standard error of measurement. BAL experiments were analyzed using a repeated measure MANOVA followed by post-hoc PLSD testing to account for difference in variance between cell count, protein, and LDH data collected from each animal. Individual group testing was performed only when statistical significance was achieved from the ANOVA and MANOVA. All quantification for these experiments was performed using fluid from both the right and left lungs from each animal. For the human bronchial epithelial cell experiments, cells from three non-smoker donors were used. Real-time RT-qPCR experiments were all performed in duplicate or triplicate in two or three separate mice or human patient samples. "*", "", and "*" indicate p-values, <0.05, <0.01, and <0.001, respectively. Bar graphs represent means with standard errors of measurement.

Figure 1C:
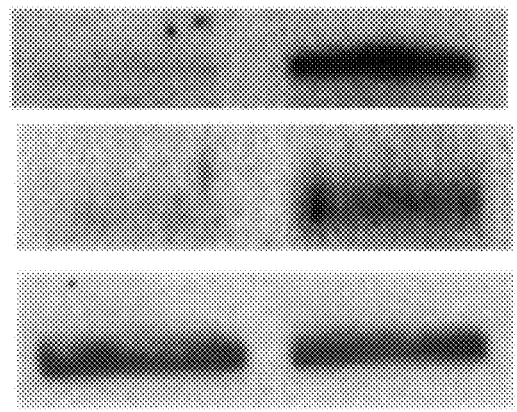

Example 1: Abl Kinases are Upregulated in Lung Epithelial Cells Following Injury To evaluate whether Abl kinases play a role in lung epithelial cell integrity during regeneration and/or repair, Abl expression was assessed in primary human bronchial epithelial cells (HBEC) grown in air-liquid interface (ALI) cultures before and after pathogen-induced injury. HBECs were grown in ALI cultures for 28 days to induce differentiation of basal cells to a pseudostratified layer of basal, secretory, and ciliated epithelial cells. At day 28, HBECs were incubated with *S. aureus* and then harvested one and five days after bacterial inoculation to evaluate Abl kinase RNA and protein expression (FIG. 1A). A 20 to 30-fold increase in Abl1 was observed, and to a lesser extent Abl2, transcripts at 24 hours that persisted up to five days following exposure to bacteria (FIG. 1B). Abl protein expression was similarly enhanced after pathogen exposure (FIG. 1C). Previous reports have shown that enhanced Abl kinase activity is associated with a wide variety of pathologies including endothelial barrier dysfunction, tumorigenesis, and inflammation. Thus, Abl kinase inhibition may affect the response of lung epithelial cells during injury, regeneration, and/or repair.

Figure 1D:
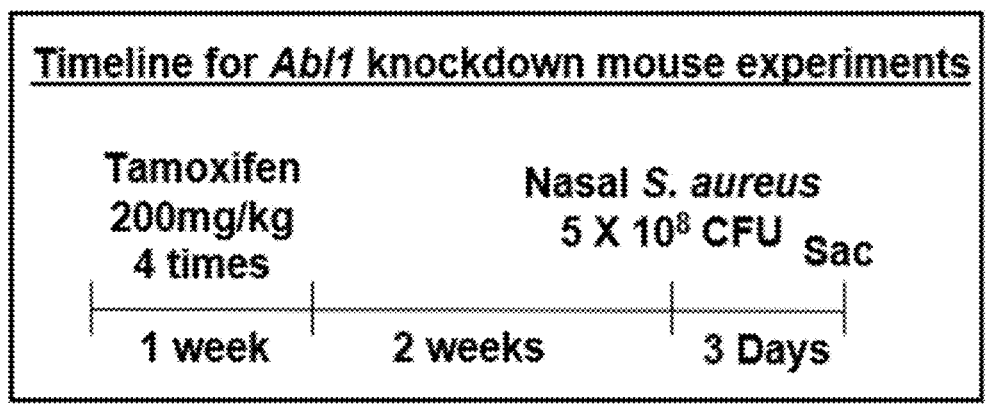
Figure 1E:
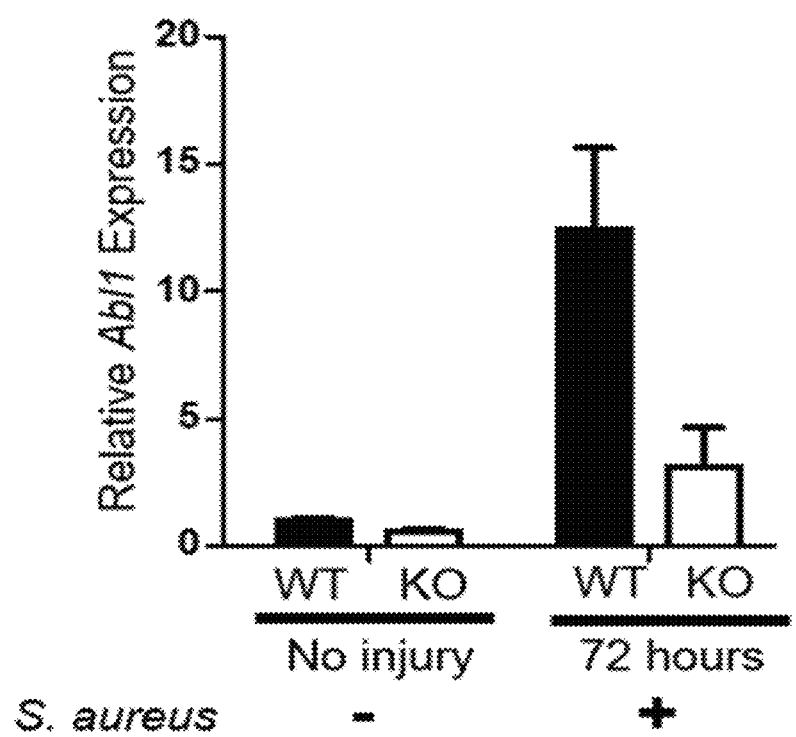

Example 2: Loss of Abl1 in SCGB1A1+ Lung Epithelial Cells Promotes Accelerated Recovery in a Mouse Model of Pneumonia To evaluate whether Abl has a role in regulating the response of bronchial epithelial cells to injury in vivo, a conditional, secretory cell-type specific knockout of Abl1 was generated with concomitant expression of a farnesylated GFP (i.e. membrane bound GFP) reporter (CC10 (Scgb1a1)-CreERT; Rosa26-fGFP; Abl1$^{fl/fl}$) upon administration of tamoxifen. Efficient (>75%) excision of Abl1 in Scgb1a1-expressing epithelial cells following intraperitoneal delivery of four doses of tamoxifen two weeks prior to inducing injury was obtained. Scgb1a1, also known as CC10 or CCSP, is widely used as a marker of secretory cells in the mammalian lung airways. To injure the lung epithelium, a mouse model of pneumonia was used induced by intranasal insufflation of 5×10$^8$ CFU *S. aureus* (FIG. 1D). In this model, mice survive the bacterial infection despite significant lung injury accompanied by inflammation and edema. Following infection with *S. aureus*, a >10-fold increase in Abl1 expression in isolated GFP+ (Scgb1a1 driver) cells was observed in wild-type mice that was abrogated in Abl1$^{fl/fl}$ mice (FIG. 1E). Abl1$^{fl/fl}$ mice displayed remarkable recovery from symptoms of infection compared to wild-type mice (FIG. 2A-2C).

Figure 2B:
Figure 2C:
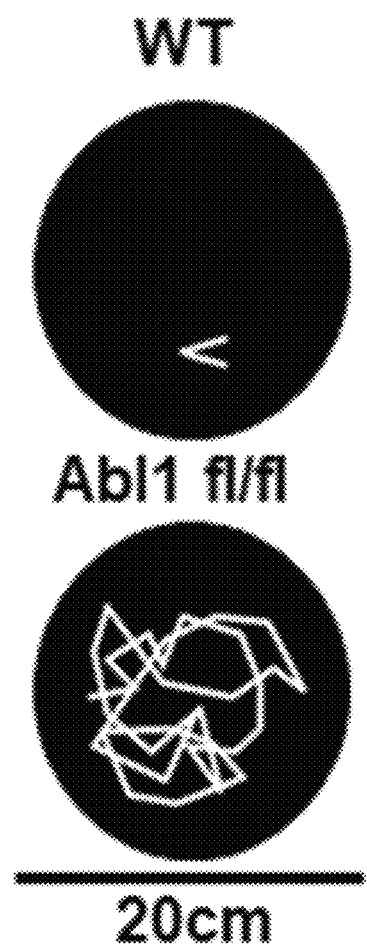

Abl1$^{fl/fl}$ mice were active and lacked pathological signs of infection displayed by wild type mice after *S. aureus* inoculation (a screenshot of a 30-second video corresponding to FIG. 2B; two-minute tracing of mouse movement in FIG. 2C).

Figure 2D:
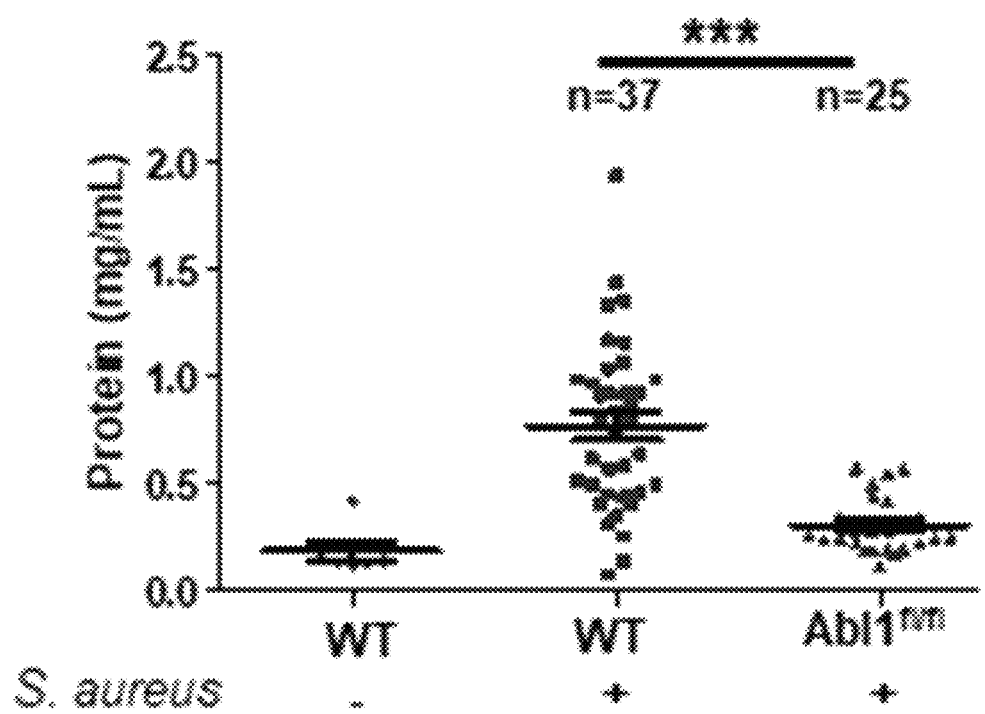
Figure 2E:
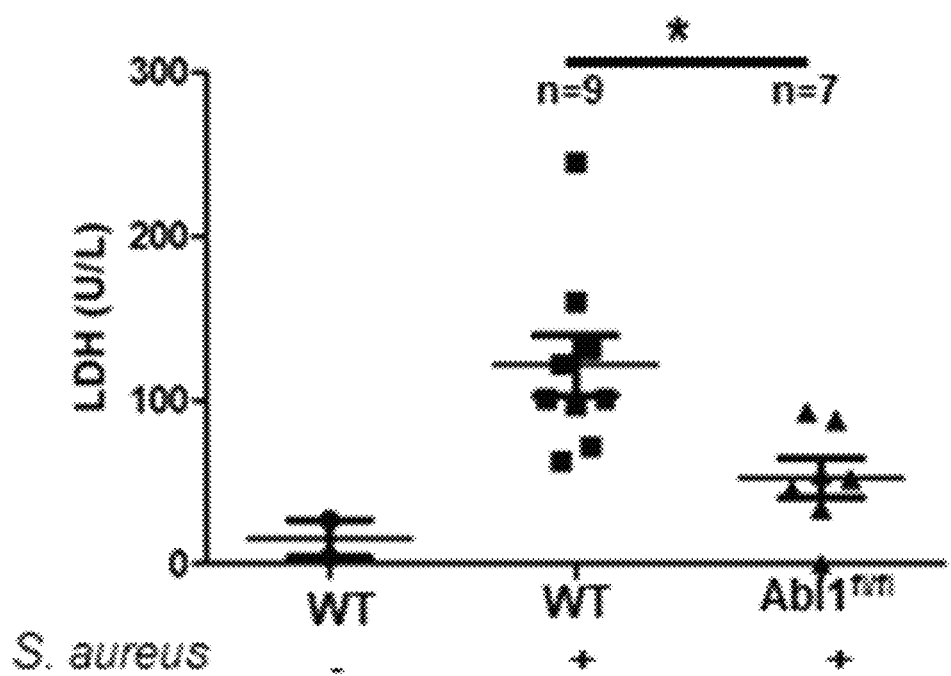
Figure 2F:
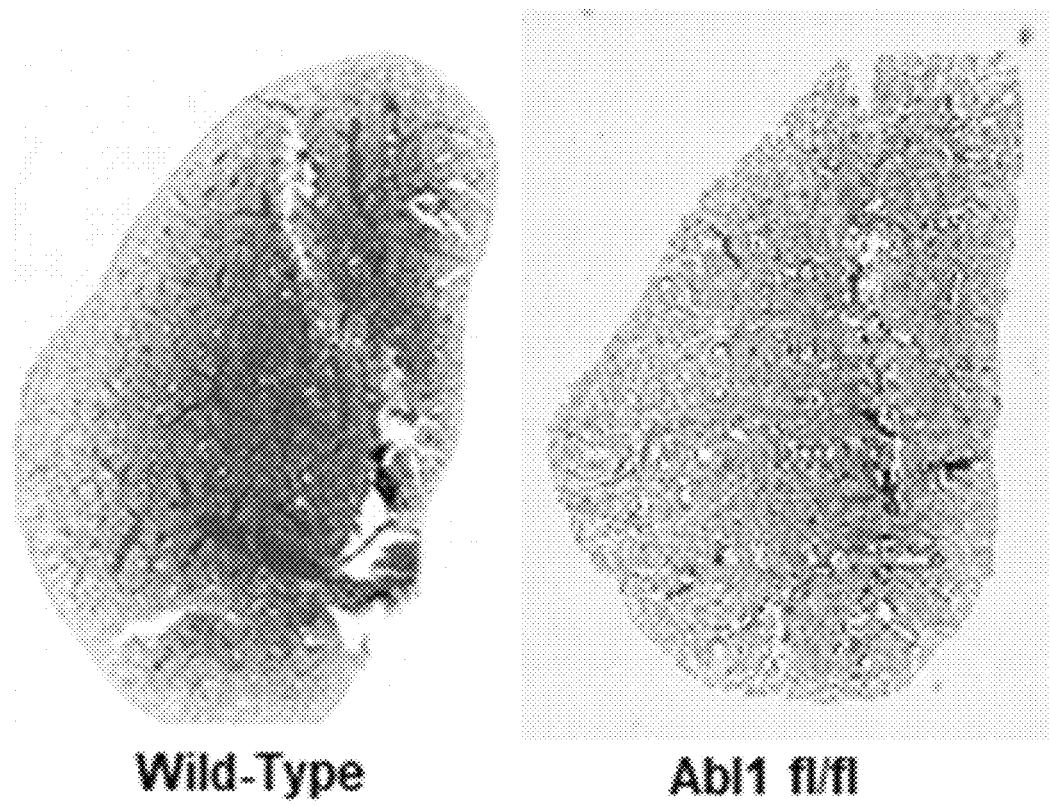
Figure 2G:
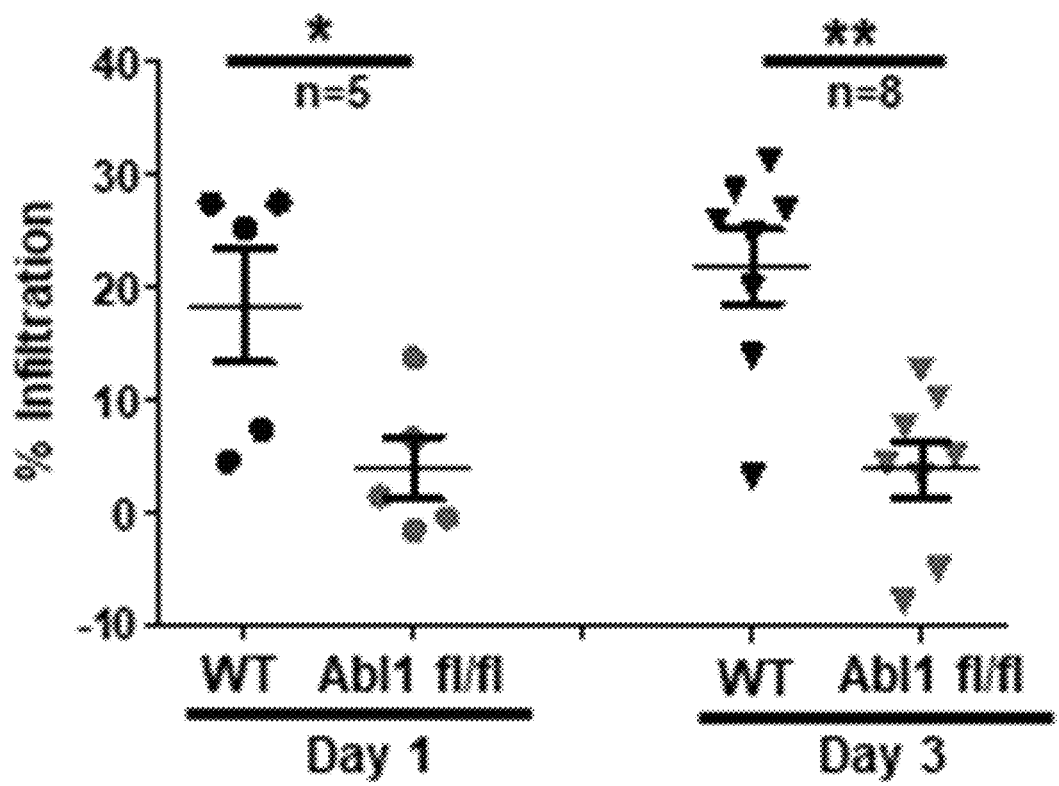
Figure 3A:
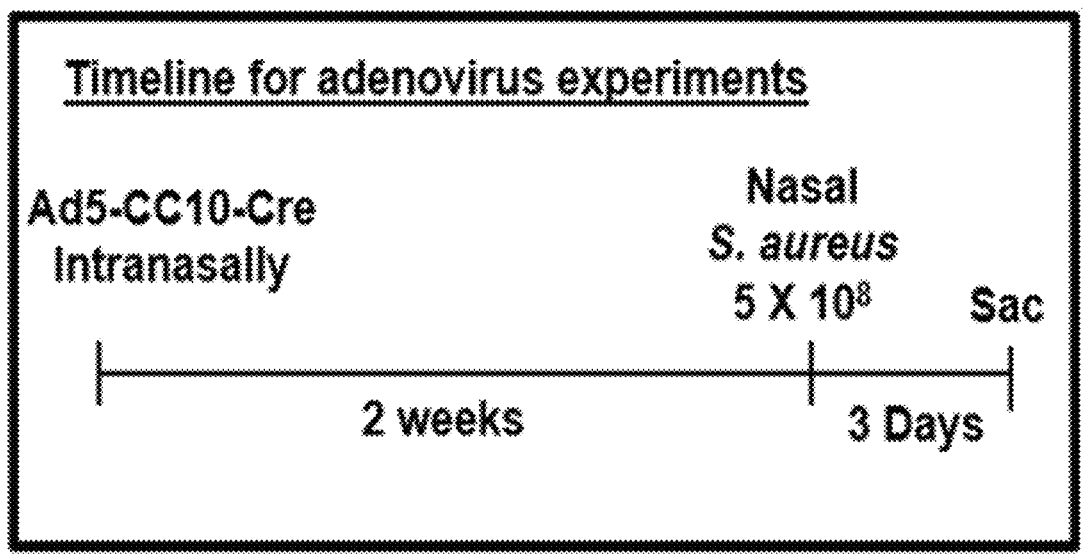
FIGS. 3A-3B show tamoxifen and adenoviral mediated excision of $Abl1^{fl/fl}$ mice results in reduced lung injury compared to wild-type mice 72 hours following nasal insufflation of $S.$ $aureus$.
Figure 3B:
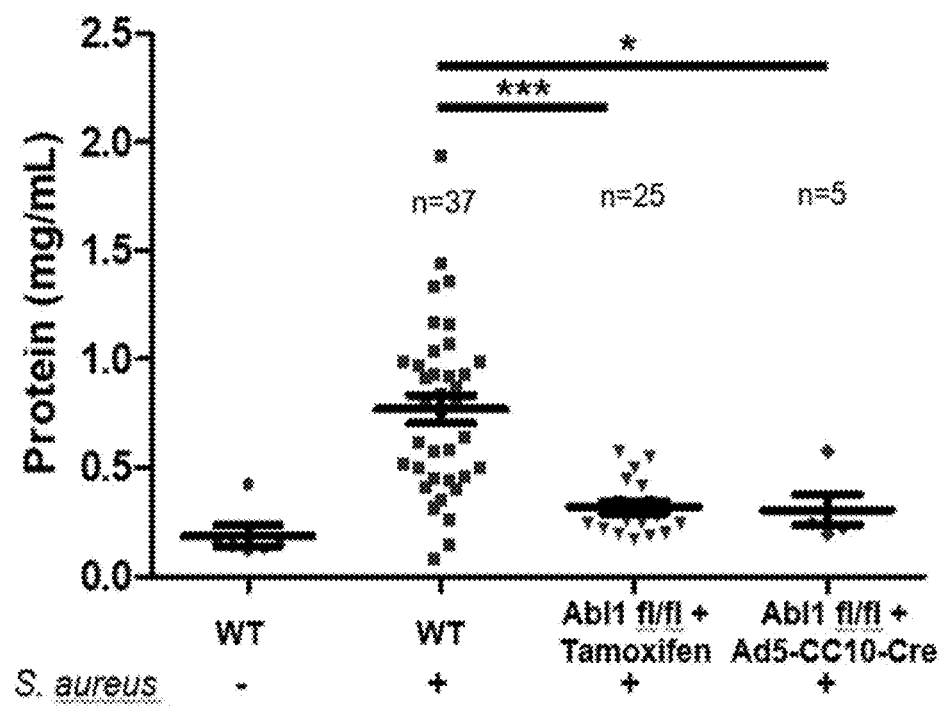

Bronchioalveolar lavage (BAL) samples from mouse lungs three days after exposure to *S. aureus* showed a significant decrease in protein (FIG. 2D), the cell damage marker, LDH, (FIG. 2E), and leukocytes in Abl1$^{fl/fl}$ compared to wild-type mice. Abl1 knockout mice also exhibited significantly diminished injury in lung tissue sections 72 hours after injury (FIG. 2F and FIG. 2G). Similar results were observed in Abl1$^{fl/fl}$ mice treated with an adenoviral vector encoding a CC10 (Scgb1a1) promoter driving the expression of Cre-recombinase (Ad5-CC10-Cre) to induce excision of the floxed locus in the Abl1$^{fl/fl}$ mouse (FIG. 3A-3B). Of note, all wild-type mice shown were treated with tamoxifen, and evaluation of tamoxifen treated wild-type mice versus untreated wild-type mice showed no significant differences in the degree of lung injury.

Figure 4A:
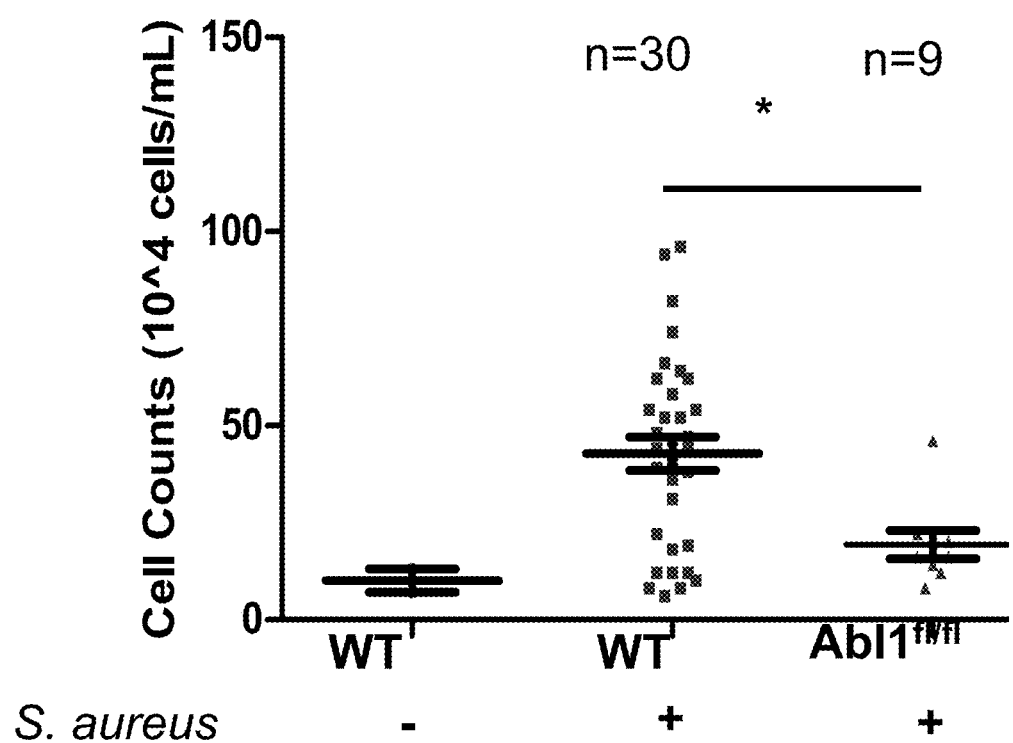
FIGS. 4A-4E show loss of Abl kinases in Scgb1a1+ lung epithelial cells reduces immune cell infiltration in the alveoli without affecting immune cell influx in the lung parenchyma following $S.$ $aureus$ induced lung injury.
Figure 4B:
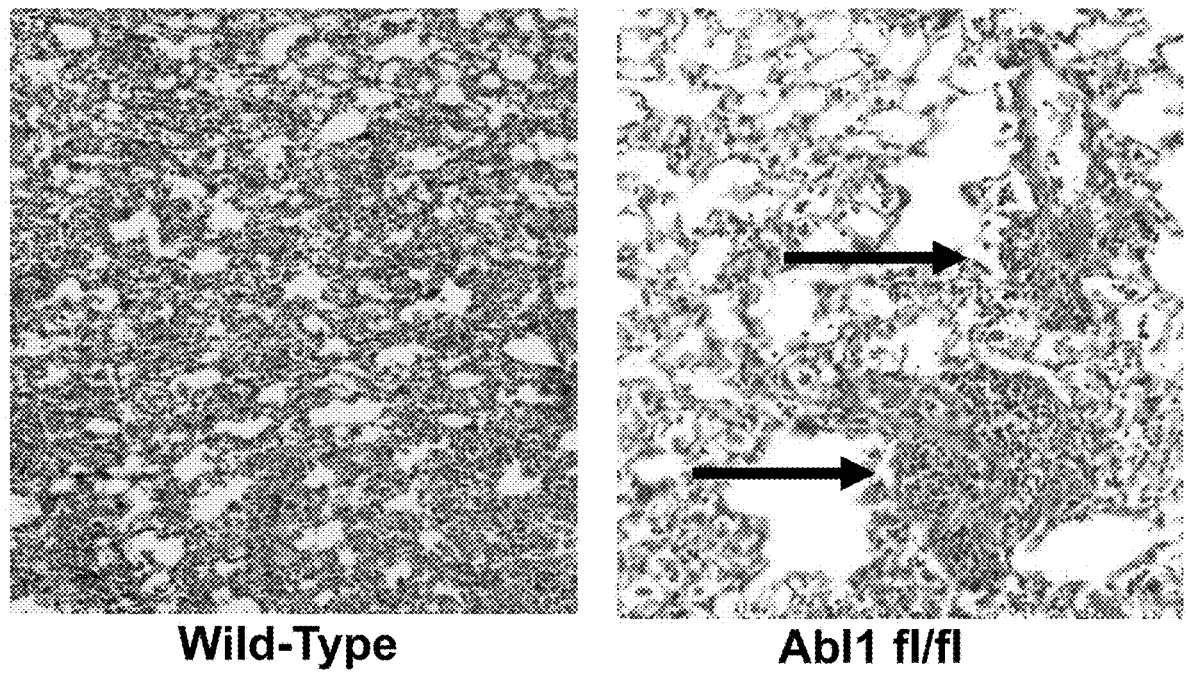
Figure 4C:
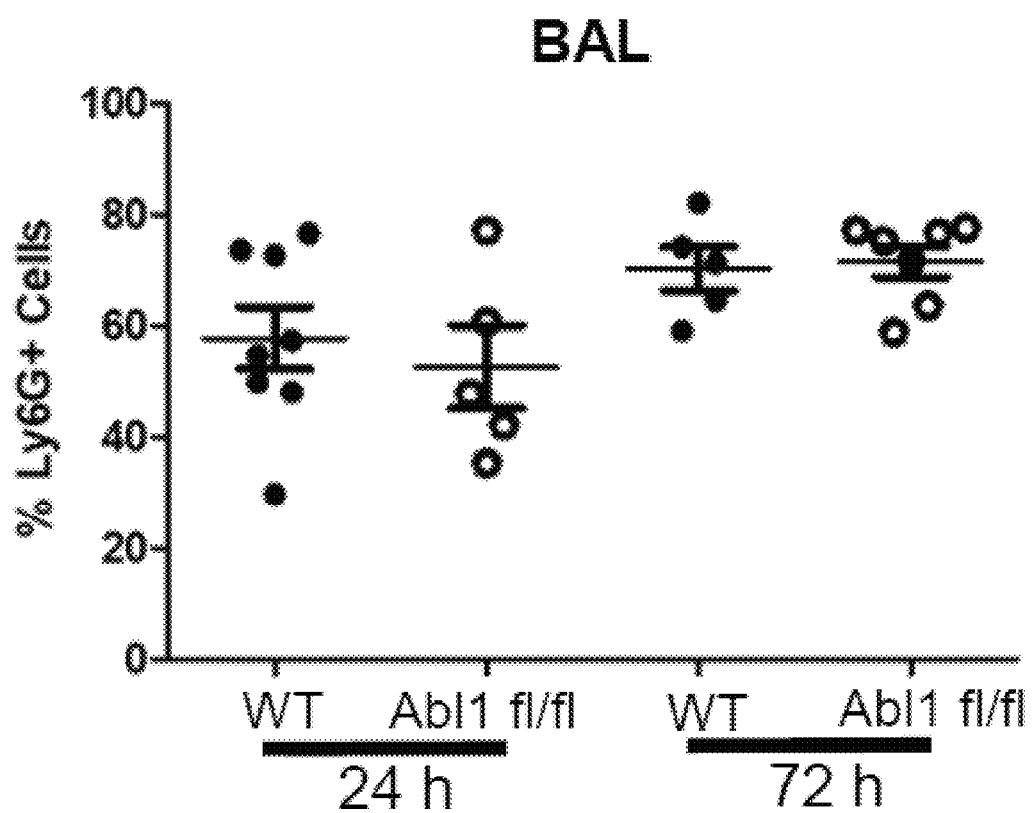
Figure 4D:
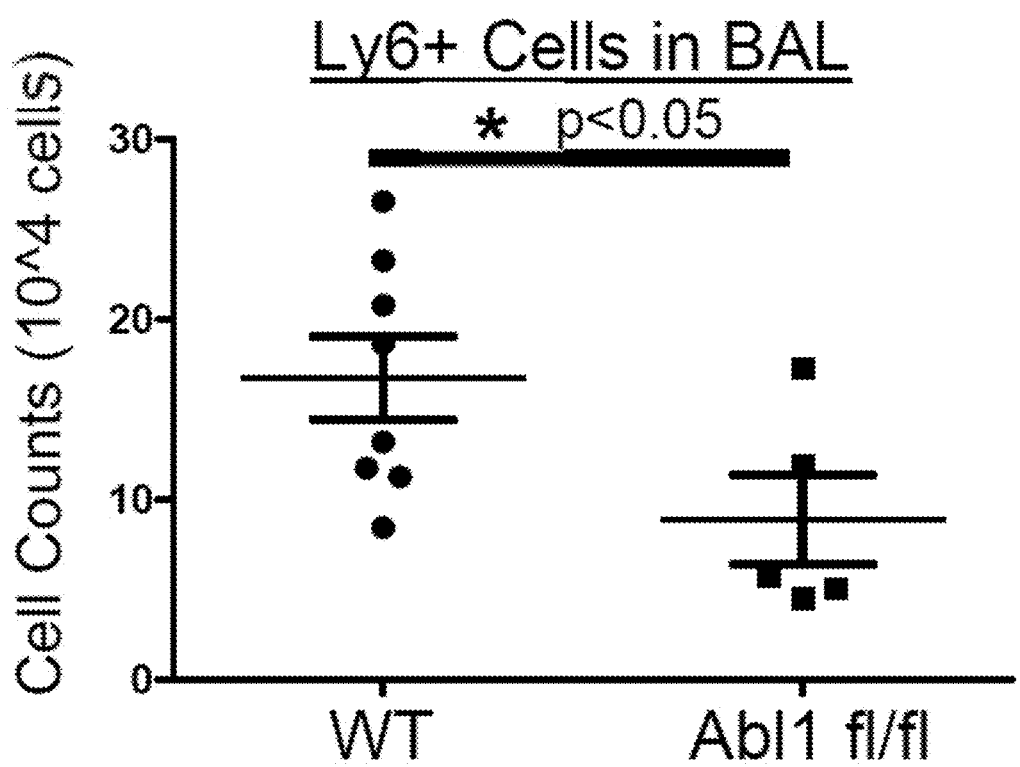
Figure 4E:
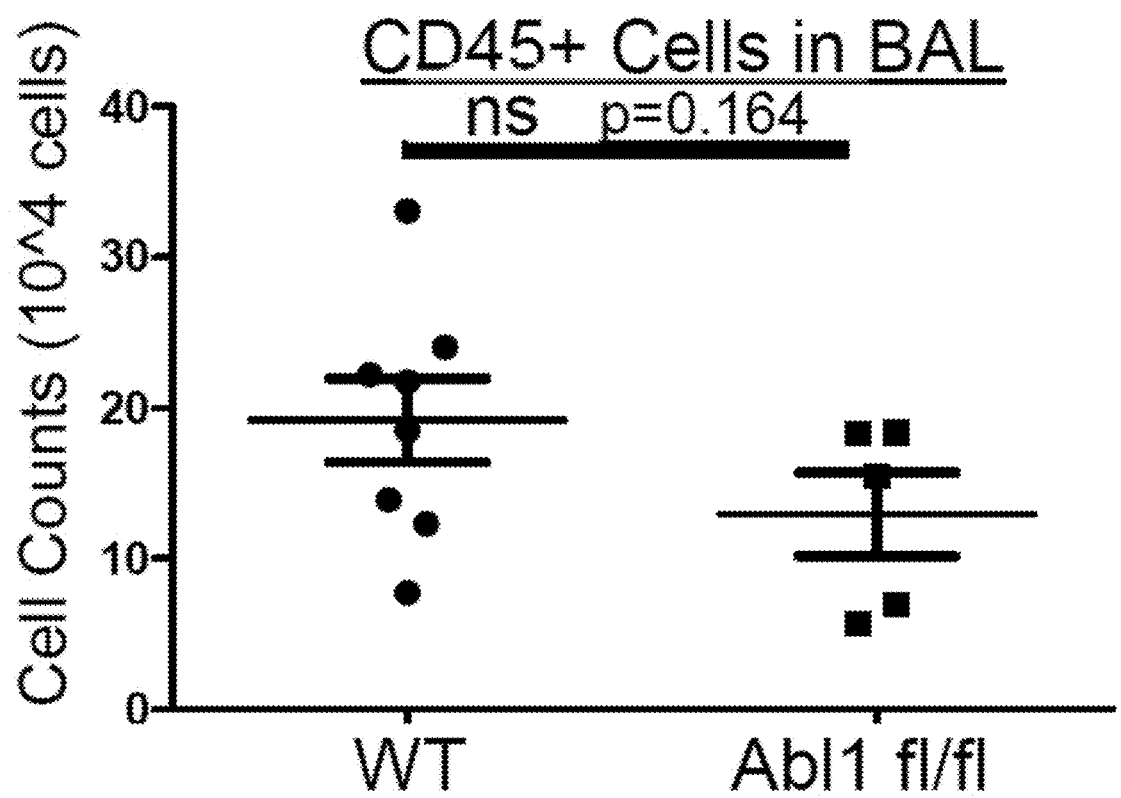
Figure 5A:
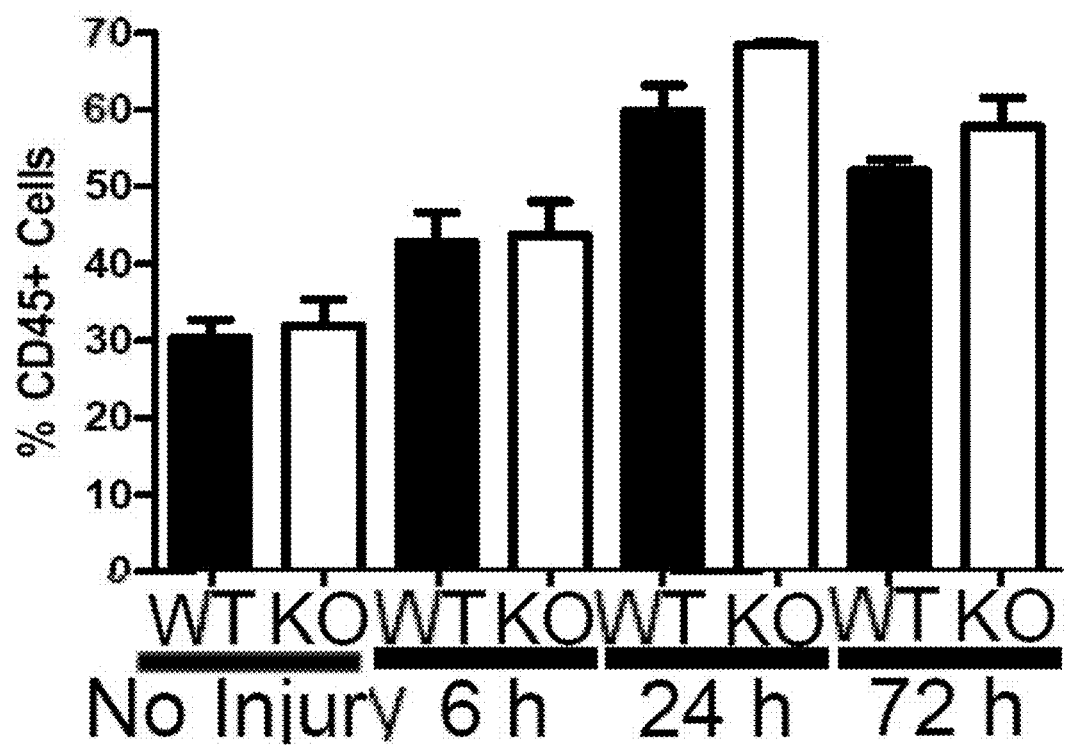
FIGS. 5A-5E show loss of Abl1 in Scgb1a1+ lung epithelial cells does not confer differential susceptibility to *S. aureus* infection or immune cell response in the lung parenchyma compared to wild-type mice.
Figure 5B:
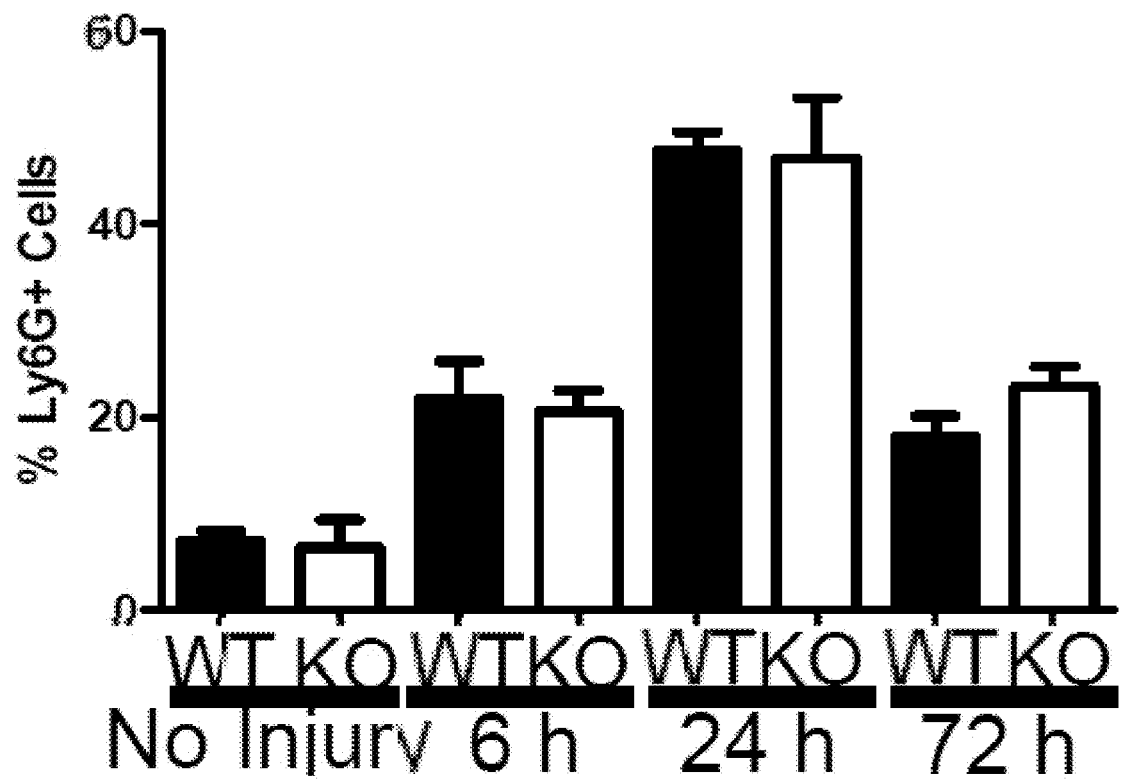
Figure 5C:
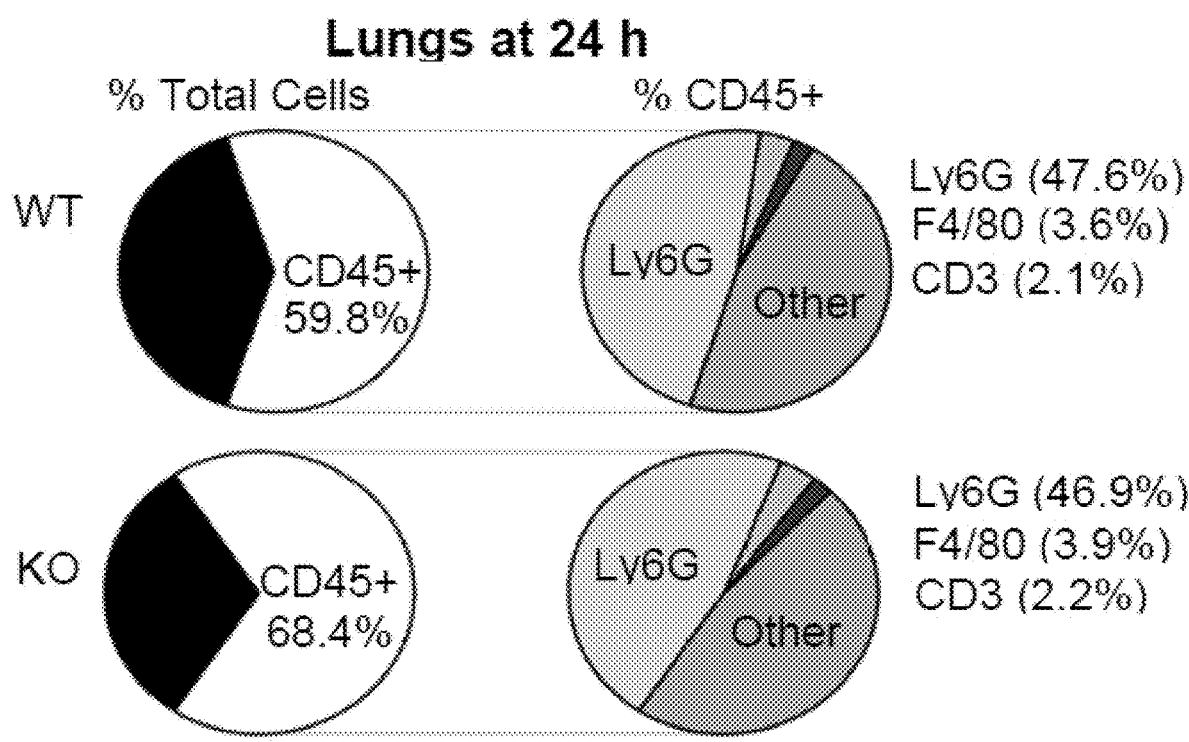

Given the reduction in immune cell infiltration in the alveolar space detected in BAL fluid (FIGS. 4A-4E), it was next evaluated whether loss of Abl1 in Scgb1a1-expressing epithelial cells could affect the immune response to *S. aureus* infection. Whether the observed decrease in immune cell infiltration in the BAL fluid of Abl1 knockout mice was specific to the alveolar space or whether there was also a decrease in the influx of immune cells into the lung parenchyma was evaluated. Analysis of H&E sections of lungs from wild-type and Abl1 knockout mice suggested that the reduction in immune cell infiltration was specific to the alveolar space, as a neutrophilic infiltration was observed in the lung parenchyma of both wild-type and Abl1 knockout mice (FIG. 4B). FACS analysis of the BAL fluid showed a decrease in the total immune cell (CD45+) and neutrophil populations (Ly6G+) in the alveolar space, without changes in the proportion of neutrophils in the BAL fluid of Abl1 knockout compared to wild-type mice (FIGS. 4C-4E). Moreover, no changes in the populations of immune cells including neutrophils in the whole lung (non-BAL fluid component) of wild-type and Abl1 knockout mice after injury were found (FIG. 5A-5C). The finding that loss of Abl1 in Scgb1a1+ cells leads to a decrease in leukocytes in the alveolar space only (BAL fluid component) without changing the total immune cell population in the lung (non-BAL fluid component) suggested that loss of Abl1 in Scgb1a1+ epithelial cells protects and/or promotes regeneration of epithelial barrier function following injury, thereby reducing protein and cellular infiltration into the alveolar space, which enhances gas exchange compared to wild-type mice.

Figure 5D:
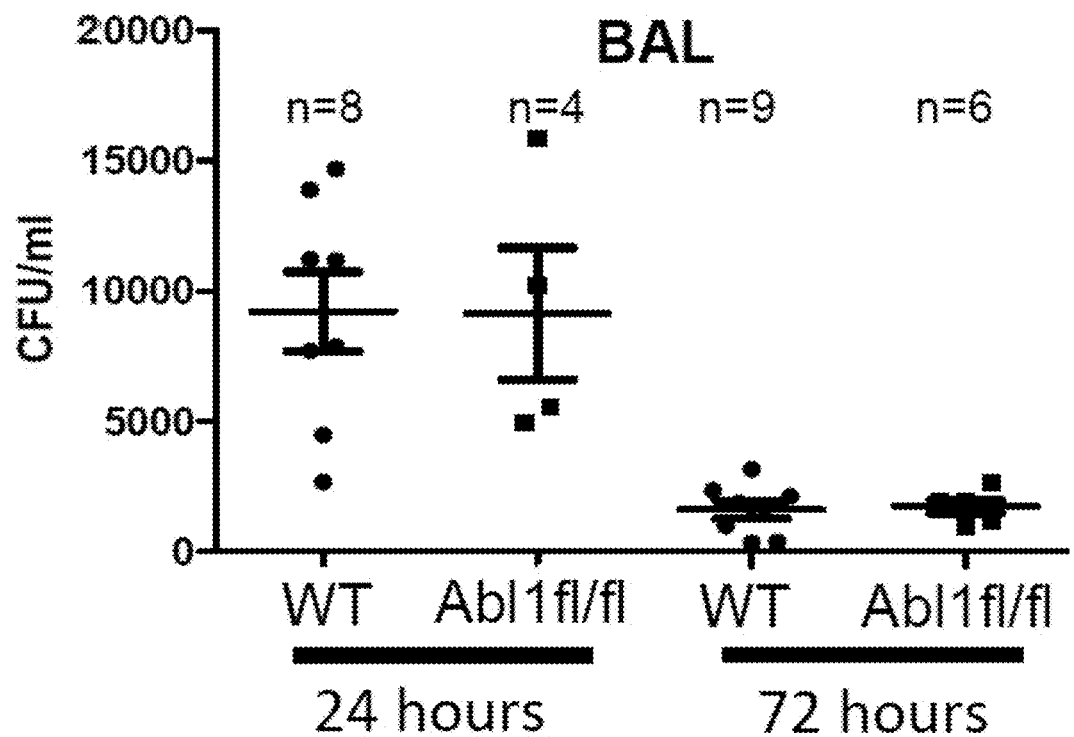
Figure 5E:
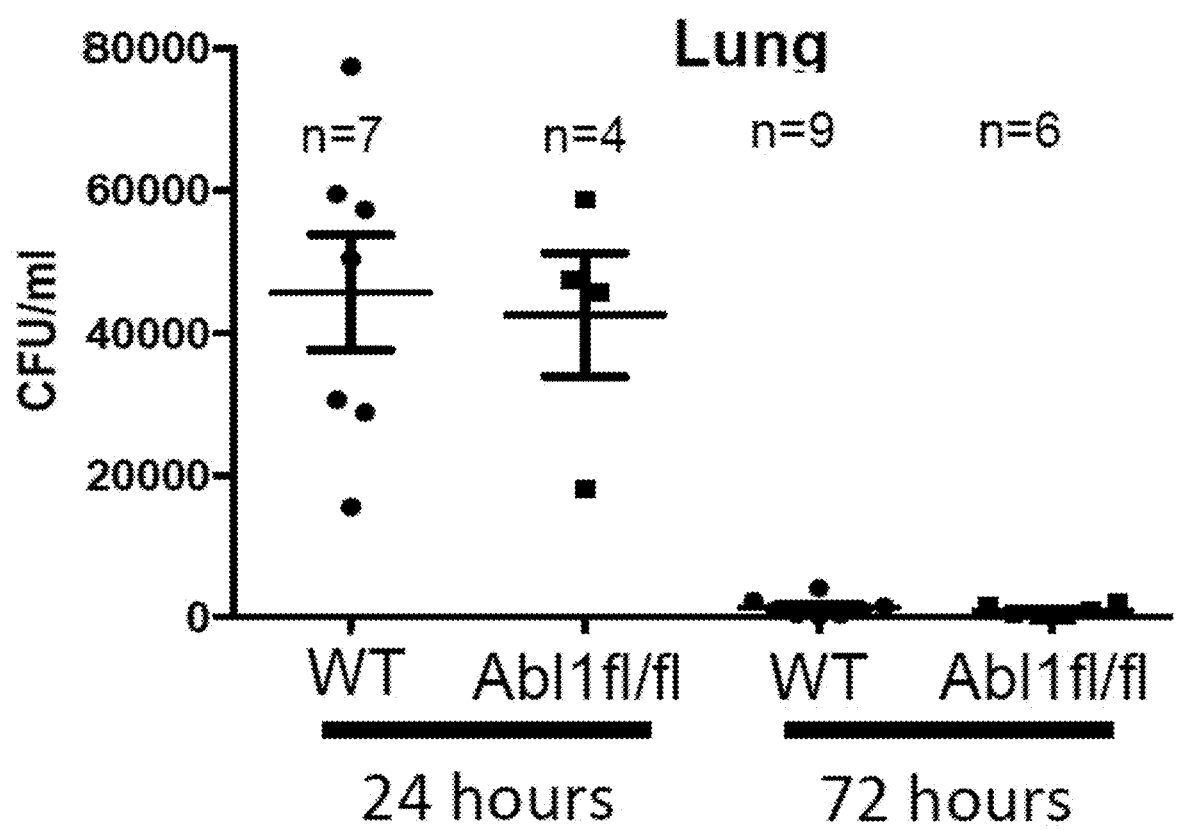
Figure 6A:
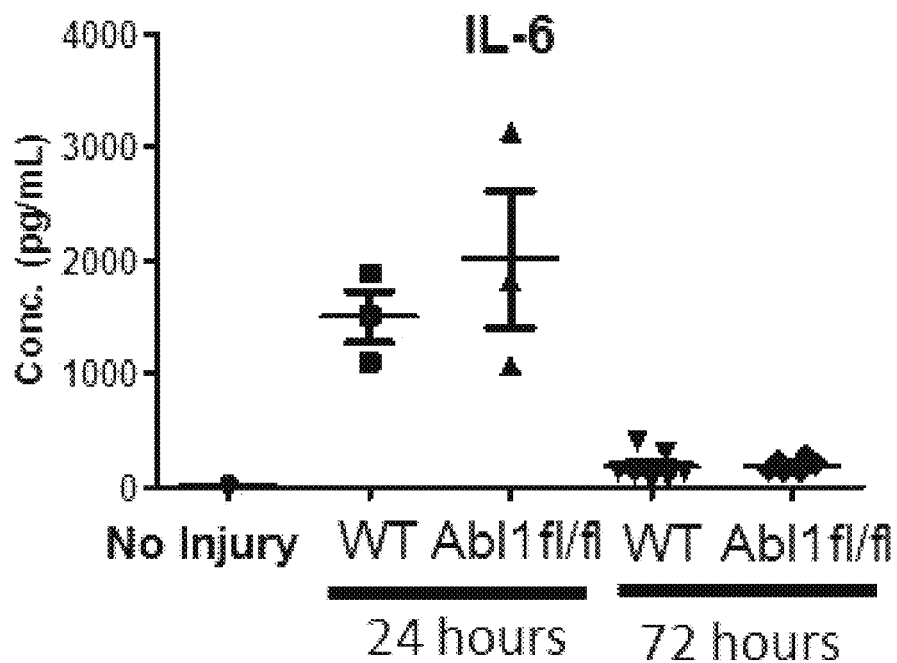
FIG. 6A is a graph of BAL fluid in wild-type and control mice 24 and 72 hours after injury showing no significant change in IL-6production levels.
Figure 6B:
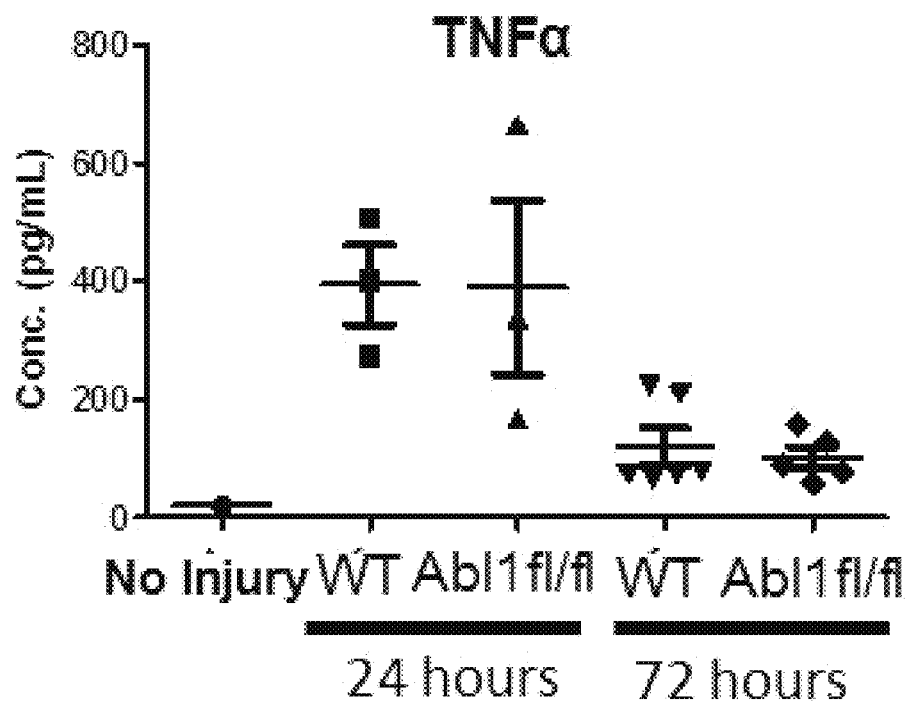
FIG. 6B is a graph of BAL fluid in wild-type and control mice 24 and 72 hours after injury showing no significant change in TNF αproduction levels.

To assess whether loss of Abl1 in the lung epithelium has a protective effect by blocking pathogen infection, whether loss of Abl1 in Scgb1a1+ cells confers differential susceptibility of lung epithelial cells to bacterial infection compared to wild-type mice was evaluated. No significant change in bacterial load in either the alveolar space (BAL fluid component) or the whole lung (non-BAL fluid component) 24 hours and 72 hours after injury were found (FIG. 5D-5E). Additionally, no significant change in cytokine production levels in the BAL fluid 24 and 72 hours after injury was observed (FIG. 6A-6B).

The finding that genetic inactivation of Abl1 in Scgb1a1+ cells promotes recovery from pathogen-induced lung injury in a mouse model of pneumonia without modulating susceptibility to bacterial infection or immune responses suggests that Abl kinases modulate the regeneration response of lung epithelial cells following injury.

Figure 7A:
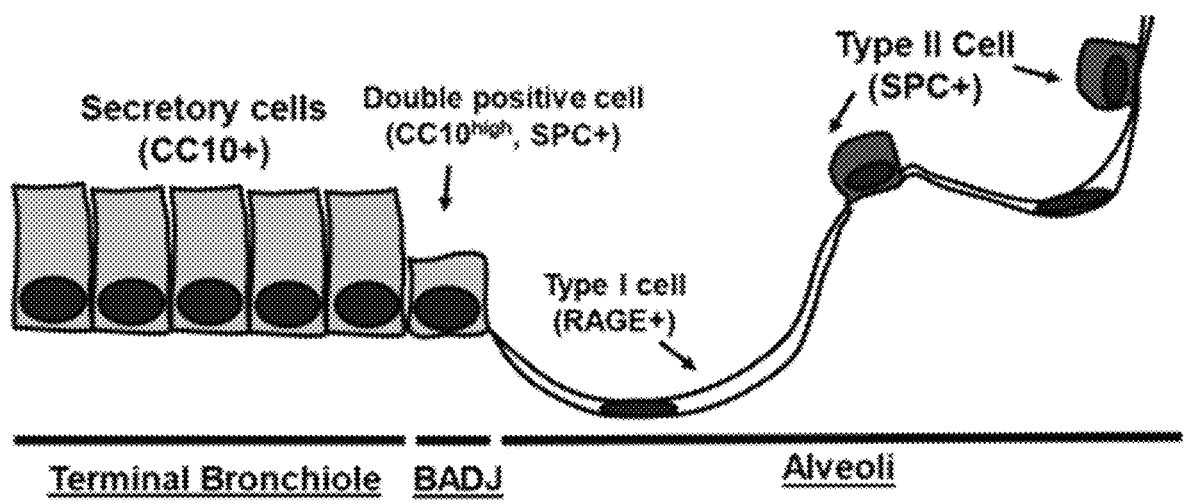
FIGS. 7A-7D show genetic inactivation of Abl1 promotes regeneration of the alveolar epithelium following nasal insufflation of *S. aureus*.
Figure 7B:
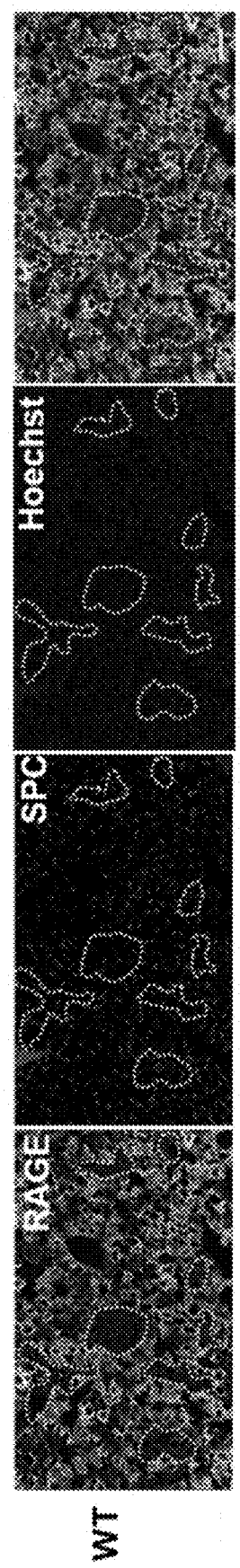

Example 3: Genetic Inactivation of Abl1 in SCGB1A1+ Lung Epithelial Cells Promotes Regeneration of the Alveolar Epithelium after Pathogen-Induced Lung Injury To dissect the cellular effects of Abl kinase inactivation in lung epithelial cells that could explain the enhanced recovery observed following bacterial infection, CC10 (Scgb1a1)-CreERT; Rosa26-fGFP; Abl1$^{fl/fl}$ and the corresponding wild-type, control mice were sacrificed at various times following nasal insufflation of S. aureus. Staining for lung epithelial cell populations (FIG. 7A) revealed that damage following nasal insufflation of S. aureus occurred primarily in Type I alveolar epithelial cells (AECs), identified by immunostaining for the cell-surface marker, RAGE (also known as AGER), without significant changes in the number of Type II AECs (SPC+) and airway epithelial cell types in regions of lung injury (FIG. 7B).

Figure 7C:
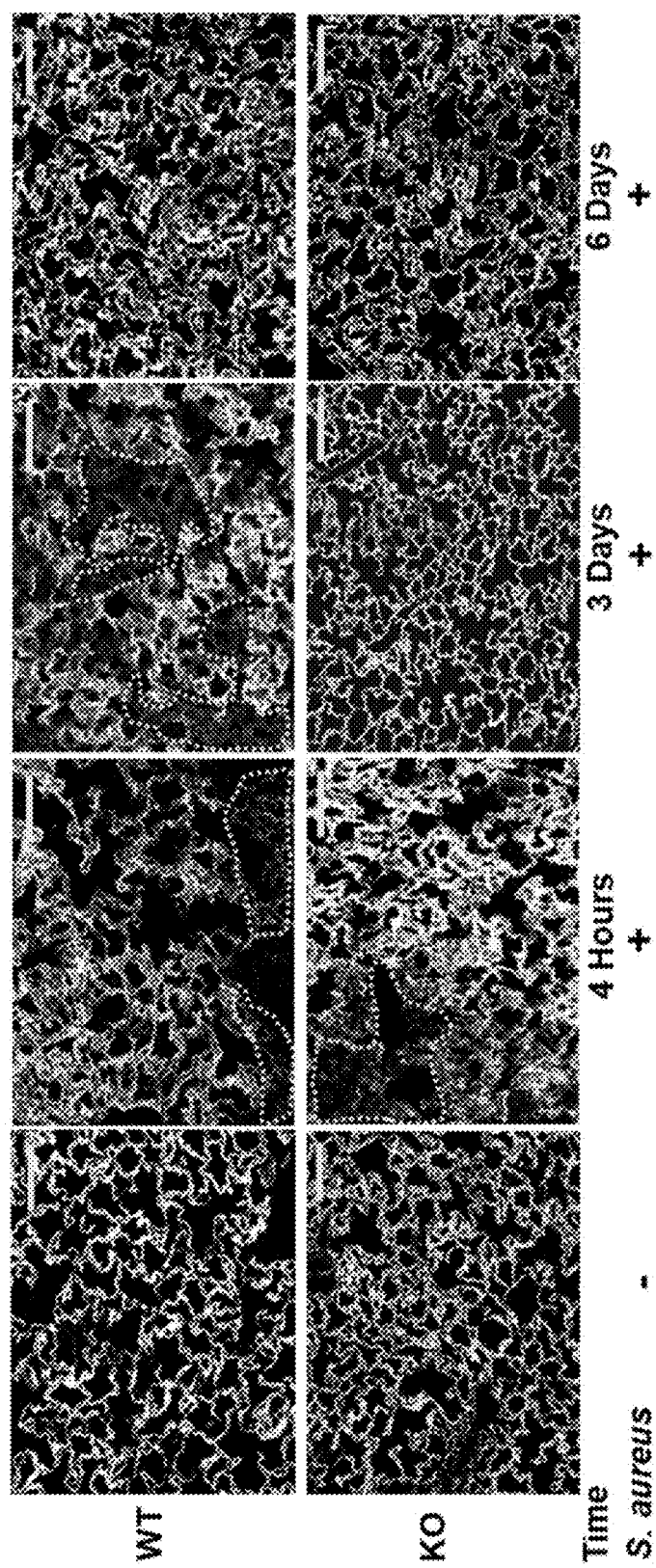
Figure 7D:
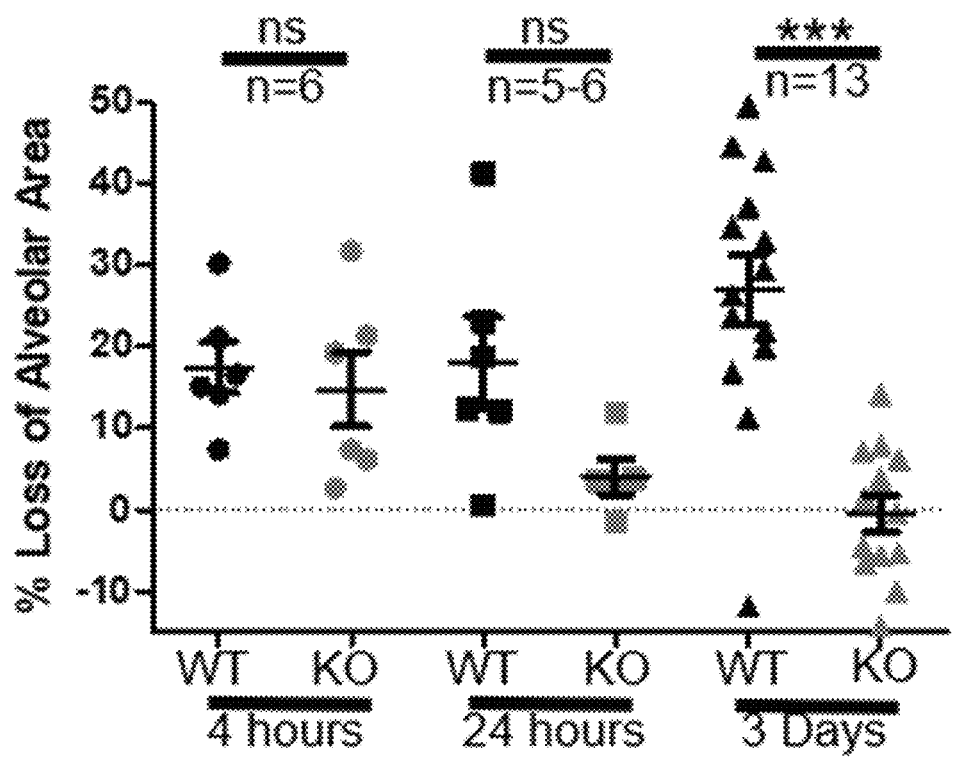

Damage to Type I AECs is maximal at 24-72 hours following S. aureus exposure, with wild-type mice achieving complete recovery by day 6 (FIG. 7C, top). In contrast to wild-type mice, the alveolar epithelium of Abl1$^{fl/fl}$ mice exhibited complete recovery by day 3 post-infection (FIG. 7C, bottom; quantification in FIG. 7D). These findings were surprising because Abl1 was inactivated specifically in Scgb1a1-expressing cells of the airway, and Type I AECs do not express Scgb1a1.

To distinguish between protective or regenerative effects of Abl kinase inhibition, lung tissue isolated at earlier time points after S. aureus exposure was assessed for lung epithelial cell damage. At 4 hours following nasal insufflation of S. aureus, Type I AEC damage, as measured by alveolar volumes, was observed in both wild-type and Abl1 knockout mice (FIG. 7C-7D). These findings suggest that inactivation of Abl signaling in SCGB1A1+ cells fails to prevent pathogen-induced alveolar injury, but rather promotes rapid regeneration of Type I AECs, leading to accelerated recovery of Abl1$^{fl/fl}$ mice following pathogen exposure.

Figure 8A:
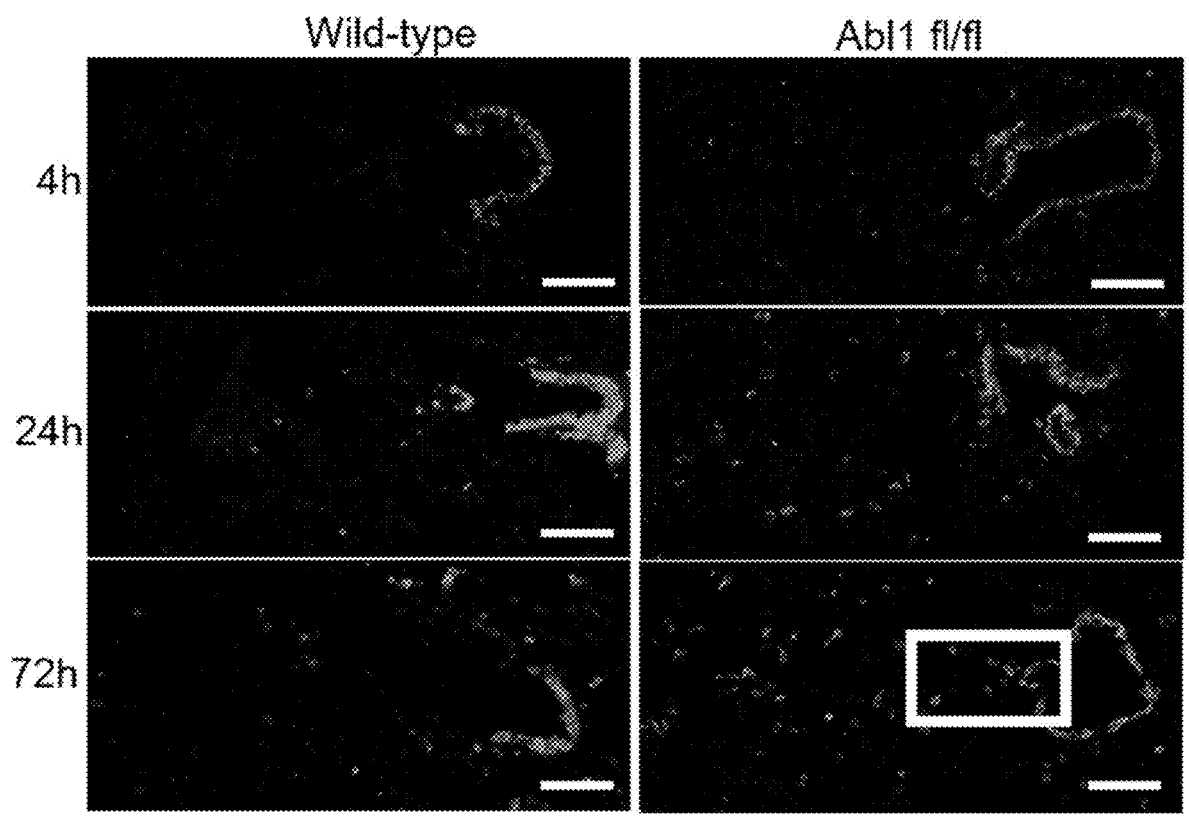
FIGS. 8A-8F show conditional deletion of Abl1 promotes expansion of GFP+ (Scgb1a1 driver) SPC+ cell population in mouse lungs following injury.
Figure 8B:
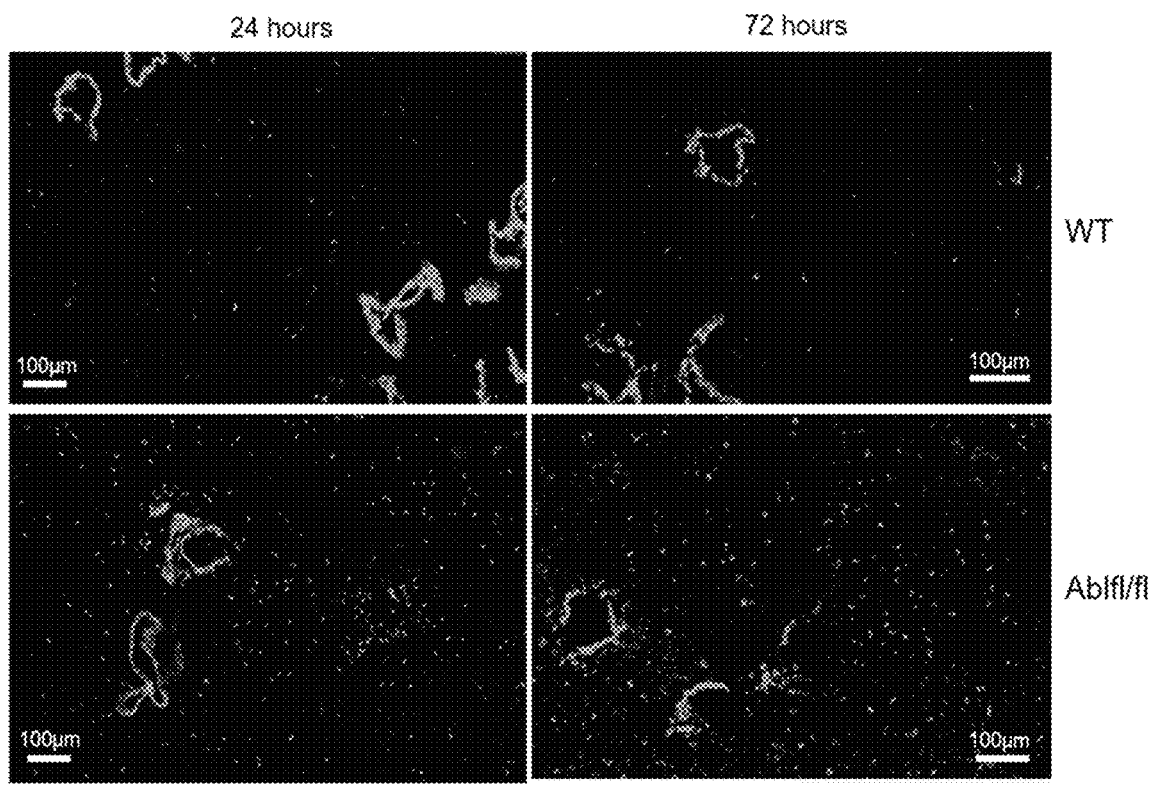

Example 4: Conditional Deletion of Abl1 Promotes Expansion of Double-Positive SCGB1A1+ SPC+ Cell Population Following Injury To dissect the role of Abl1 in Scgb1a1+ cells in the regeneration of the damaged alveolar epithelium following pathogen exposure, lineage tracing experiments of the Scgb1a1+ cell population using a Rosa26-fGFP reporter in CC10 (Scgb1a1)-CreERT mice were performed. A dramatic increase in the number of GFP+ (Scgb1a1 driver) cells in the lung parenchyma of Abl1$^{fl/fl}$ mice compared to wild-type mice 72 hours after injury was detected (FIG. 8A and FIG. 8B).

Figure 8C:
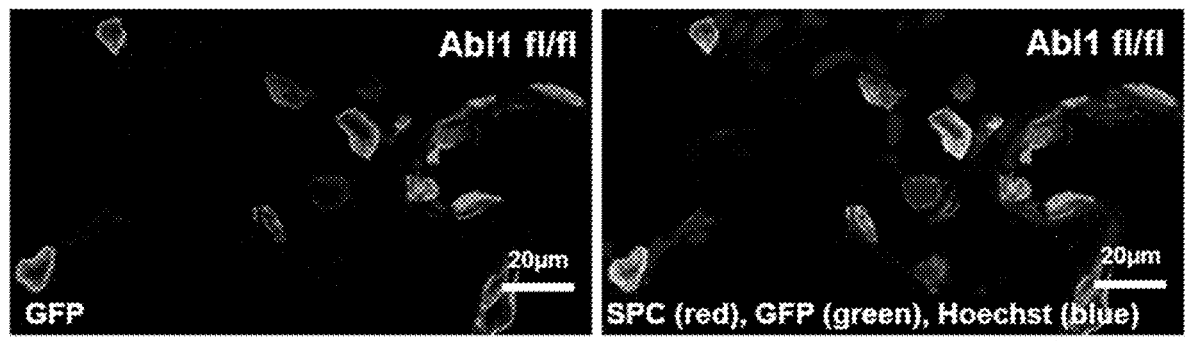
Figure 8D:
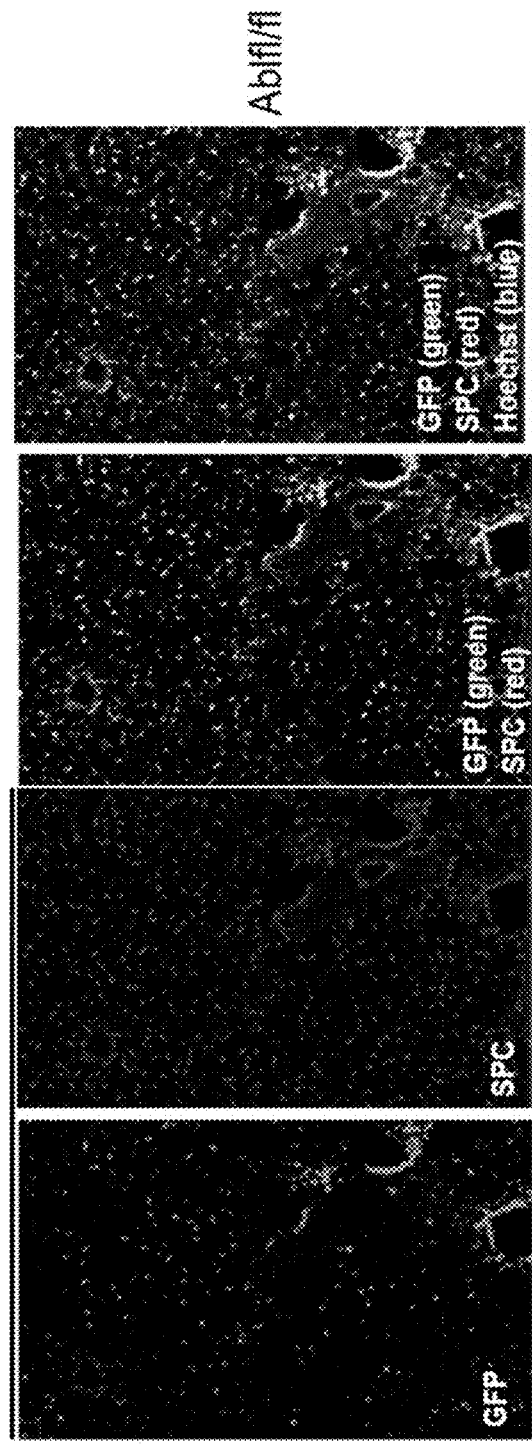
Figure 8E:
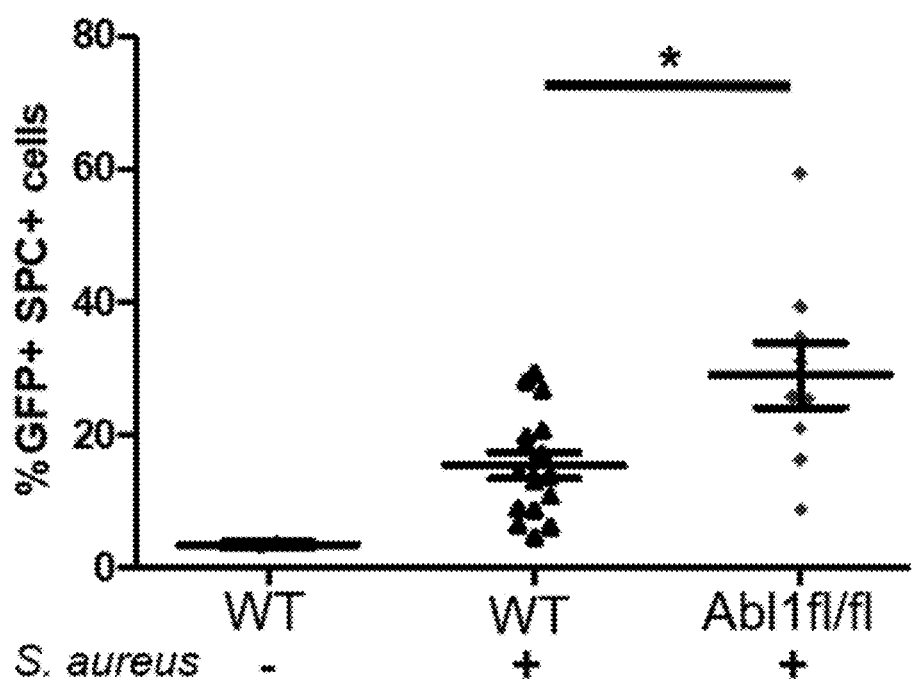

Staining for the Type II AEC marker, Surfactant Protein-C(SPC) encoded by Sftpc, revealed that the GFP+ cells in the alveolar space co-express SPC (FIG. 8C). Following injury, a two-fold increase in the number of GFP+ SPC+ cells in Abl1 knockout compared to wild-type mice was observed. Notably by day 3 after injury, 30% of SPC+ cells in Abl1$^{fl/fl}$ mice were GFP+ and, therefore, lineage-derived from Scgb1a1-expressing cells (FIG. 8D quantification in FIG. 8E).

Importantly, there was no significant difference in the GFP+ SPC+ cell populations in uninfected wild-type versus Abl1$^{fl/fl}$ mice, three weeks and up to four months after delivery of tamoxifen to induce Abl1 excision. CC10-Cre-ERT; Rosa26-fGFP; Abl1$^{wt}$ (wild type) and Abl1$^{fl/fl}$ (knock out) mice were given four doses of tamoxifen. After four months, lungs were harvested, and lung sections were probed with antibodies for GFP and SPC and compared by imaging. There was no significant difference in the observed double-positive GFP+ SPC+ cell population in the alveolar space in these uninfected mice.

Figure 8F:
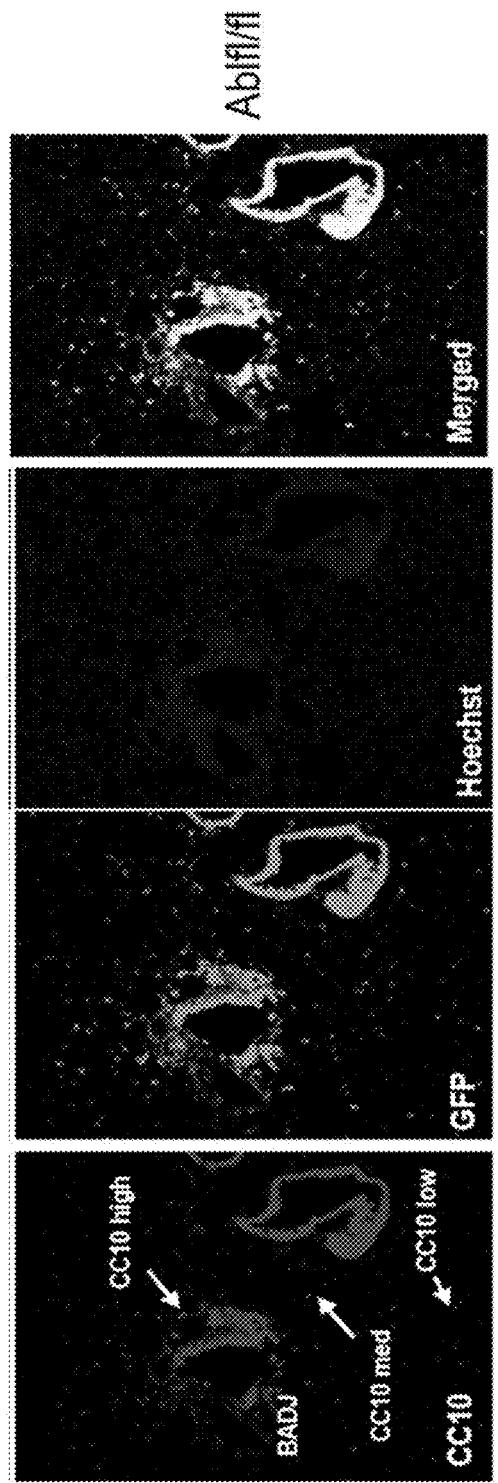

Whether the GFP+ (Scgb1a1 driver) SPC+ cells in the alveolar epithelium retained expression of Scgb1a1 was investigated. Co-staining for GFP and Scgb1a1 showed that GFP+ cells in close proximity to the BADJ retained high levels of Scgb1a1 protein, but the expression of Scgb1a1 progressively decreased in GFP+ cells localized more distally from the BADJ (FIG. 8F). Henceforth, this population of cells are referred to as double positive, SCGB1A1+ SPC+, cells even though they demonstrate variable expression of Scgb1a1 and are likely to undergo differentiation as they expand further away from the BADJ. These data suggest that inactivation of Abl in Scgb1a1-expressing cells greatly enhances a population of double positive, SCGB1A1+ SPC+, cells in response to injury, that these cells appear to originate from the bronchioles and/or BADJ, and then expand into the alveolar epithelium to promote regeneration.

Figure 9A:
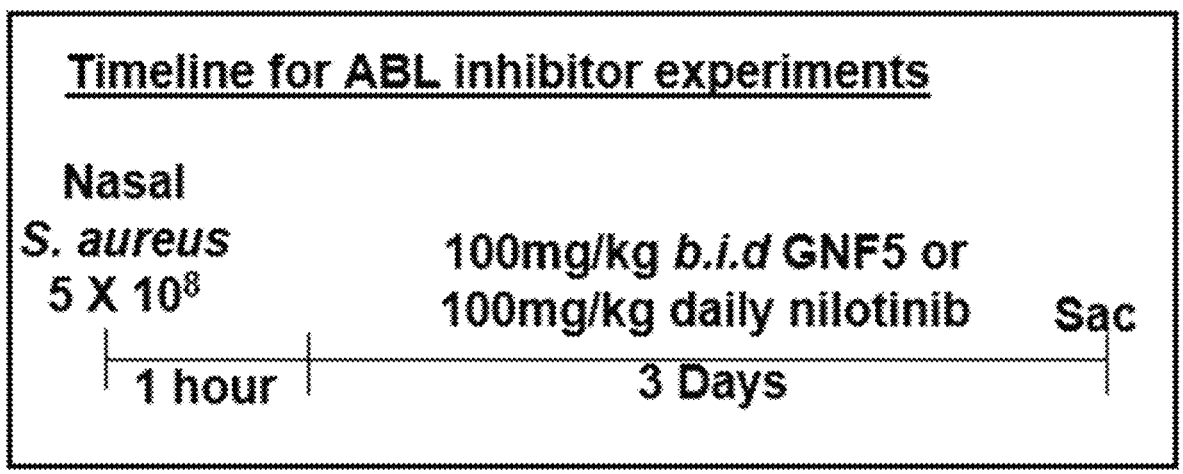
FIGS. 9A-9J show treatment with an Abl kinase inhibitor reverses lung injury following nasal insufflation of *S. aureus*.

Example 5: Pharmacological Inhibition of Abl Kinase Promotes Recovery of Mice Following Pneumonia The availability of pharmacological inhibitors of the Abl kinases prompted us to evaluate whether treatment with these compounds might be a useful therapeutic strategy following S. aureus-induced lung infection. The Abl kinase-specific allosteric inhibitor, GNF5, was used to evaluate Abl kinase inhibition as a treatment modality in bacterial pneumonia. The allosteric inhibitor, GNF5, binds specifically to the myristoyl-binding site in the kinase domain of the Abl kinases and does not inhibit other protein kinases (Zhang J. et al. (2010) Nature 463(7280):501-506). Administration of GNF5 by oral gavage twice daily results in specific inhibition of the Abl kinases without known off-target effects. Treatment was initiated one hour after nasal insufflation of S. aureus, and mice were evaluated 24 and 72 hours following injury (FIG. 9A).

Figure 9B:
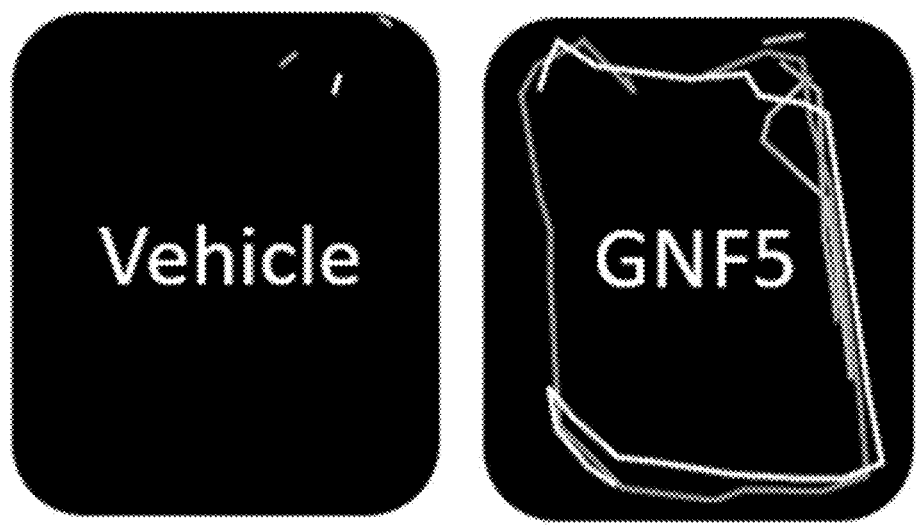
Figure 9C:
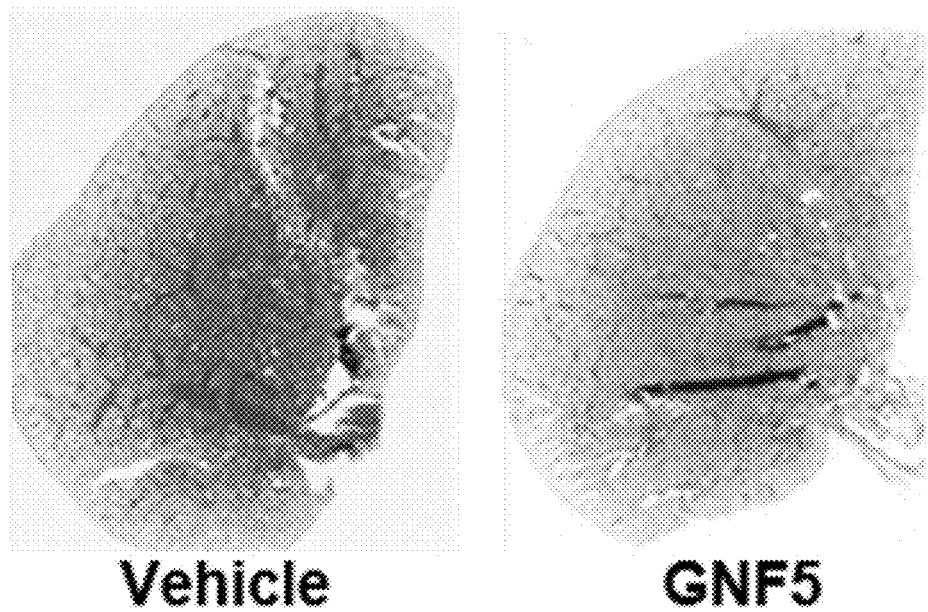
Figure 9D:
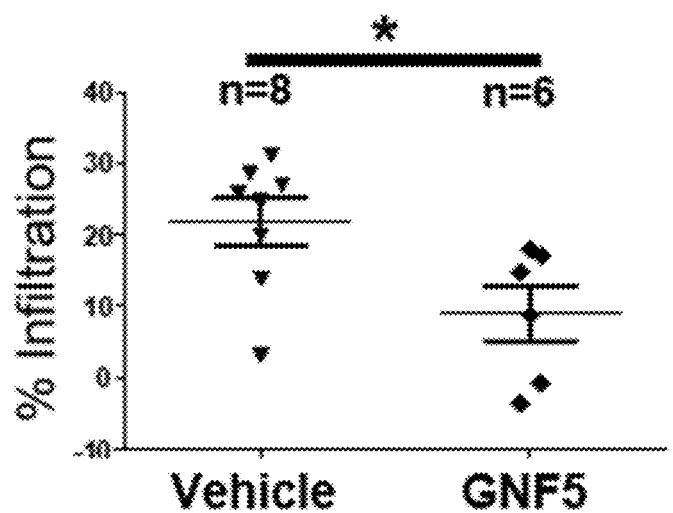

Remarkably, two doses of GNF5, one initiated 1 hour and another 16 hours after injury, were sufficient to promote recovery after 24 hours in drug-treated mice compared to vehicle control treated mice (30-second video corresponding to movement tracings in FIG. 9B). In contrast to the immobile and sickly appearance of vehicle control-treated mice, the mice treated with GNF5 were active and exhibited a healthy appearance. Analysis of lung tissue sections at 72 hours post-infection revealed a significant decrease in lung injury in the treated mice (FIG. 9C-9D).

Figure 9E:
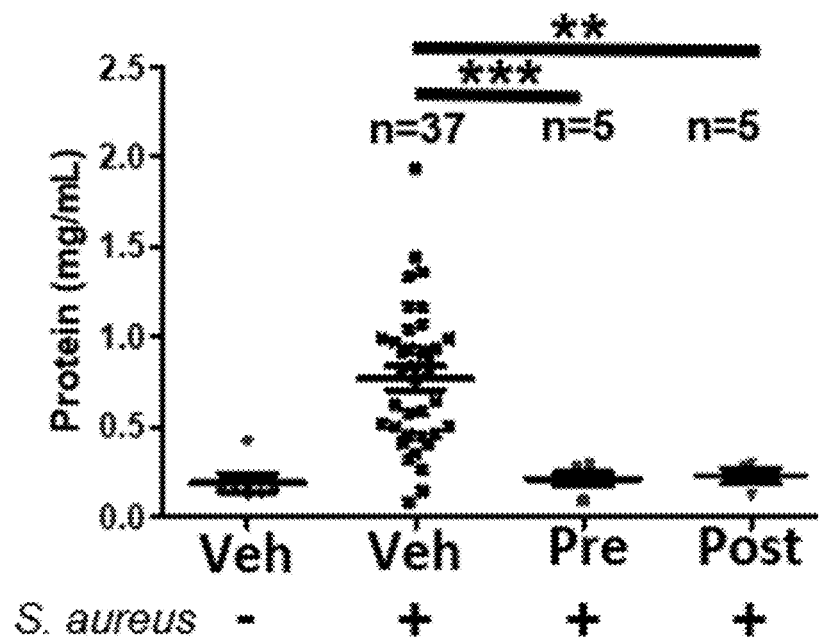
Figure 9F:
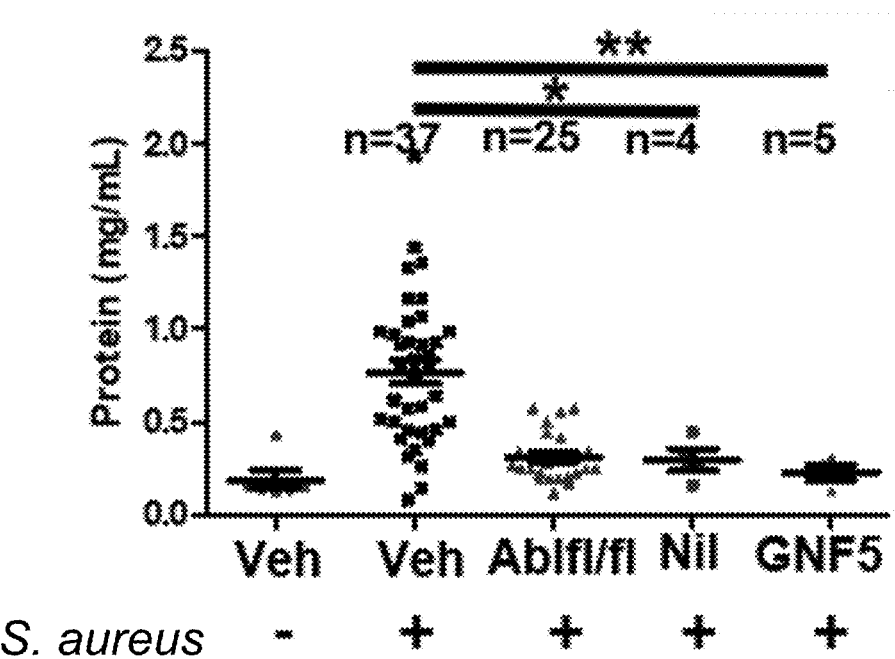

To evaluate the effect of delayed drug treatment that more closely represents the delay in treatment initiation following the onset of pneumonia symptoms in the clinical setting, treatment schedules were initiated for mice exposed to S. aureus 24 hours after injury and compared to mice treated 24 hours prior to injury. BAL samples obtained at day 3 post-infection demonstrated a significant reduction in protein concentration in both the pre-treatment group and in mice treated with GNF5 starting at 24 hours after injury (FIG. 9E). Thus, even delayed treatment confers a therapeutic effect. A significant reduction in lung injury was also observed in mice treated with the ATP-binding site Abl kinase inhibitor, nilotinib, an FDA-approved drug for treatment of chronic myelogenous leukemia driven by oncogenic BCR-ABL (FIG. 9F).

Figure 9G:
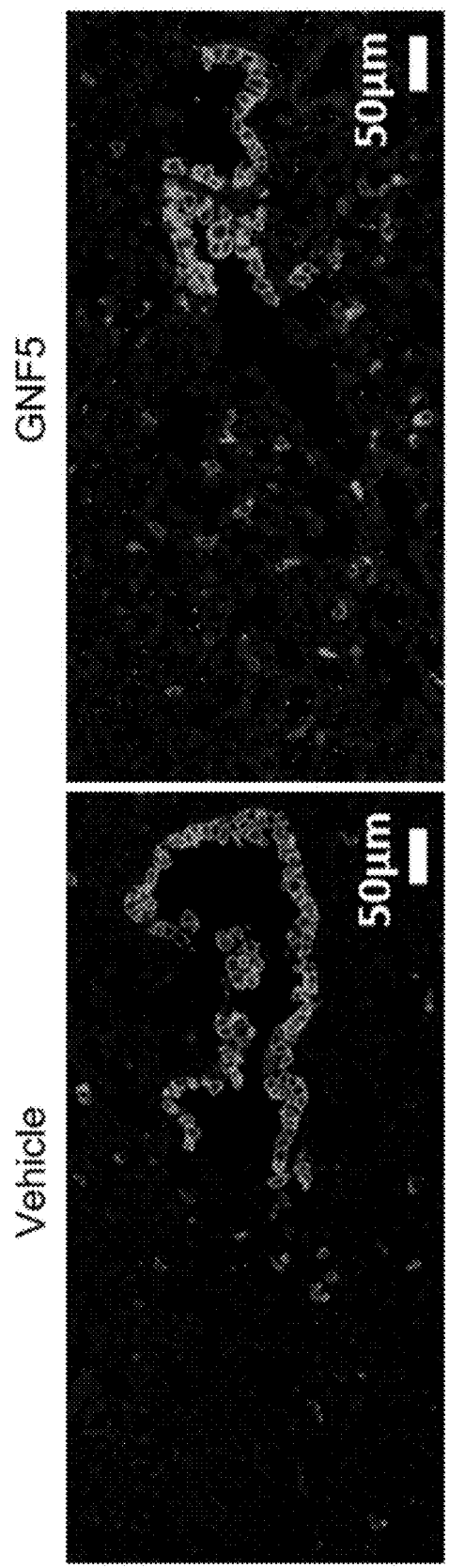
Figure 9H:
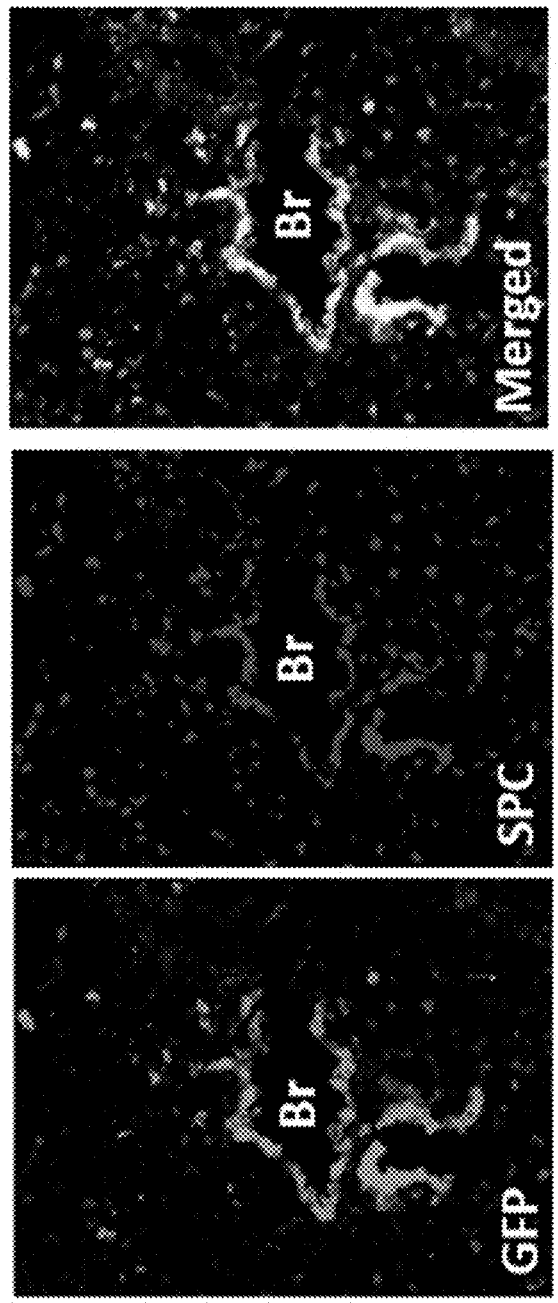
Figure 9I:
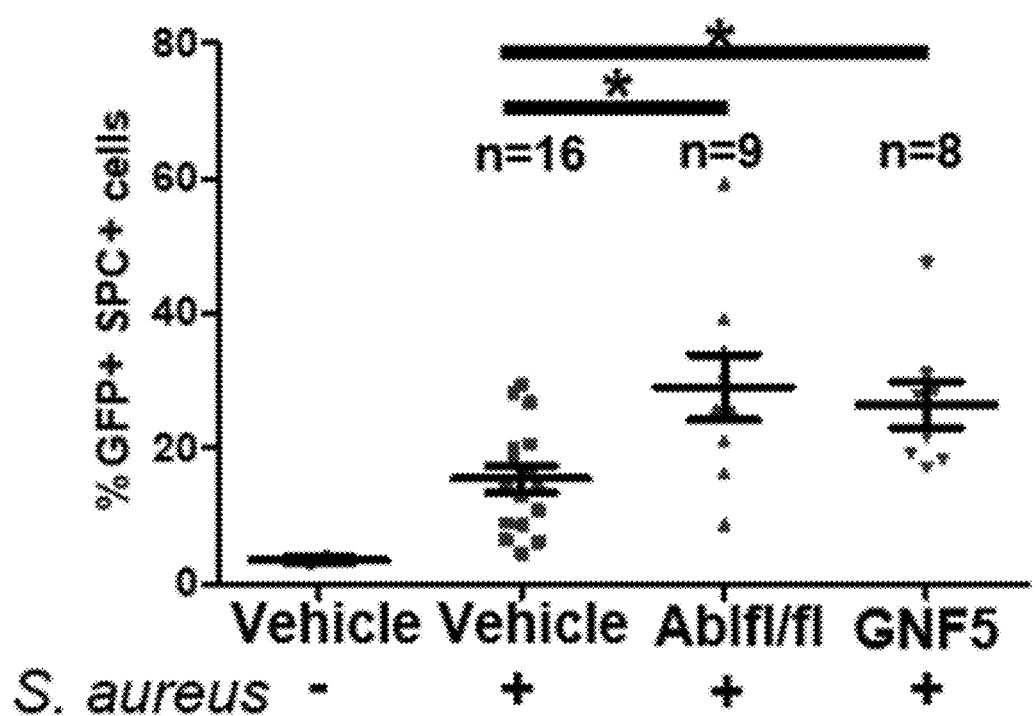
Figure 9J:
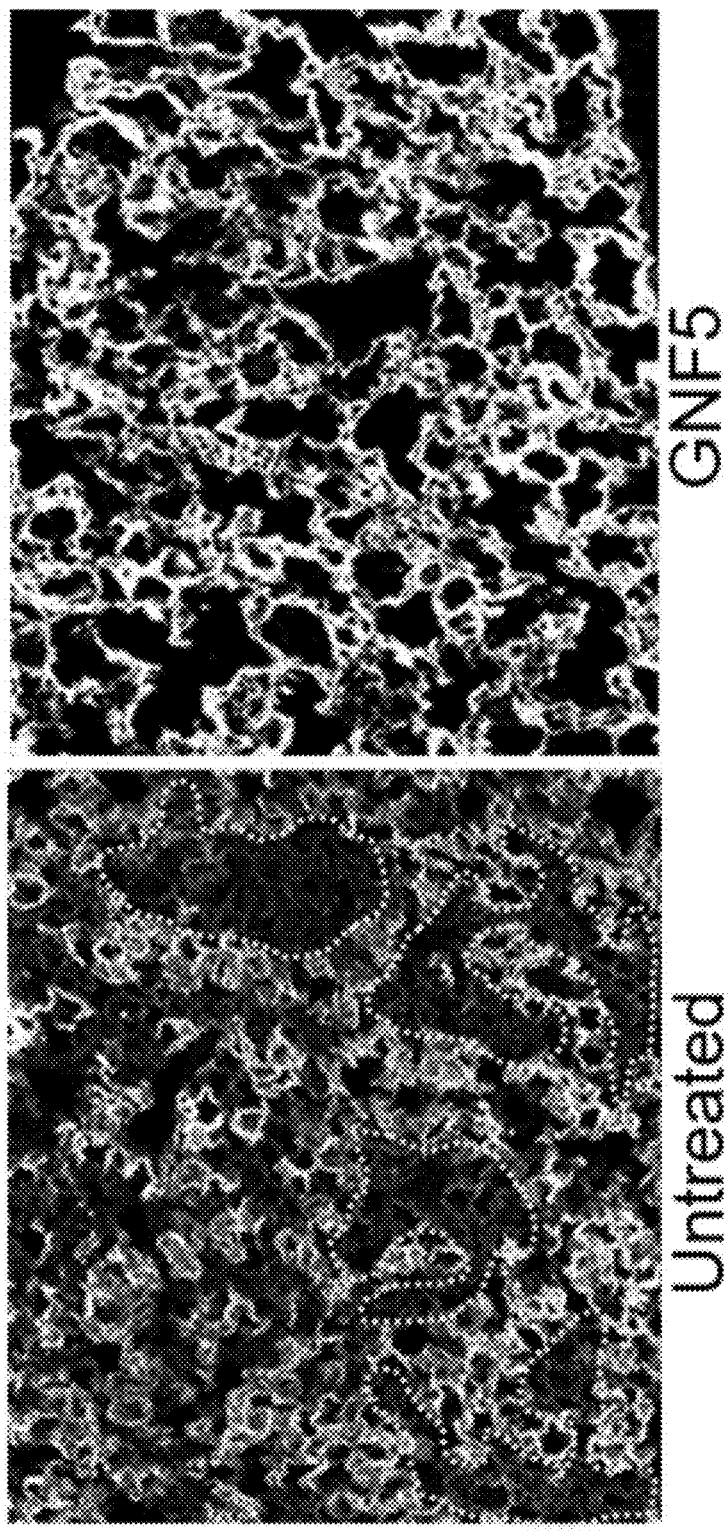

Notably, a significant increase in the proportion of GFP+ (Scgb1a1 driver) SPC+ cells in GNF5-treated mice versus vehicle-treated mice, as well as enhanced SPC expression in SCGB1A1+ cells within the bronchioles of GNF5-treated mice after injury was observed (FIG. 9G-9I). Further, the alveolar epithelium in mice treated with GNF5 recovered more rapidly by day 3 post-infection compared to control mice (FIG. 9J). These findings show that pharmacologic or genetic inactivation of Abl elicits an expansion of double-positive GFP+ (Scgb1a1 driver) SPC+ cells that promote rapid regeneration of the alveolar epithelium following injury.

Example 6: Genetic Deletion of Abl1 Promotes Expansion of SCGB1A1+ and SOX2+ Airway Cells that Co-Express SPC Following Pathogen-Induced Injury To characterize the specific cell types responsible for the marked expansion of SCGB1A1+ SPC+ cells into the damaged alveolar epithelium in Abl1-deficient mice, employed three different mouse models were used: (1) CC10 (Scgb1a1)-CreERT; Rosa26-fGFP, (2) SPC (Sftpc)-CreERT2; Rosa26-tdTomato, and (3) SOX2-eGFP mice. Prior studies identified a small pool (<1 cell per BADJ) of SCGB1A+ SPC+ putative "bronchioalveolar stem cells" (BASC) within the BADJ as a potential cell type of origin for Type II AECs (Kim C F, et al. (2005) Cell 121(6):823-835). Consistent with previous reports, it was found that after pathogen-induced injury, wild type mice displayed an increase in the number of SPC+ cells that were also GFP+ around the BADJ (FIG. 8A). However, the number of GFP+ SPC+ cells markedly increased from <5% up to ~50% in the Abl1$^{fl/fl}$ mice after pathogen exposure (FIG. 8E). The profound increase in the SCGB1A1+ SPC+ cell population in Abl1 knockout mice is unlikely to derive from the limited pool of resident double-positive SCGB1A1+ SPC+ cells within the BADJ alone.

Figure 10A:
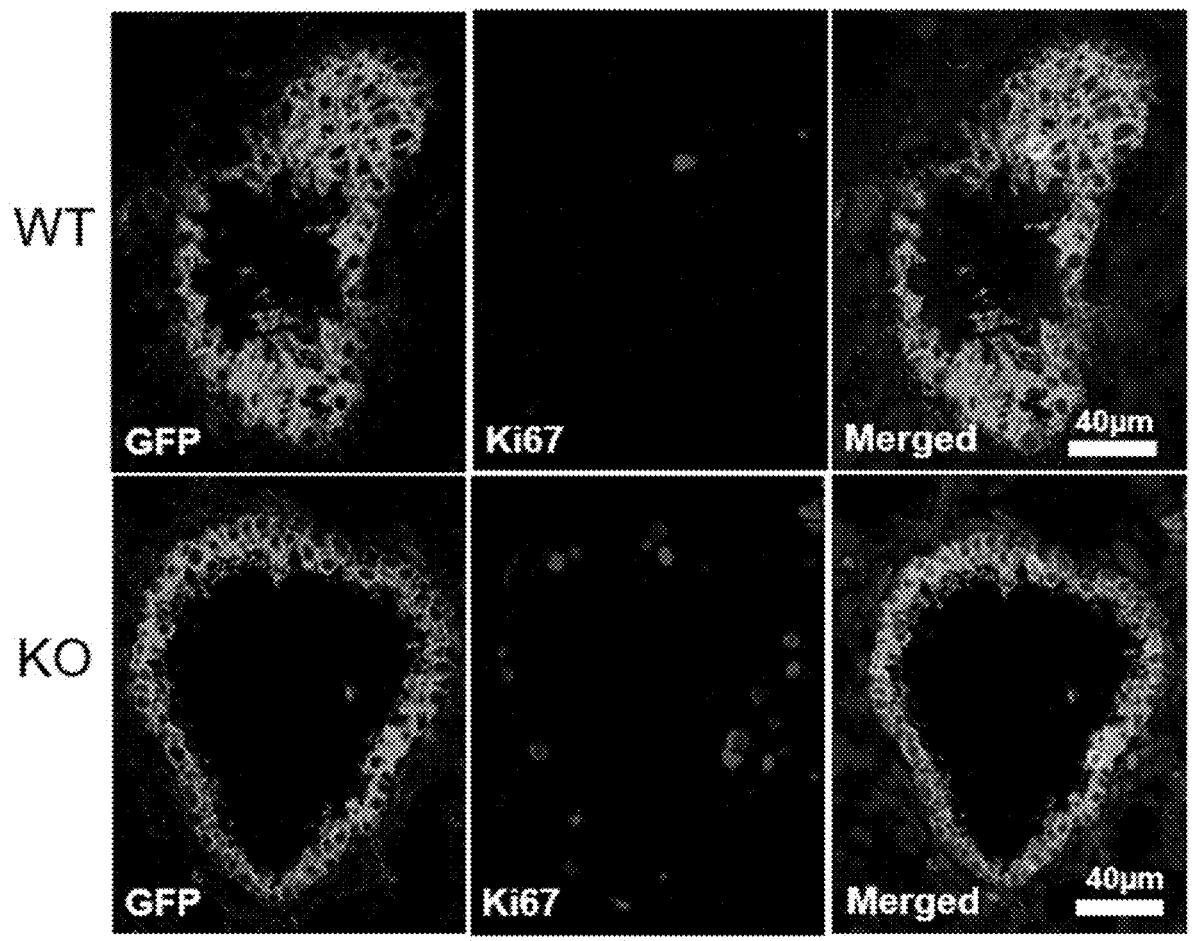
FIGS. 10A-10G show genetic inactivation of Abl1 promotes proliferation and differentiation of Scgb1a1+ cells following injury.
Figure 10B:
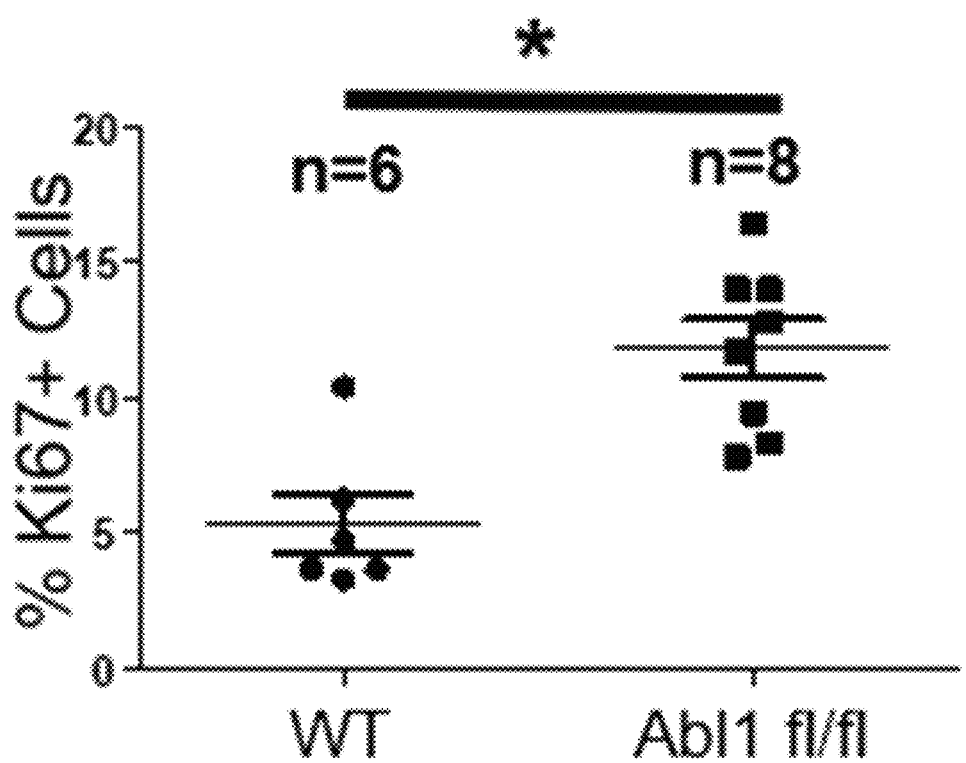

To examine whether Abl1 inactivation in SCGB1A1+ cells affected their proliferation, immunofluorescence staining for the Ki67 proliferation marker was performed. A significant increase in proliferating SCGB1A1+ cells was observed in bronchioles of Abl1$^{fl/fl}$ mice compared to wild-type mice, with maximal increase occurring at 4 hours after injury (FIG. 10A-10B).

Figure 10C:
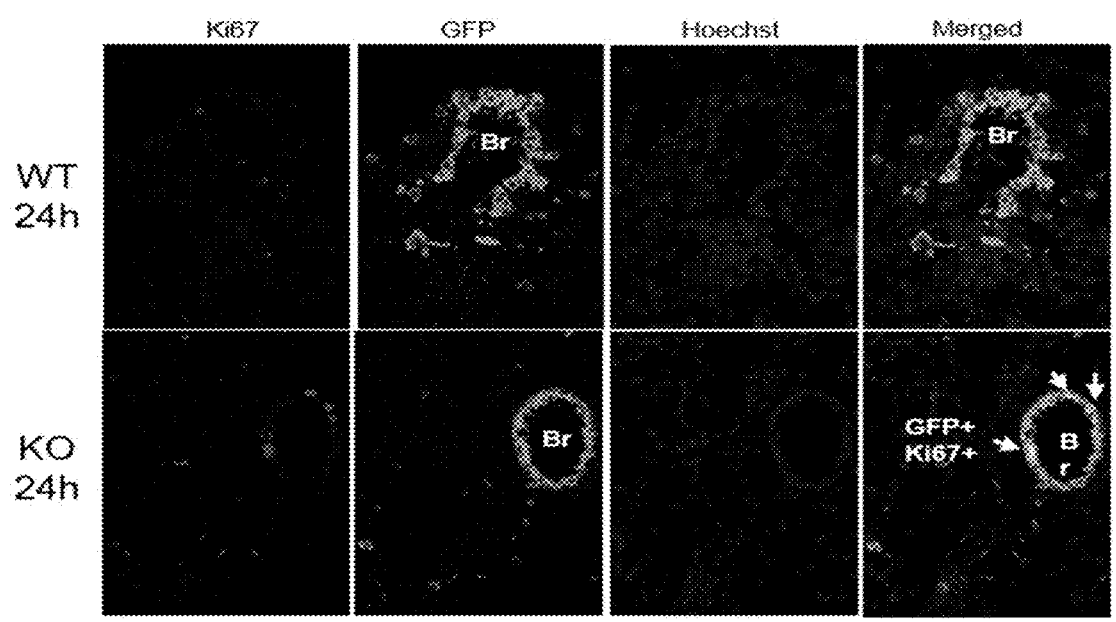
Figure 10D:
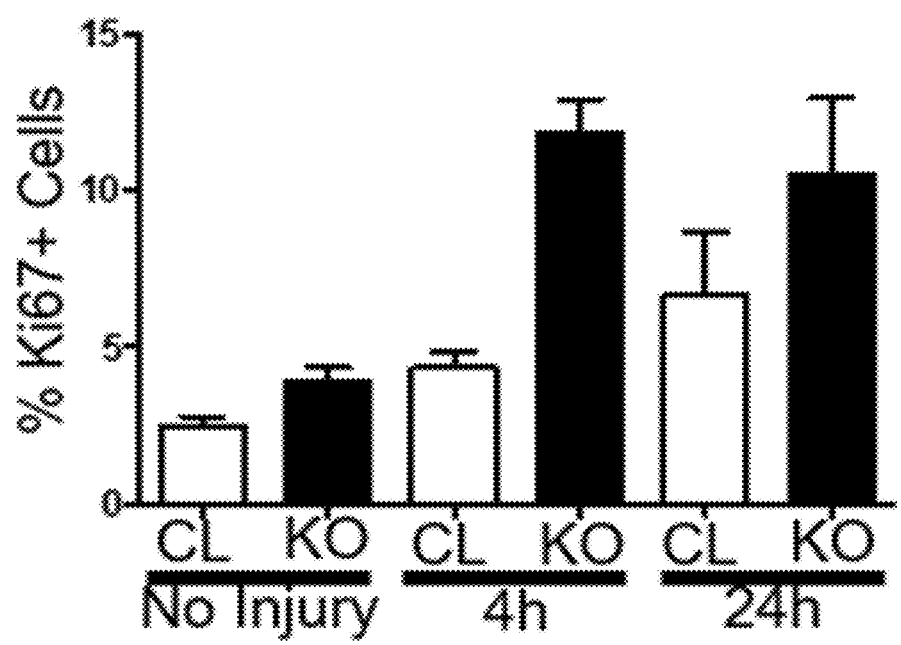

These findings demonstrate that inactivation of Abl1 in SCGB1A1+ cells, elicits an early wave of cell proliferation (~4 h) following pathogen exposure that is not detected in wild type controls, which show increased proliferation at 24 h post-injury compared to uninjured mice (FIG. 10C-10D).

Figure 10E:
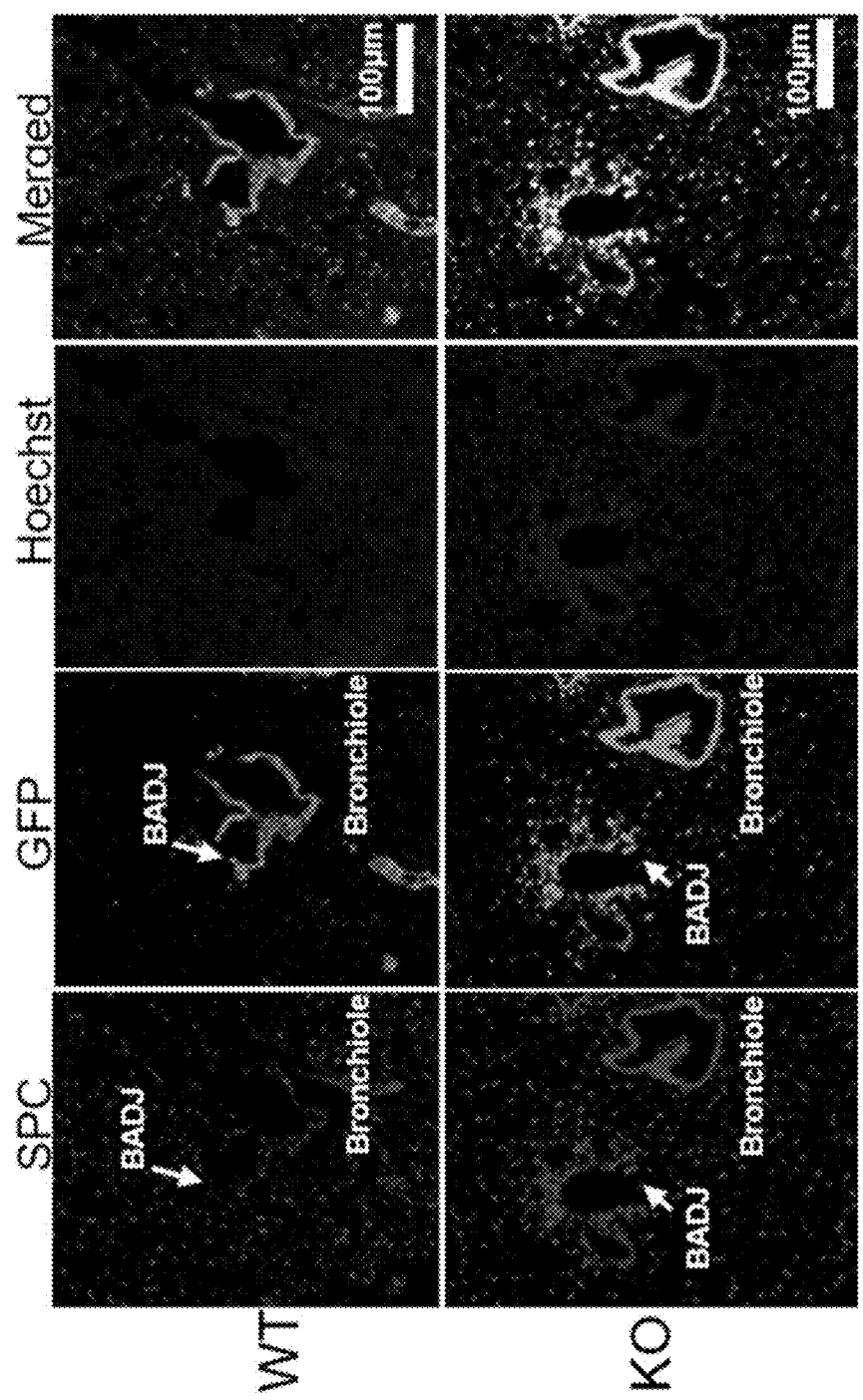
Figure 10F:
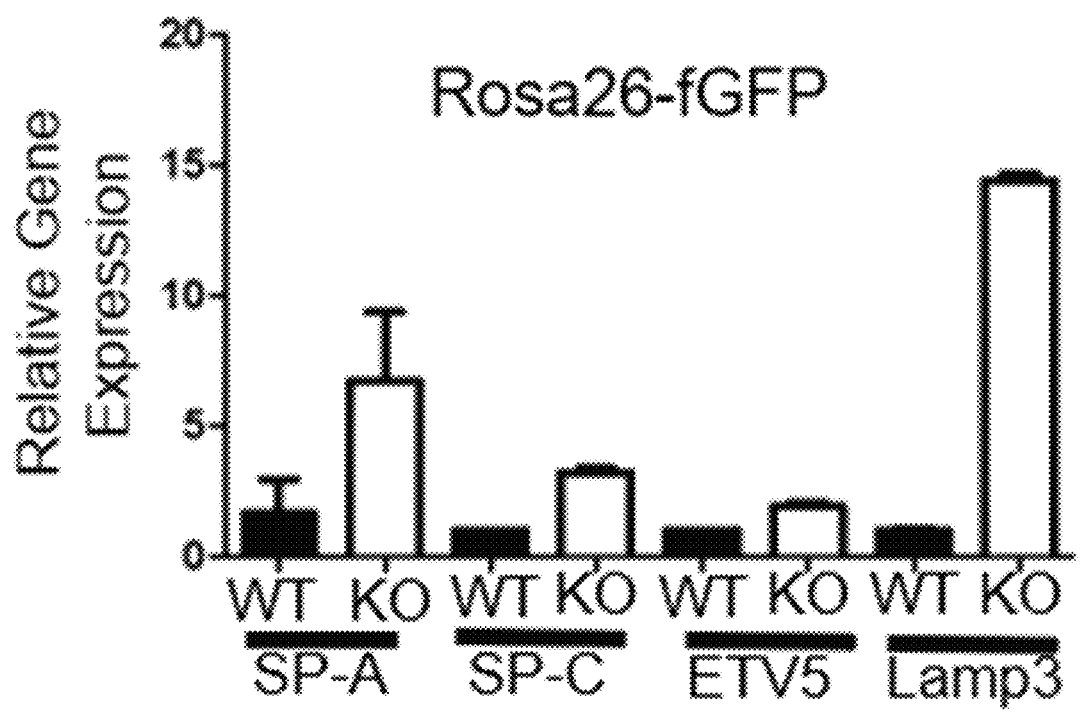
Figure 10G:
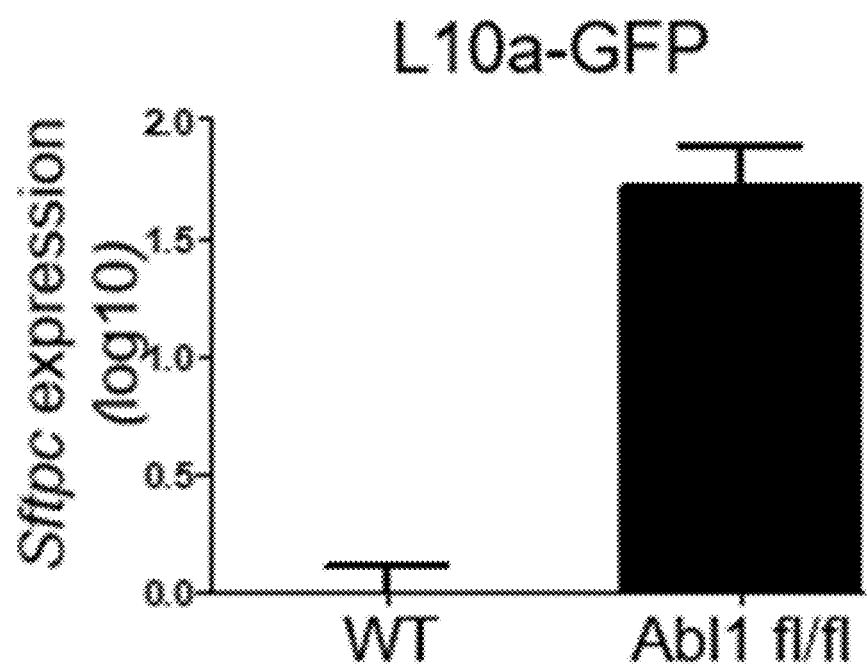

Next, whether inactivation of Abl1 in SCGB1A1+ cells affected their differentiation was evaluated. Co-staining for GFP and SPC followed by immunofluorescence microscopy revealed a significant increase in expression of SPC within the bronchiolar secretory cell population of Abl1 knockout compared to wild-type control mice by day 3 following injury (FIG. 10E). In the absence of injury, SPC expression is specific to Type II AECs and is not detected in the bronchiolar epithelium. To determine whether Abl1 inactivation elicited an increase in the expression of other Type II AEC markers, fluorescence activated cell-sorting (FACS) of GFP+ cells from lungs of CC10 (Scgb1a1)-CreERT; Rosa26-fGFP; Abl1$^{wt}$ and Abl1$^{fl/fl}$ mice was performed. RT-qPCR analysis of lysates from the isolated GFP+ cells revealed upregulation (>10 fold) of four of the most highly expressed genes in Type II alveolar cells (Sftpa, Sftpc, Lamp3, and ETV5) in Abl1 knockout compared to wild-type mice (FIG. 10F). To obtain a functional readout of altered gene transcription induced by Abl1 inactivation, we employed the translating ribosome affinity purification (TRAP) technique (Heiman M, et al. (2014) Nature protocols 9(6): 1282-1291) using lungs from CC10 (Scgb1a1)-CreERT; L10a-eGFP; Abl1$^{fl/fl}$ and corresponding wild-type, control mice. RT-qPCR showed an increase in actively translated Sftpc mRNA that was pulled down from GFP-labeled ribosomes in Abl1 knockout compared to wild-type mice (FIG. 10G). These data show that Abl1 inactivation in a large population of SCGB1A+ cells within the bronchioles elicits an early wave of enhanced proliferation at 4 hours after alveolar epithelial damage, followed by a wave of differentiation 24-72 hours after injury.

Figure 11A:
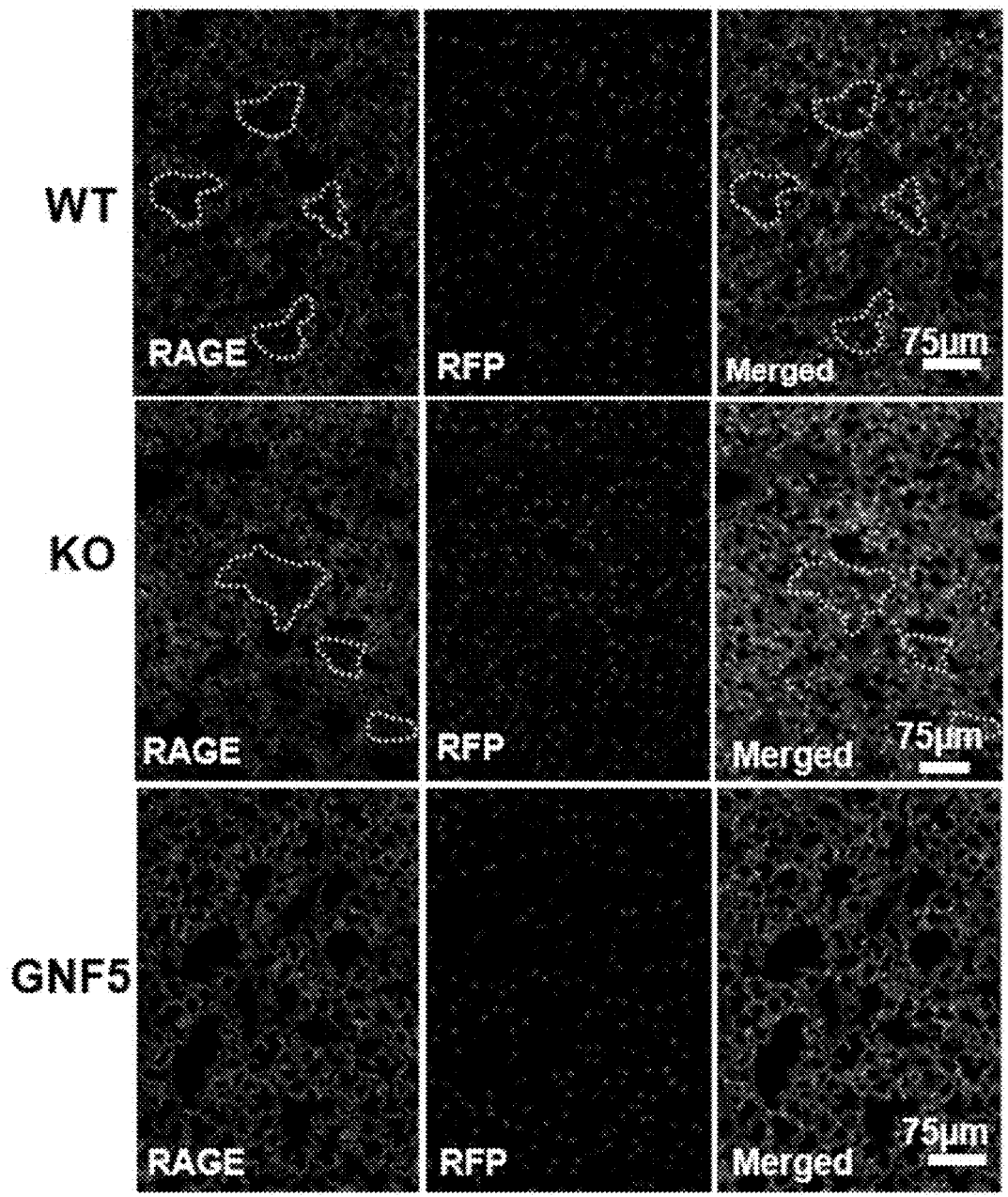
FIGS. 11A-11C show pharmacological (global) inhibition of Abl kinases but not conditional loss of Abl1 in SPC+ cells leads to increased regeneration of Type I alveolar epithelial cells after injury.
Figure 11B:
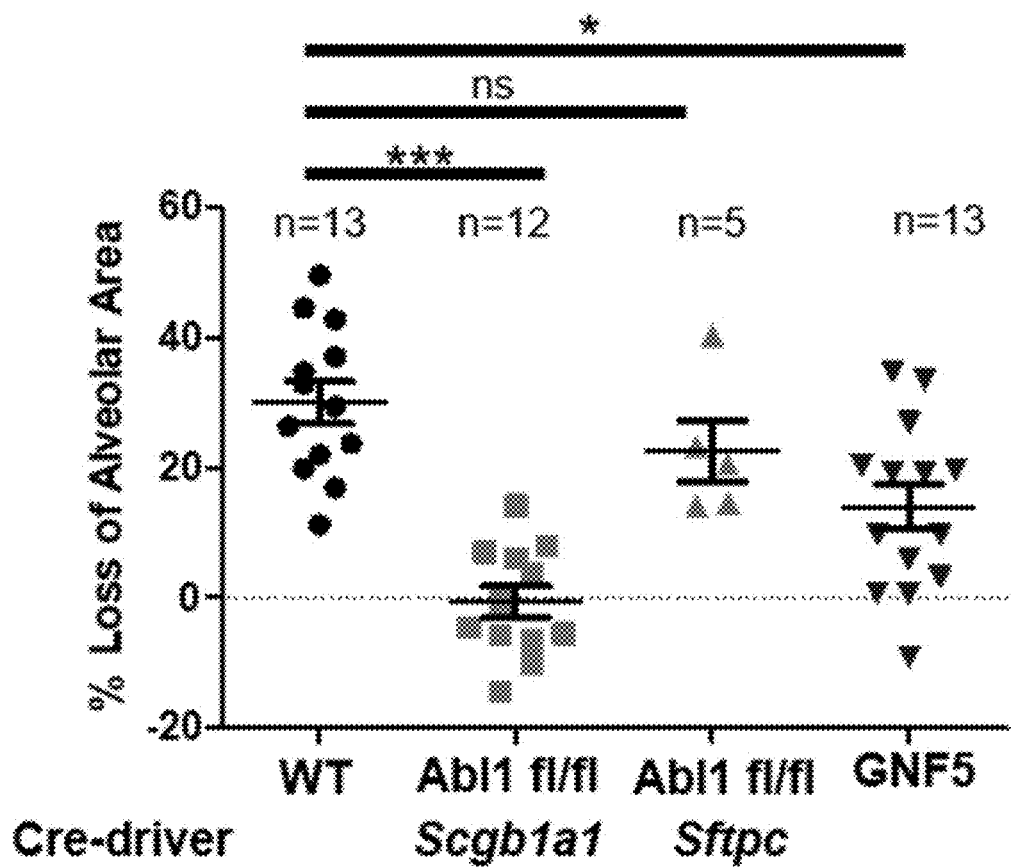
Figure 11C:
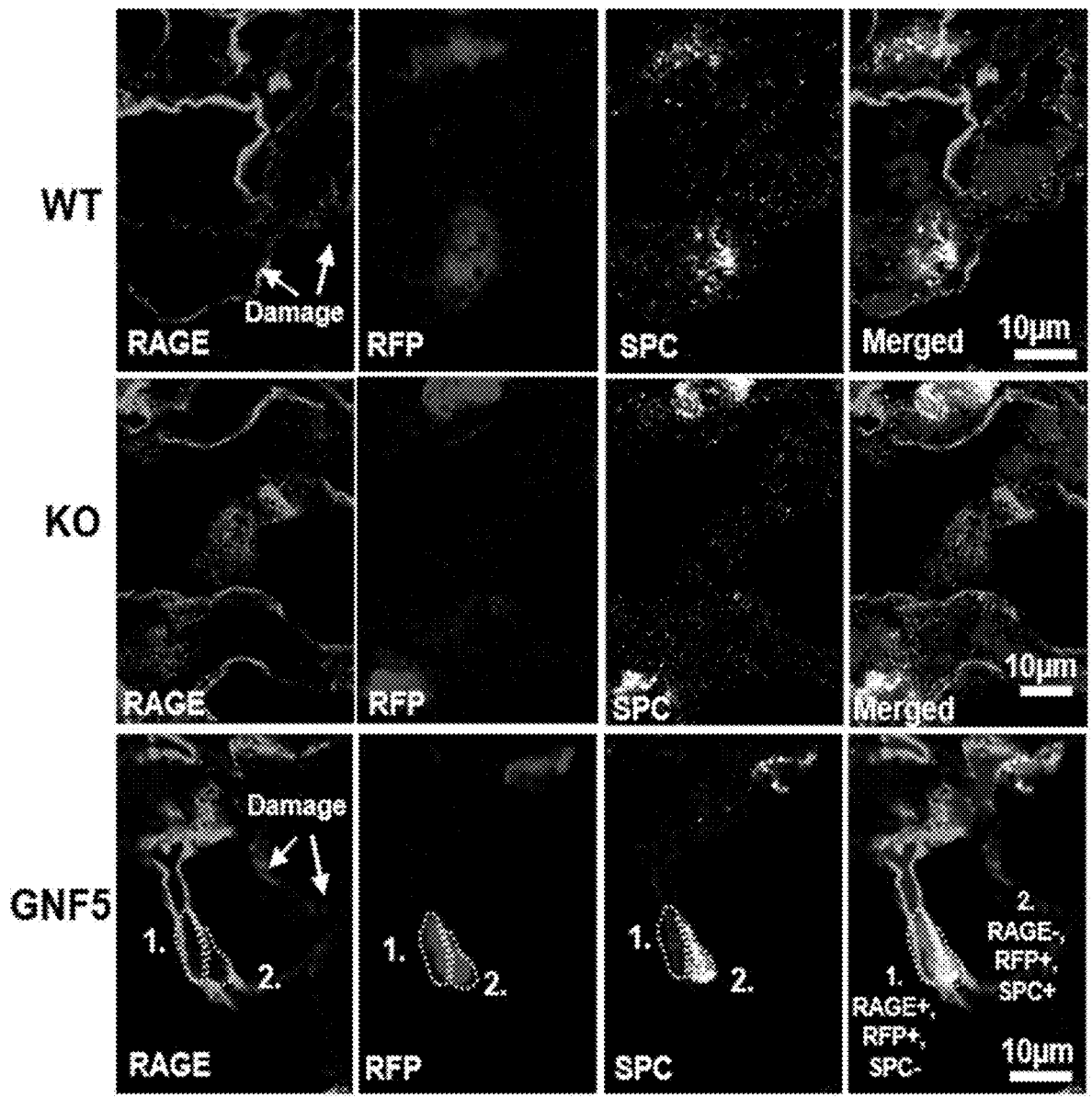

To determine whether Abl kinase inhibition specifically in Type II alveolar epithelial cells (AEC) contributes to the observed regenerative phenotype in mice after injury, SPC (Sftpc)-CreERT2; Rosa26-tdTomato mice that were Abl1$^{wt}$ or Abl1$^{fl/fl}$ were used. After exposure to *S. aureus*, damage to the lung alveolar epithelium was detected in untreated SPC (Sftpc)-CreERT2; Rosa26-tdTomato; Abl1$^{wt}$ and Abl1$^{fl/fl}$ mice compared to SPC (Sftpc)-CreERT2; Rosa26-tdTomato mice treated with the Abl kinase inhibitor, GNF5 (FIG. 11A-11B). Notably, tdTomato+, RAGE+ (Type I) cells derived from tdTomato+, SPC+, RAGE-(Type II) cells were detected at sites of damage only in mice treated with GNF5 three days after injury (FIG. 11C). While it has been well-established that Type II AECs contribute to Type I AECs regeneration after injury, these findings are consistent with published data that, in wild-type mice, Type I AECs lineage-derived from Type II AECs are only observed 5-7 days after injury. This data suggests that knockout of Abl1 in Type II AECs (SPC-CreERT2 model) alone is unlikely to contribute to the accelerated regeneration of Type I AECs observed 72 hours after knockout of Abl1 in Scgb1a1+ cells (CC10-CreERT model).

Figure 12A:
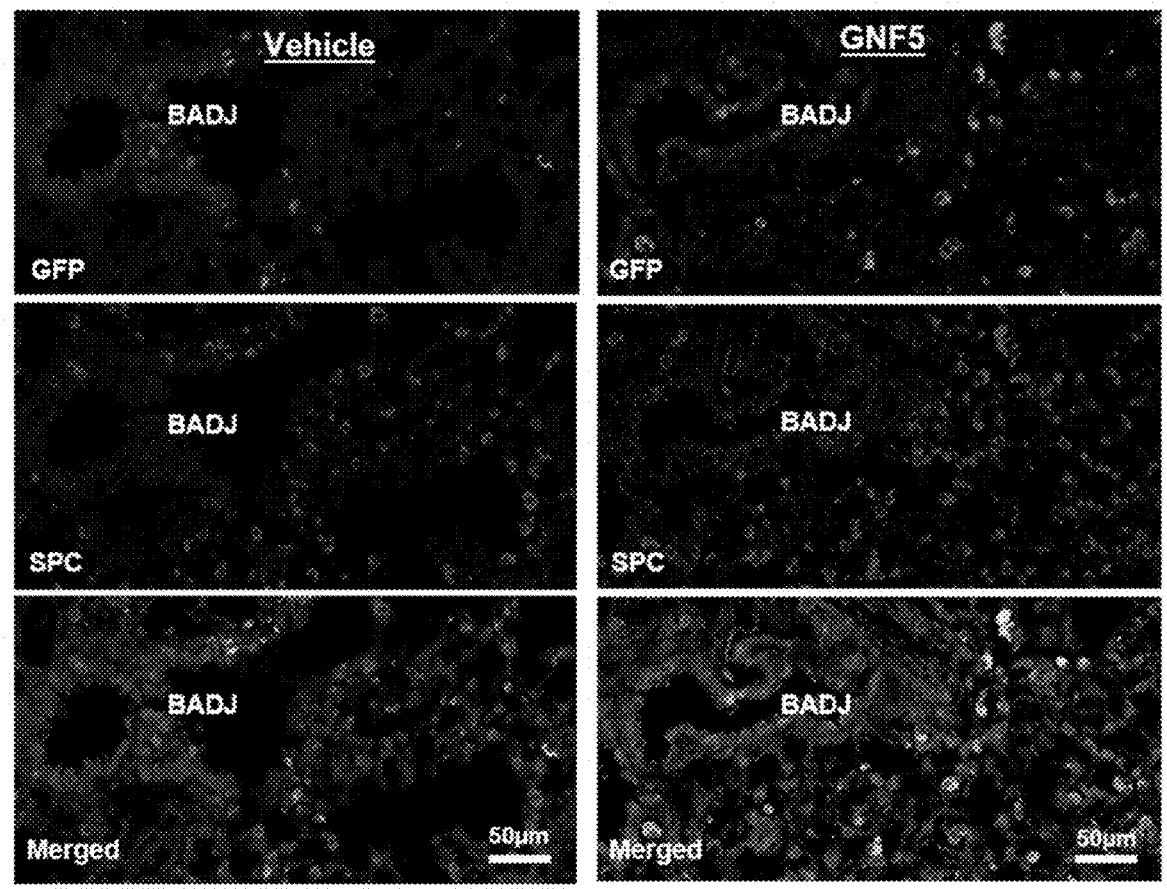
FIGS. 12A-12B show inhibition of Abl1 promotes expansion of SOX2+ SPC+ cell population in mouse lungs following injury.
Figure 12B:
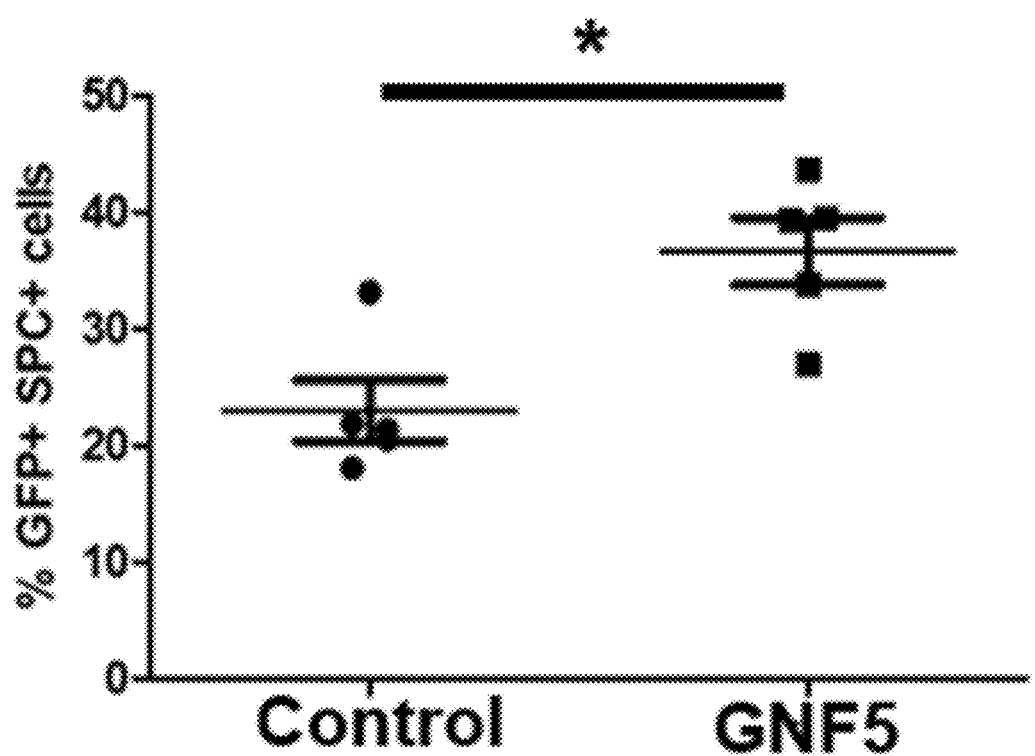

To further ascertain whether the expansion of SCGB1A+ SPC+ cells arises from the bronchioles and BADJ versus the small fraction (~10%) of SCGB1A1+ Type II AECs, a SOX2$^{eGFP}$ knockin/knockout mouse model was used. Within the lung, SOX2 is expressed specifically in airway cells but not in alveolar cell. SOX2$^{eGFP}$ mice were pre-treated with vehicle or the Abl kinase inhibitor, GNF5 (100 mg/kg, b.i.d. via oral gavage), 24 hours prior to nasal insufflation of *S. aureus*. Three days after injury, lungs were harvested, paraffin-embedded, sectioned, and stained with antibodies to GFP and SPC. Experiments performed in heterozygous mice in which the open reading frame of SOX2 is replaced by eGFP allow for identification of cells actively expressing SOX2, and not just lineage-derived cells from the airway cell population. A dramatic increase in the proportion of SOX2+ SPC+ cells expanding from the bronchioles into the lung parenchyma in mice treated with the Abl kinase allosteric inhibitor, GNF5, compared to vehicle control treated mice was observed (FIG. 12A-12B). Thus, Abl kinase inhibition promotes expansion of airway cells that co-expresses SPC following injury.

Taken together, data from these three different mouse models suggest that inactivation of Abl kinases specifically in SCGB1A1+ and SOX2+ airway epithelial cells, but not Type II AECs, leads to expansion of double positive SCGB1A1+ SPC+ or SOX2+ SPC+ cell populations that precede regeneration of the damaged alveolar epithelium following injury.

Figure 13A:
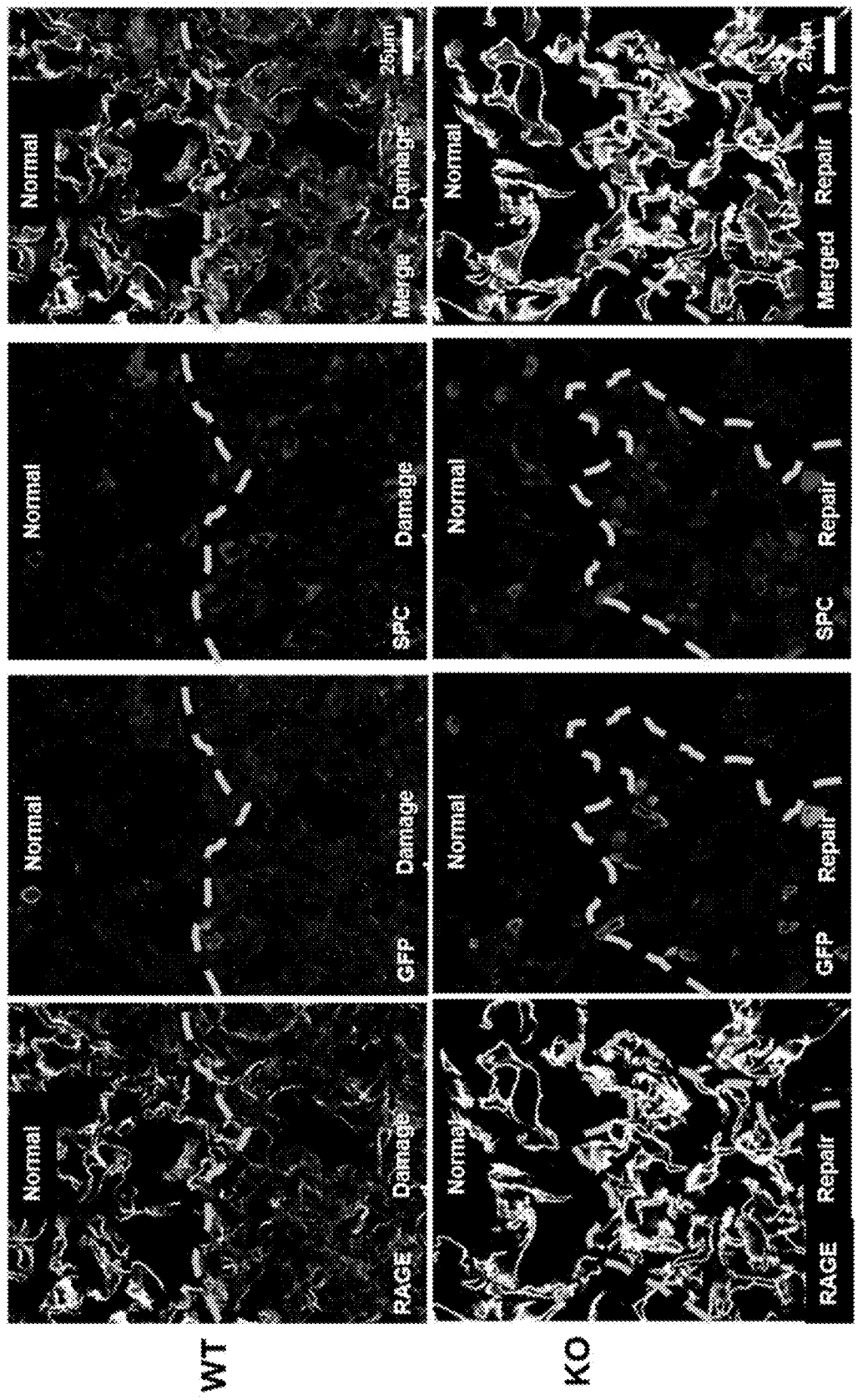
FIGS. 13A-13E show Scgb1a1+ SPC+ cells expand to sites of injury and promote regeneration.

Example 7: Mobilization of SCGB1A1+ SPC+ Cells to Sites of Injury Promotes Alveolar Regeneration To track the mobilization of the double-positive SCGB1A1+ SPC+ cell population during regeneration of the alveolar epithelium, immunofluorescence staining for GFP (Scgb1a1 driver), SPC (Type II AEC marker), and RAGE (Type I AEC marker) proteins were performed in wild-type and Abl knockout mice at various times after exposure to *S. aureus*. In wild-type mice, we found an increase in the number of SPC+ but GFP-negative Type II AECs cells at sites of injury in the alveolar epithelium at Day 3 post-infection (FIG. 13A, top panels). By contrast, Abl1 knockout in CC10 (Scgb1a1)-CreERT; Rosa26-fGFP: Abl1$^{fl/fl}$ mice exposed to *S. aureus* displayed increased numbers of GFP+ (Scgb1a1 driver) SPC+ cells at sites of alveolar repair following damage (FIG. 13A, bottom panels).

Figure 13B:
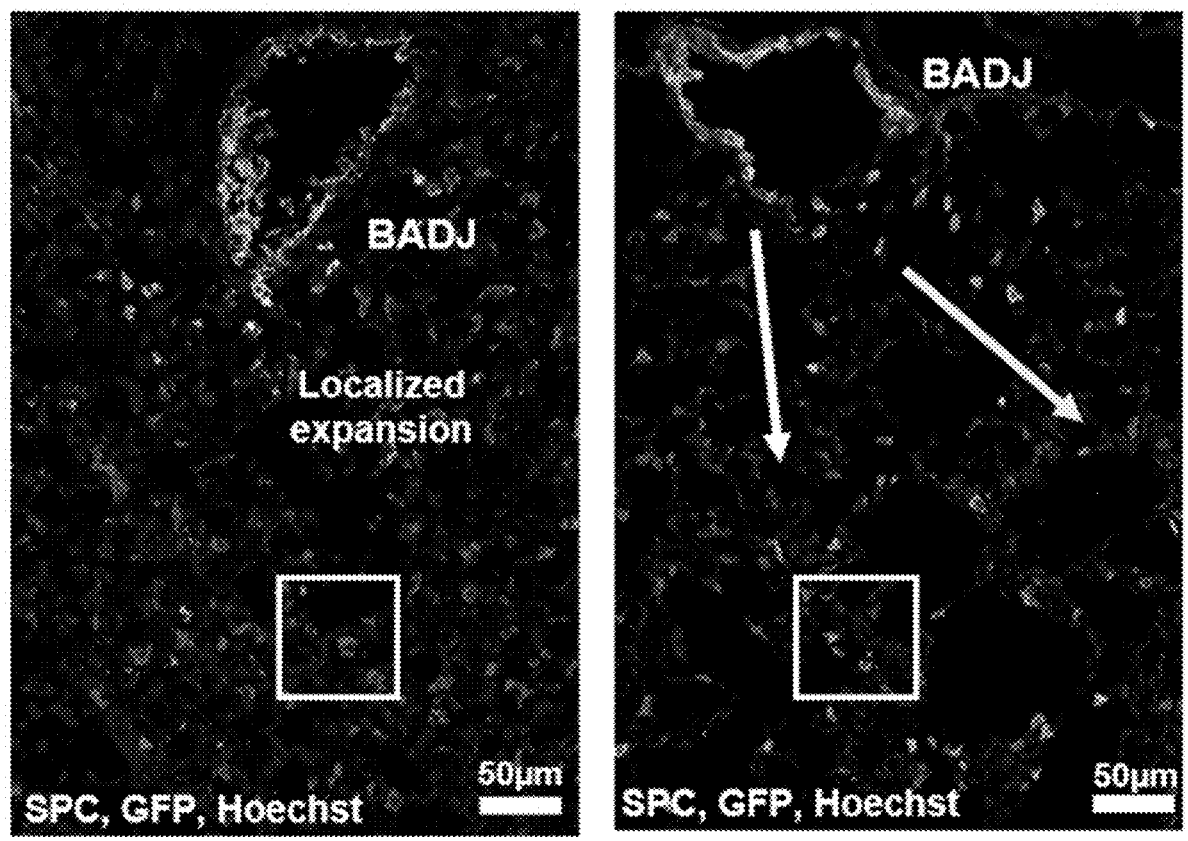
Figure 13C:
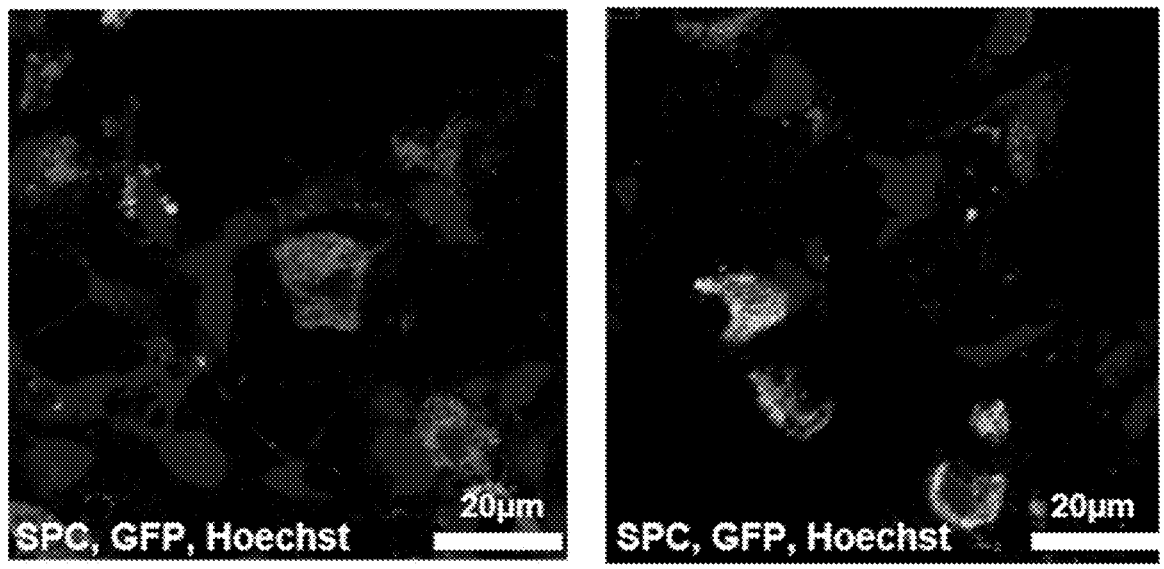

The architecture of the damaged alveolar epithelium was largely restored (as evaluated by immunostaining for RAGE) in the Abl1 knockout mice by day 3 post-infection with areas of hyper-cellularity and decreased alveolar volume, suggestive of damaged epithelium undergoing repair. In Abl1 knockout mice, GFP+ (Scgb1a1 driver) SPC+ cells expand from the bronchioles and/or BADJ to sites of damage, which precedes enhanced alveolar epithelial cell regeneration, and these phenotypes are not observed in wild-type mice (FIG. 13B-13C).

Figure 13D:
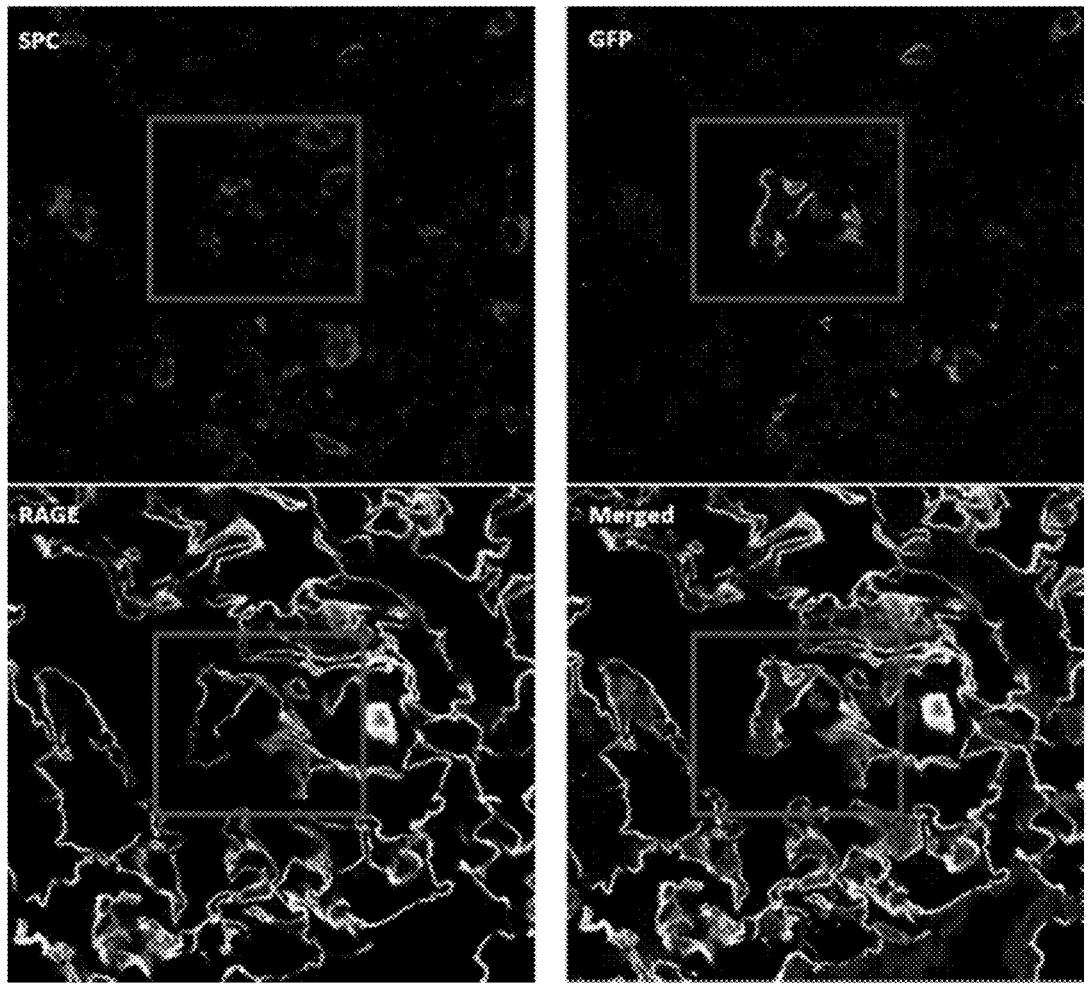
Figure 13E:
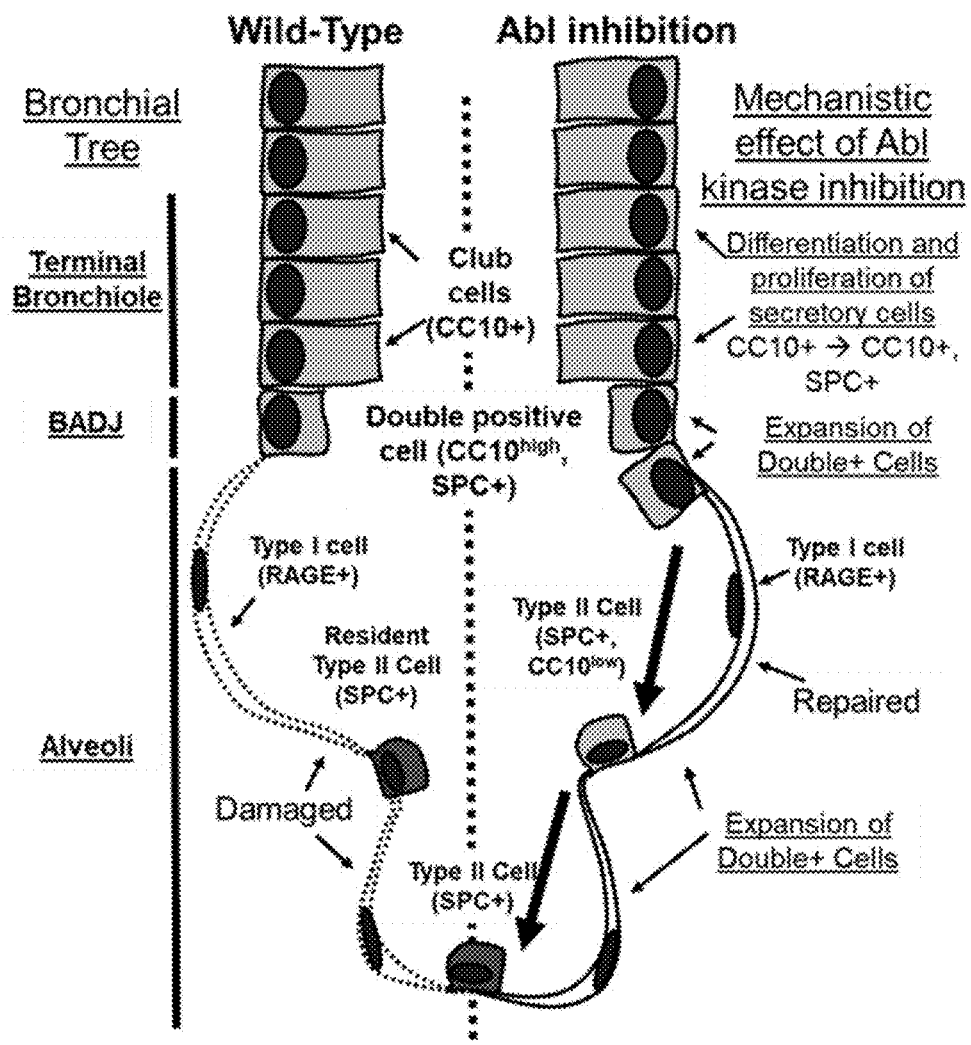

To evaluate whether SCGB1A1+ SPC+ cells promote alveolar epithelium regeneration directly by differentiating into Type I AECs, mouse lung sections were stained at various times following injury to detect the presence of triple positive GFP+ (Scgb1a1 driver), RAGE+, SPC+ versus GFP+, RAGE+ but SPC− cells at sites of injury. CC10 (Scgb1a1)-CreERT2; ROSA26-fGFP mice treated with tamoxifen two weeks prior to inducing lung injury were evaluated 30 days after injury for GFP+ populations in the lung. Small clusters of triple positive cells as well as GFP+ (Scgb1a1 driver) RAGE+ cells were detected in lung sections of both wild-type and Abl1 knockout mice 30 days following injury but not at earlier time points (FIG. 13D). Because Abl1 knockout mice exhibited accelerated recovery from infection 24 to 72 hours after injury, it is unlikely that differentiation of GFP+(Scgb1a1 driver) SPC+ cells into GFP+ RAGE+ cells at day 30 post-injury significantly contributed to the observed early alveolar regeneration phenotypes. It is more likely that double-positive SCGB1A1+ SPC+ cells mobilize to sites of injury and promote local Type II AECs to regenerate Type I AECs leading to repair of the damaged lung epithelium (FIG. 13E).

Consistent with this possibility is the observation that SPC (Sftpc)-CreERT2; Rosa26-tdTomato mice treated with the Abl kinase allosteric inhibitor, GNF5, displayed an increase in the proportion of tdTomato+(Sftpc driver) RAGE+ Type I AECs compared to untreated wild-type and Abl1 knockout mice in SPC+ Type II AECs (FIB. 11A-11C).

Figure 14A:
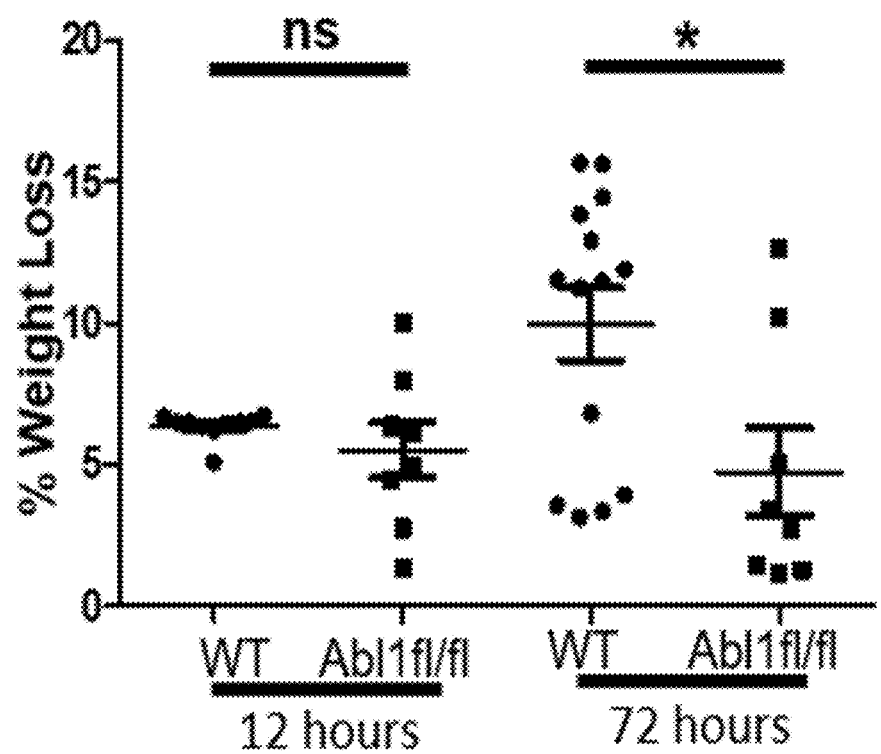
FIGS. 14A-14C show conditional knockout of Abl1 in CC10 (Scgb1a1)-CreERT; Rosa26-fGFP mice cells leads to expansion of double positive GFP+ SPC+ cells following exposure to *S. pneumoniae*.
Figure 14B:
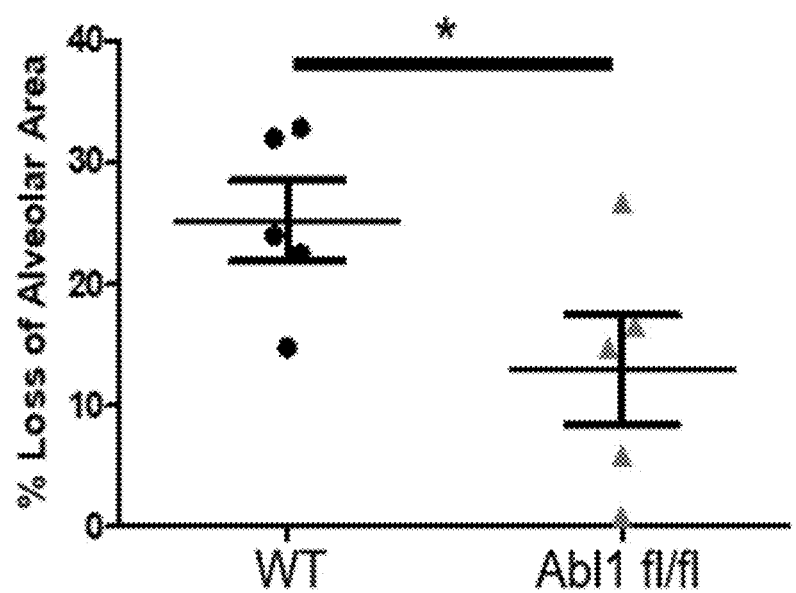
Figure 14C:
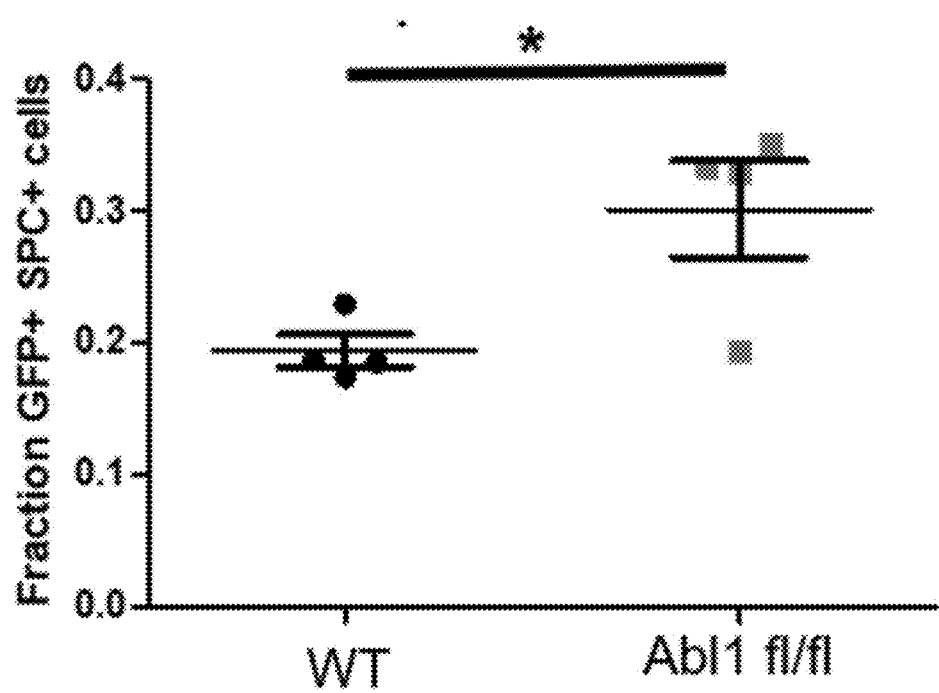

Example 8: Loss of Abl1 in SCGB1A1+ Lung Epithelial Cells Promotes Recovery in Mice Following *S. pneumoniae* Induced Injury To assess whether conditional knockout of Abl1 promoted lung epithelial regeneration in mice following exposure to other pathogens, *Streptococcus pneumonia* was used. Recovery in wild type and Abl1 knockout mice following nasal insufflation of *S. pneumoniae*, a more virulent bacterial strain than the strain of *S. aureus* used, was evaluated. CC10 (Scgb1a1)-CreERT2; Rosa26-fGFP mice were treated with tamoxifen two weeks prior to inducing lung injury. Mice were inoculated with $6\times10^5$ CFU *Streptococcus pneumoniae* and evaluated at multiple time points after injury. While both wild-type and Abl1 conditional knockout mice (Scgb1a1 driver) lost the same amount of body weight within 12 hours after injury, the Abl1 knockout mice recovered body weight more quickly compared to wild-type, control mice (FIG. 14A). Consistent with these findings, decreased damage to the lung parenchyma was observed, as measured by an increase in average alveolar area/volume, in Abl1 knockout compared to wild-type mice (FIG. 14B). A significant increase in the proportion of GFP+ (Scgb1a1 driver) SPC+ cells in Abl1 knockout versus wild-type mice was also observed. Interestingly, in the *S. pneumoniae* injury model, a dramatic expansion of the double positive cells as early as 6 hours after injury was found (FIG. 14C). Thus, data from both *S. aureus*- and *S. pneumoniae*-induced injury models demonstrate that conditional knockout of Abl (Scgb1a1 driver) leads to expansion of a subpopulation of SCGB1A1+ SPC+ cells, promotes lung regeneration, and accelerates mouse recovery after injury.

Example 9: Abl Kinase Inhibition in a Mouse Model of H1N1 Influenza Injury

Figure 15A:
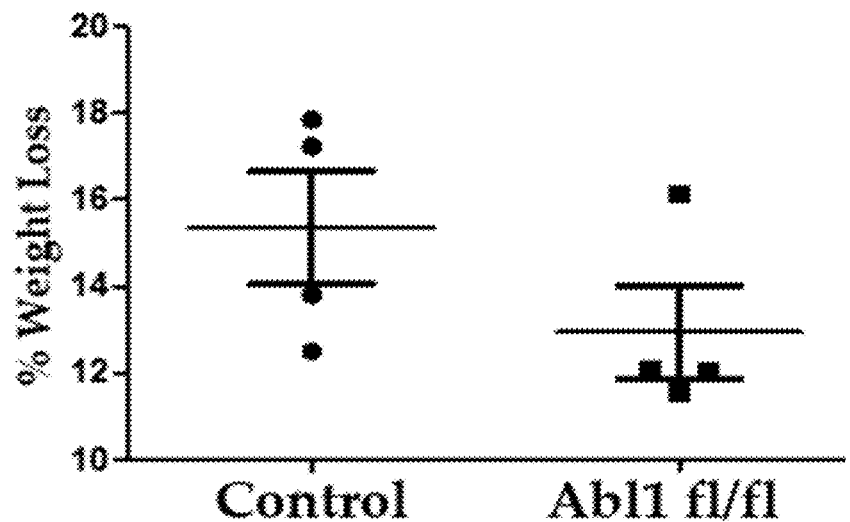
FIGS. 15A-15B show that loss of Abl1 in CC10 (Scgb1a1)-CreERT; Rosa26-fGFP mice leads to expansion of GFP+ SPC+ cells following exposure to PR8-influenza.
Figure 15B:
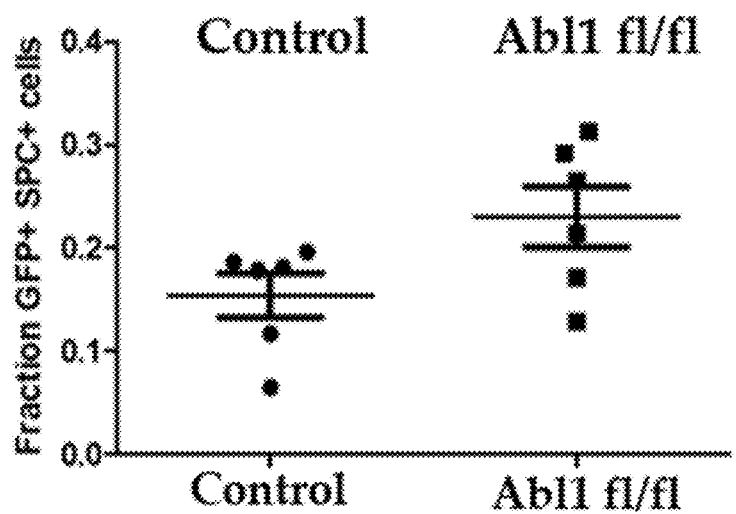

The phenotypes elicited by the murine-adapted H1N1 (PR8) influenza A strain (Kumar P A, et al. (2011) Cell. 147(3):525-38) in wild-type and Abl1 conditional knockout mice (Scgb1a1 driver) were also evaluated. While the full extent of viral induced injury manifests at a different timescale (1-2 weeks) compared to the *S. aureus* pneumonia (1-3 days), remarkably, there were significant increases in the proportion of GFP+ SPC+ cells at the same time point (72 hours) after injury in Abl1 knockout mice compared wild-type control mice (FIG. 15A-15B).

Thus, data from all three employed injury models—*S. aureus*, *S. pneumoniae*, and PR8-influenza induced injury—demonstrate that conditional knockout of Abl in Scgb1a1+ cells leads to their expansion, promotes lung regeneration, and accelerates mouse recovery after injury.

Discussion

Respiratory pathologies are the third leading cause of death in the industrialized world and with the emergence of resistant bacterial strains, there is an urgent need to identify novel therapies for use in combination with antibiotics and supportive care. Here, the Abl kinases were identified as a promising therapeutic target to promote alveolar epithelial regeneration following lung injury. Previous studies showed that distal lung epithelium, including Type I and Type II AECs, can be derived from a population of SCGB1A1+ SPC+ cells. During lung development, these cells have been identified as a putative cell-type of origin for both Type I and Type II AECs. There is evidence that a rare population of these putative "bronchioalveolar stem cells" exists in the adult lung and resides at the BADJ.

Accordingly, it was found herein that in wild-type and/or vehicle control treated mice, normal regeneration of lung alveolar epithelium involves expansion (from <5% to 10-15%) of a small pool (<1 cell per BADJ) of SCGB1A1+ SPC+ cells originating at the BADJ with complete recovery taking about one week. Another recent study showed expansion of this population of cells 11 to 17 days after bleomycin or influenza-induced lung injury. Surprisingly, genetic or pharmacologic inactivation of Abl kinases was found to promote a dramatic expansion (<5% to 25-50%) of airway cells positive for Scgb1a1 or SOX2 that co-express the SPC Type II alveolar marker by 24 hours following S. aureus-induced injury and as early as 6 hours following S. pneumoniae-induced injury. Further, Abl1 genetic inactivation specifically in Scgb1a1+ expressing cells mobilizes a large pool of Scgb1a1+ cells from the bronchioles, that are not appreciably involved in regeneration of the alveolar epithelium in wild-type mice. Cell proliferation was detected within four hours after pathogen-induced injury in Abl1-deficient mice, followed by a wave of differentiation (24-72 hours) of an expanded pool of SCGB1A1+ secretory cells within the bronchiole, leading to dramatic expansion of double-positive SCGB1A1+ SPC+ cells at sites of injury, followed by enhanced alveolar regeneration compared to wild-type mice. The rapid timeline of regeneration observed in Abl -deficient mice is relevant because S. aureus and S. pneumoniae infections are associated with progression to sepsis and multi-organ system failure, and early intervention is key in reducing mortality in these patients. In fact, early antibiotic treatment within the first 1-6 hours is the only proven intervention to reduce mortality, highlighting the importance of early intervention. No effect of Abl1 inactivation in SCGB1A1 cells on immune cell responses and susceptibility to bacterial infection was found compared to wild-type mice. Both genetic and pharmacologic inactivation of Abl kinases elicited rapid recovery following pathogen-induced injury and enhanced regeneration of the alveolar epithelium.

Genetic inactivation of Abl1 in Scgb1a1+ cells was found to not only promote expansion of SCGB1A1+ SPC+ cells, but also to enhance regeneration of RAGE+ Type I alveolar epithelium within three days after injury. These data suggest that inactivation of Abl kinases promotes expansion of SCGB1A1+ SPC+ cells, which indirectly leads to regeneration of Type I AECs following injury. The absence of GFP+ (Scgb1a1 driver) RAGE+ cells at day 3 post S. aureus-induced injury suggests that the double-positive SCGB1A1+ SPC+ cells are not likely to directly differentiate into Type I AECs to regenerate the alveolar epithelium. The fact that small clusters of GFP+ RAGE+ cells were detected at day 30 suggested that epigenetic silencing was unlikely the reason. It is more likely that Type I AEC regeneration occurs through the differentiation of Type II AECs locally at sites of injury induced by the expansion and mobilization of SCGB1A1+ SPC+ cells. Alternatively, the double positive SCGB1A1+ SPC+ cells may function to activate stromal cells at sites of injury to promote regeneration of Type I AECS from Type II alveolar cells. In this regard, signaling by bone morphogenetic protein-4 (BMP4) was shown to regulate alveolar progenitor cell proliferation and differentiation, in part by targeting stromal cells in the alveolar stem cell niche.

The finding that inactivation of Abl kinases promotes regeneration of the alveolar epithelium following pathogen-induced injury uncovers a previously unappreciated deleterious role for activation of Abl kinases following lung injury. The activity of Abl kinases is required for normal mouse development, as genetic inactivation of Abl1 results in perinatal lethality. Inhibition of Abl kinases with pharmacological agents in healthy adult mice does not produce deleterious effects, thereby suggesting that endogenous Abl kinases are not required for normal cellular homeostasis in the adult. Abl kinases are hyperactive in BCR-ABL-positive leukemia, some solid tumors, as well as in response to inflammation, DNA damage, oxidative stress, and in various pathologies. Abl kinase inhibitors have beneficial therapeutic effects for the treatment of human leukemia, metastatic tumors in mice, as well as pathologies linked to inflammation and neurodegeneration. The consequences of Abl activation on cell proliferation are cell context-dependent. Whereas activation of the Abl kinases promotes cell proliferation in leukemia cells, some solid tumors, and multiple cell types stimulated with growth factors, Abl1 activation is anti-proliferative in the response to DNA damage and Abl2 negatively regulates myoblast proliferation in mice.

Abl kinases regulate various downstream targets, some of which have been shown to play a role the regulation of lung epithelial cells following injury. These include transcriptional co-activators of the Hippo (Yap1, Taz) and Wnt (β-catenin) signaling pathways, both of which have been implicated in alveolar regeneration. The Hippo pathway regulates organ development, and Yap1 activation regulates mechanical-tension-induced pulmonary alveolar regeneration as well as airway regeneration following exposure to naphthalene. Functional interactions among Abl1, Yap1 and Taz have been reported in development, cancer and the cellular response to damage. Activation of Abl1 in response to DNA damage was reported to promote activation of a pro-apoptotic program mediated by Yap1. Abl kinases were recently shown to regulate osteoblast differentiation and lung adenocarcinoma metastasis by regulating stabilization of the Taz transcriptional co-activator.

Figure 16A:
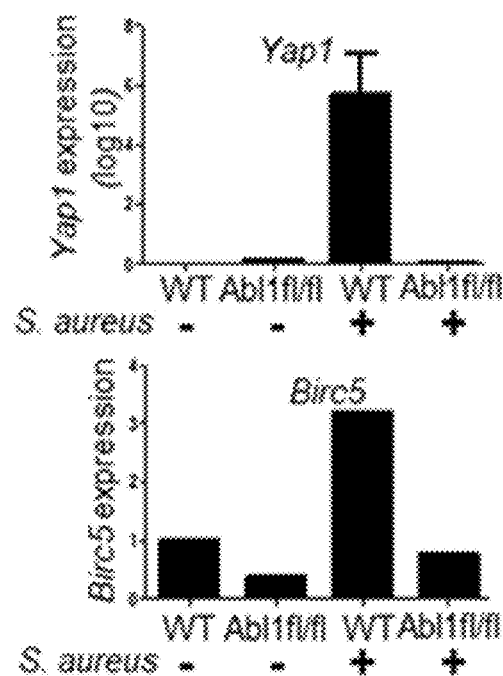
FIGS. 16A-16B show inactivation of Abl kinases induces decreased phosphorylation of Yap1 and downregulation of Yap1 transcriptional targets following *S. aureus* exposure.
Figure 16B:
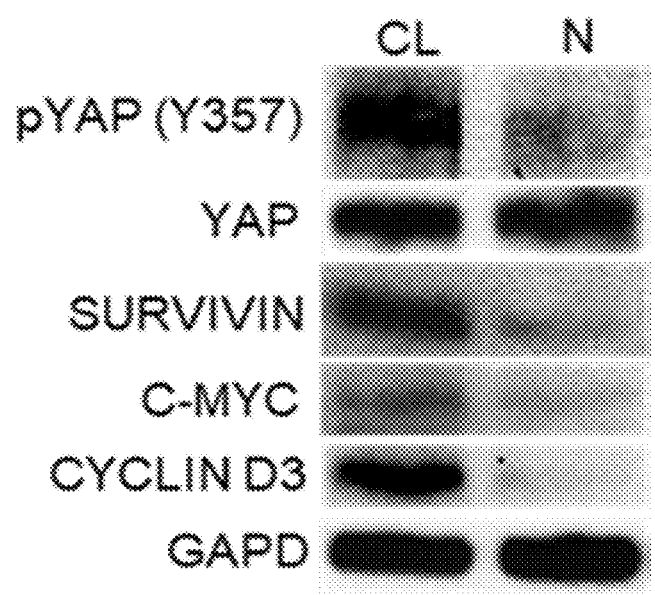

GFP+ cells were isolated from the lungs of CC10 (Scgb1a1)-CreER; Rosa26-fGFP mice through FACS sorting. It was found that loss of Abl1 in CC10 (Scgb1a1)-CreERT; Rosa26-fGFP mice results in decreased YAP1 mRNA expression and decreased phosphorylation of YAP at its Y357 site in isolated GFP+ cells (FIG. 16A). Primary HBECs were pre-treated with the Abl kinase inhibitor, nilotinib (N), 24 hours prior to exposure to S. aureus. It was also found decreased transcript and protein expression of downstream transcriptional targets of YAP, including Birc5 (the gene that encodes the protein, Survivin), c-Myc, and Cyclin D3 (FIG. 16B). Transcriptional targets of Yap1 have been implicated in processes including apoptosis (BAX, PUMA) and proliferation (CTGF, c-Myc). In modulating expression of these targets, Abl kinase inhibition may be promoting both a protective and regenerative response in epithelial cells following injury. Furthermore, targeting of phosphorylated Yap11 may promote its cytosolic sequestration through the 14-3-3-β-catenin complex. This may also promote enhanced differentiation of secretory and basal cells in the lung following injury.

Figure 17:
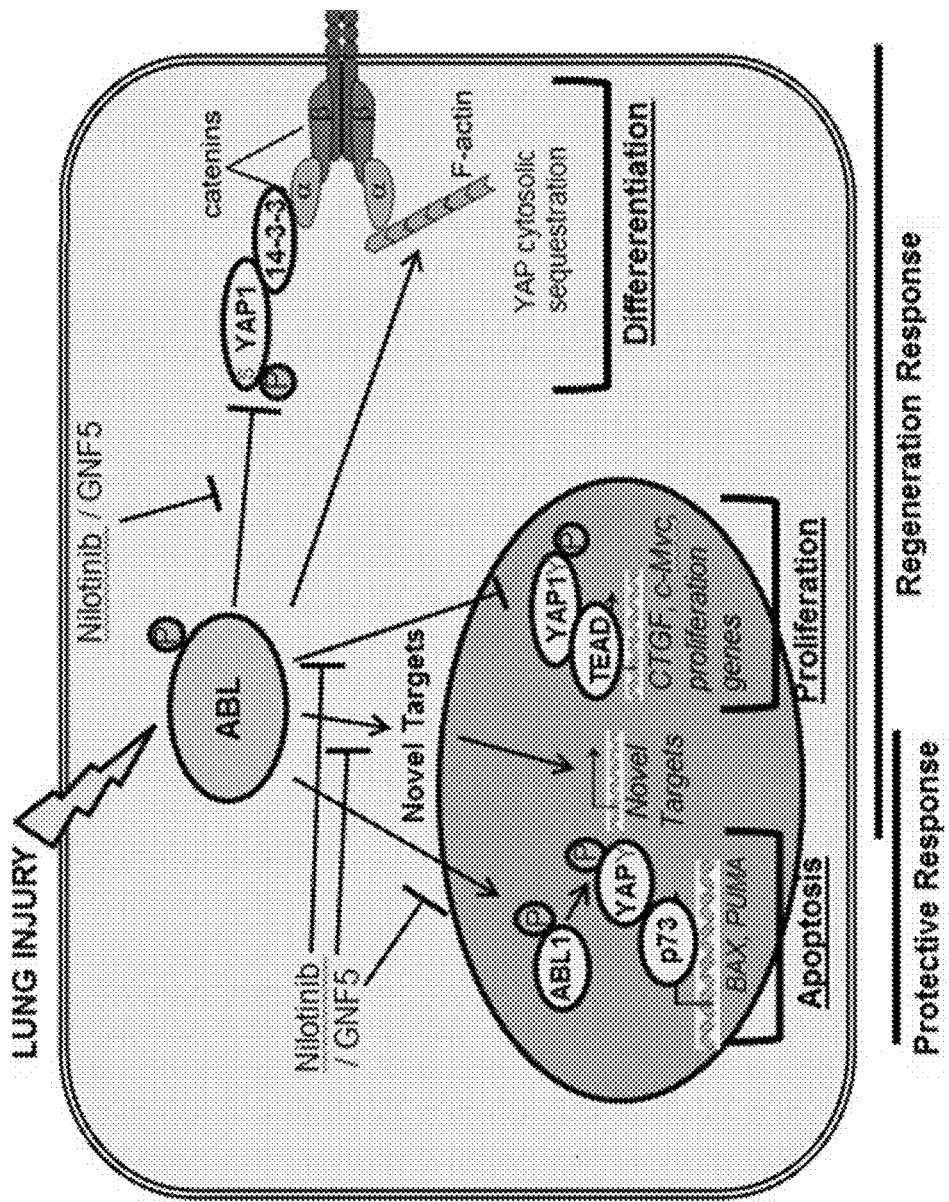
FIG. 17 is a schematic of a model for Abl-mediated regulation of Yap1 signaling following injury in lung epithelial cells.

Because inhibitors of Yap1 demonstrate high toxicity profiles, modulation of Yap1 through Abl kinase inhibition may represent an effective way to target the Hippo pathway and its vital roles in organ regeneration in vivo (FIG. 17).

Here, it is reported that loss of Abl1 specifically in SCGB1A1-expressing cells leads to a significant increase in the proliferation and differentiation of bronchiolar epithelial cells, resulting in dramatic expansion of a SCGB1A1+ airway cell population that co-expresses SPC, a marker for Type II alveolar cells, that promotes alveolar regeneration following bacterial pneumonia. These findings revealed that inactivation of Abl kinases promotes lung epithelial cell regeneration in mouse models of pneumonia induced by *S. aureus, S. pneumonia*, and influenza virus. Furthermore, treatment with an Abl-specific allosteric inhibitor enhanced regeneration of the alveolar epithelium and promoted accelerated recovery of mice following pneumonia. These data suggest that FDA-approved inhibitors for the treatment of BCR-ABL+ leukemias can be repurposed for the treatment of lung injury. In fact, several case reports have demonstrated that treatment of leukemia patients with imatinib (which inhibits not only ABL kinases but the PDGFR and other kinases) resulted in resolution of pulmonary symptoms such as acute interstitial pneumonia or drug-induced pneumonitis. These studies have focused on lung injury induced by *S. pneumoniae* and *S. aureus* which target the alveolar epithelium resulting in necrotizing pneumonias, and indicate that inactivation of Abl kinases can be exploited as a therapeutic strategy to promote lung regeneration in response to injury induced by a variety of toxins and other pathogens. These include destructive agents such as chlorine gas and influenza virus, as well as non-destructive lung injury such as drug-induced pneumonitis or atypical pneumonia. The findings of regeneration in mice with Abl specific inactivation following pathogen-induced injury, together with case reports of patients treated with imatinib showing improved pulmonary function following drug-induced pneumonitis, suggest that Abl inhibitors might be used to promote repair and/or regeneration of the lung in a wide variety of lung pathologies.

Figure 18A:
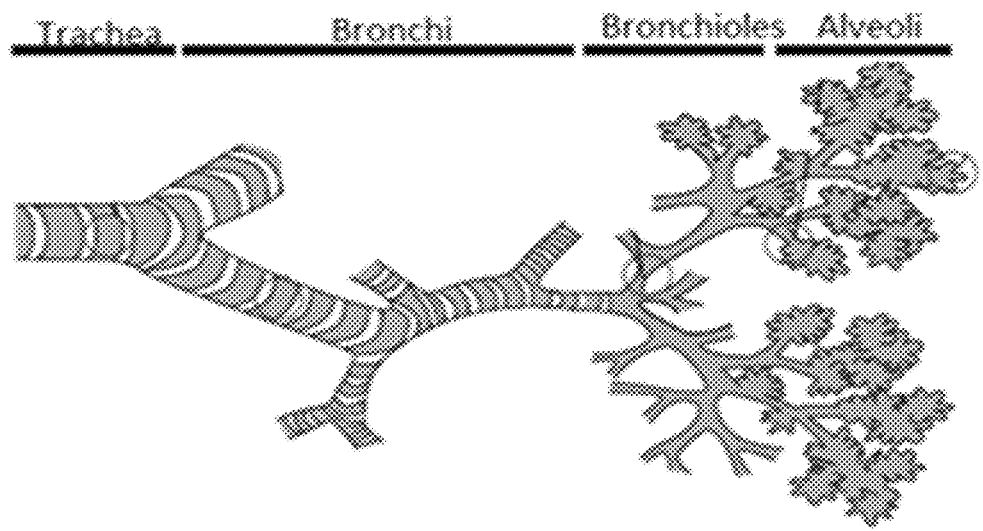
FIGS. 18A-18B show schematics of the tracheo-bronchial tree and alveolar region of the lung.
Figure 18B:
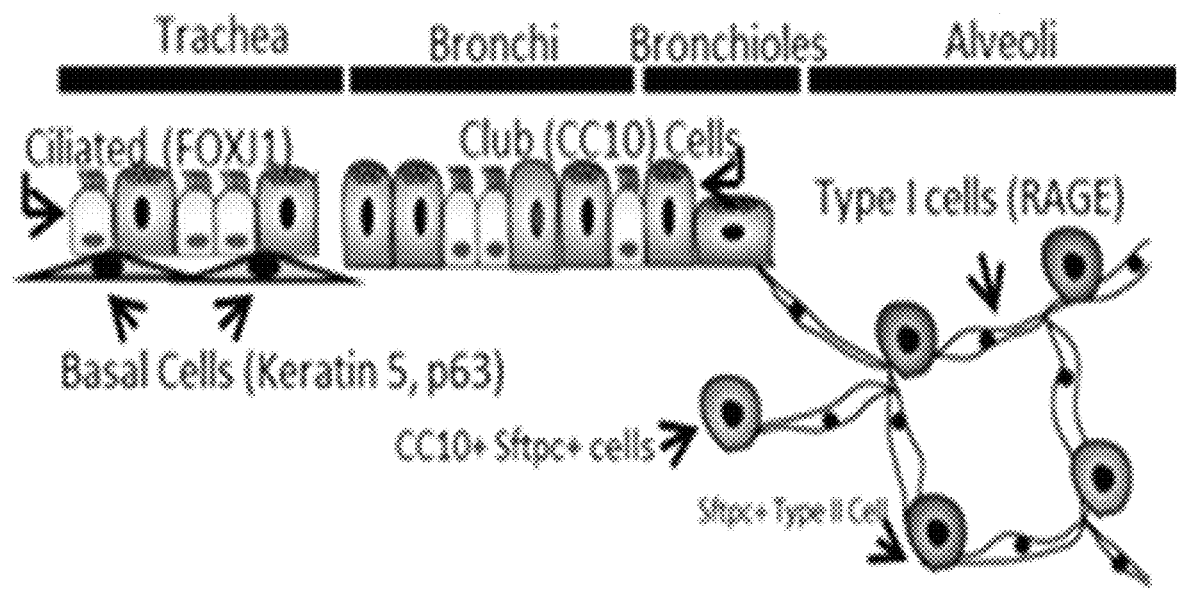

Example 10: Abl Kinase Inhibition Promotes Basal Cell Differentiation in Primary Human Bronchial Epithelial Cells Conducting airways can be compartmentalized along the proximal-distal axis into structurally distinct domains: trachea, bronchi, and bronchioles (FIG. 18A). The upper airways are lined by pseudostratified or columnar epithelium consisting of basal, ciliated and secretory cell types including Club (Clara) and goblet cells (FIG. 18B).

Despite significant progress made in identifying distinct stem/progenitor cell populations in the airway, little is known regarding the identity of signaling networks that might be effectively targeted within these cell populations to promote recovery from injury. Moreover, there are no approved drugs that directly prevent or reverse epithelial cell damage following injury. A previously unknown role for the Abl kinases in the regulation of regeneration of airway epithelium after injury was described above. Together with the findings described in Examples 1-9 showing a role of Abl kinases in alveolar regeneration, these data on Abl-regulated airway regeneration suggest that available Abl kinase inhibitors, which have been used for treating leukemia, might be re-purposed to treat lung epithelial damage induced by exposure to pathogens and toxins.

Figure 19A:
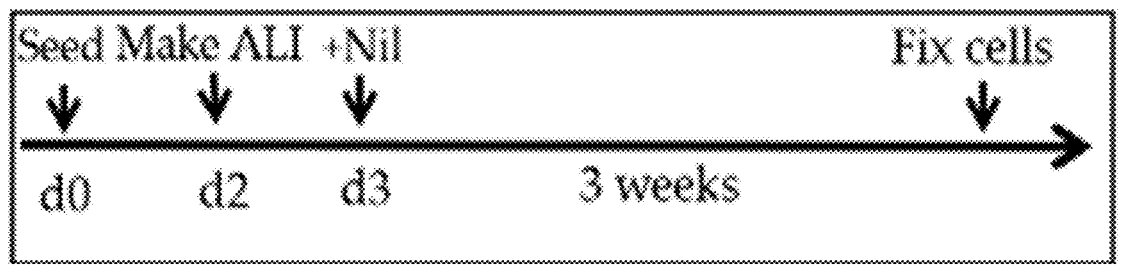
FIGS. 19A-19D show inhibition of Abl promotes differentiation of basal cells to luminal cells.
Figure 19B:
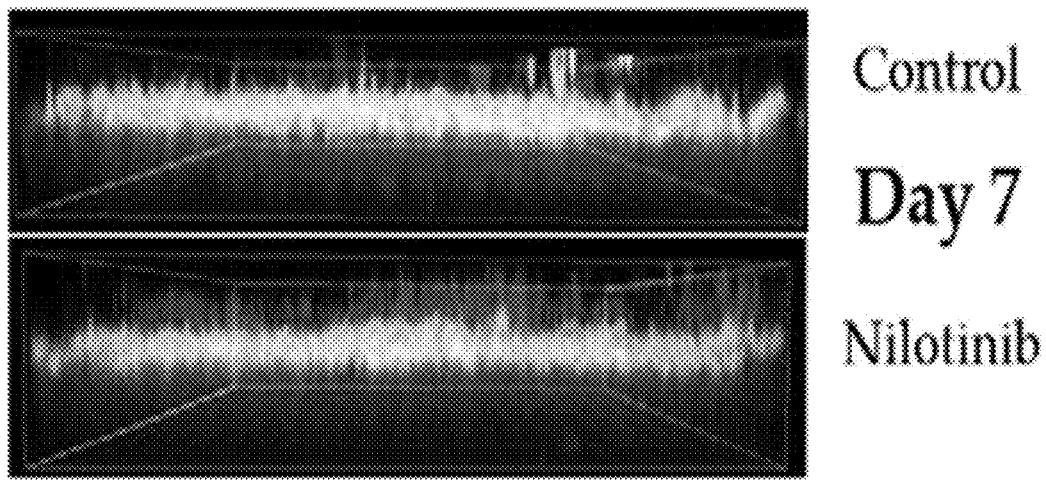
Figure 19C:
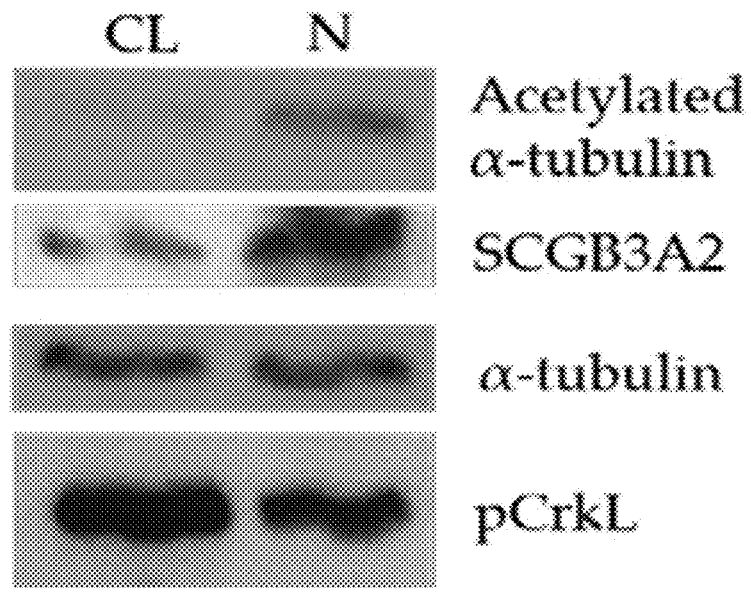
Figure 19D:
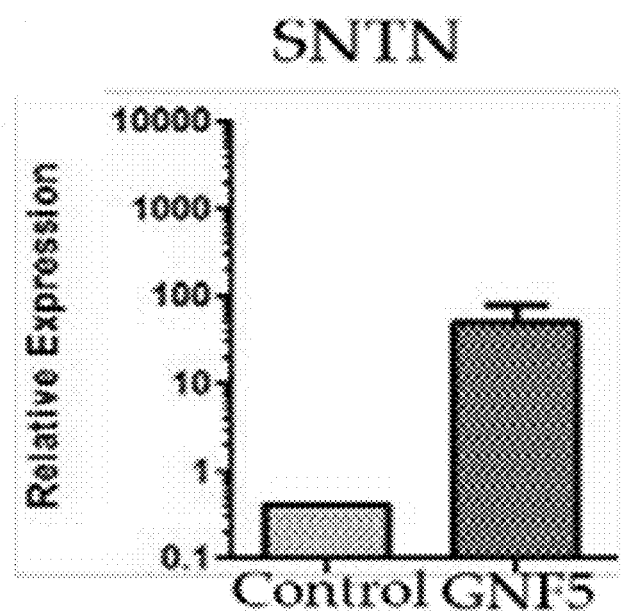

First, the role of Abl kinases in basal cell differentiation in primary human bronchial epithelial cells (HBECs) in air-liquid interface (ALI) cultures was examined. Basal cells were isolated from human donor lungs and plated on polyester transwell inserts at passage 1. Once the cells were 100% confluent (3-4 days after plating), media from the top chamber of the transwell insert was removed to promote differentiation of the basal cells into a pseudostratified ciliated epithelium (FIG. 19A). Remarkably, it was found that, whereas untreated cells normally take 3-4 weeks to form a fully-differentiated pseudostratified ciliated epithelium, basal cells treated with the Abl kinase inhibitors, nilotinib or GNF5, fully differentiate in less than 14 days and express luminal cell markers within 7 days (FIG. 19B-D). Among these are acetylated α-tubulin and SNTN (ciliated cell marker) and SCGB3A2 (secretory cell marker) (FIG. 19C).

Figure 20:
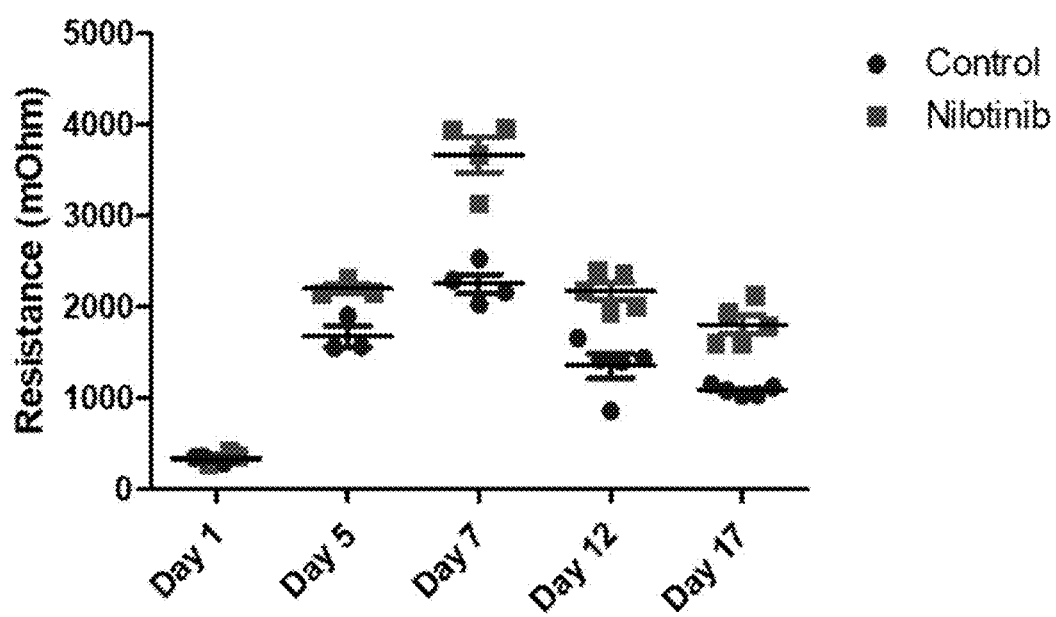
FIG. 20 is a graph of transepithelial electrical resistance assays in ALI cultures of primary HBECs showing an increased resistance across a monolayer of cells treated with an Abl inhibitor, nilotinib, compared to vehicle control-treated cells (n=3-5 human patients per group, each run in duplicate).

Importantly, transepithelial electrical resistance assays showed that the increased differentiation in cells treated with the Abl inhibitor results functionally in increased resistance and decreased cell barrier permeability within 5 days (FIG. 20). Increased resistance across the pseudostratified ciliated lung epithelium persists even after untreated cells fully differentiate three weeks after plating. Thus, inhibition of the Abl kinases in 3D ALI cultures of primary HBECs promotes basal cell differentiation and enhances barrier function.

Figure 21A:
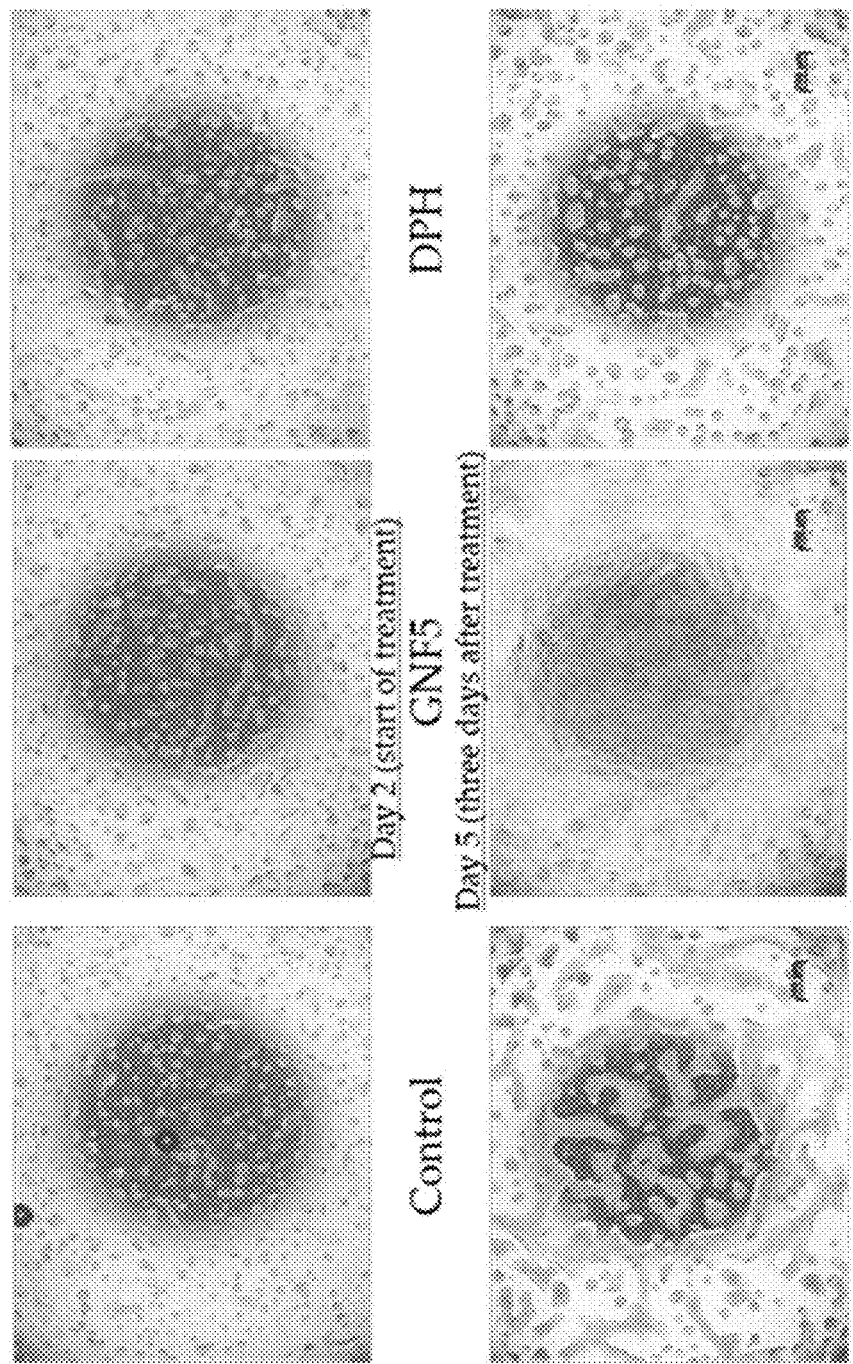
FIGS. 21A-21B show inhibition of Abl promotes basal cell proliferation and differentiation in bronchosphere cultures.
Figure 21B:
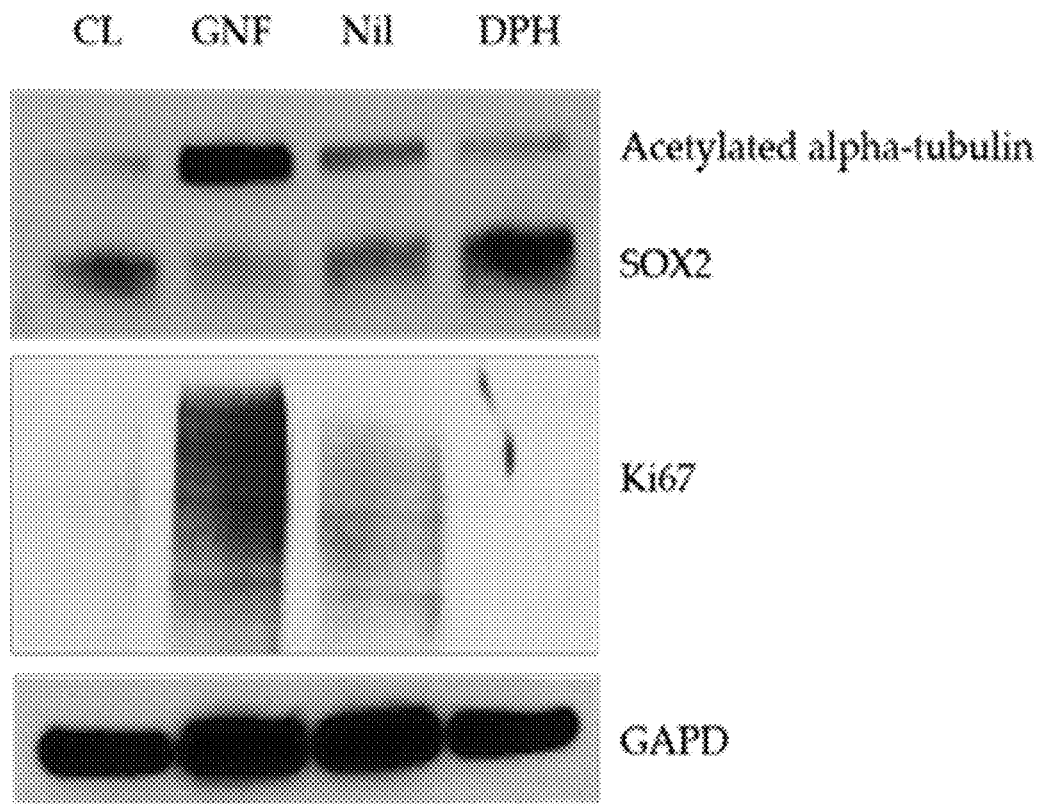

The effect of Abl kinase inhibition on the development of bronchospheres in a 3D Matrigel culture assay was also evaluated. Basal cells were cultured in Matrigel at passage 1 and treated with vehicle control, the Abl kinase inhibitor, GNF5, or the Abl kinase activator, DPH, for three days starting two days after plating the cells. It was found that Abl kinase inhibition promoted basal cell proliferation and differentiation (FIG. 21A). Isolation and lysis of bronchospheres showed an increase in expression of the ciliated cell marker, acetylated α-tubulin, and a corresponding decrease in the basal cell marker, SOX2 (FIG. 21B). In addition, an increase in protein expression of the proliferation marker, Ki67, in cells treated with the Abl kinase inhibitors, GNF5 or nilotinib, compared to untreated cells was found (FIG. 21B). Importantly, treatment with the Abl allosteric activator, DPH, reduced bronchosphere growth and differentiation as determined by decreased expression of acetylated α-tubulin and increased expression of the basal cell marker, SOX2 (FIG. 21A-21B).

Taken together, the data derived from in vitro ALI cultures and bronchosphere assays strongly suggest that Abl kinase inhibition plays an important role in basal cell proliferation and differentiation.

Figure 22:
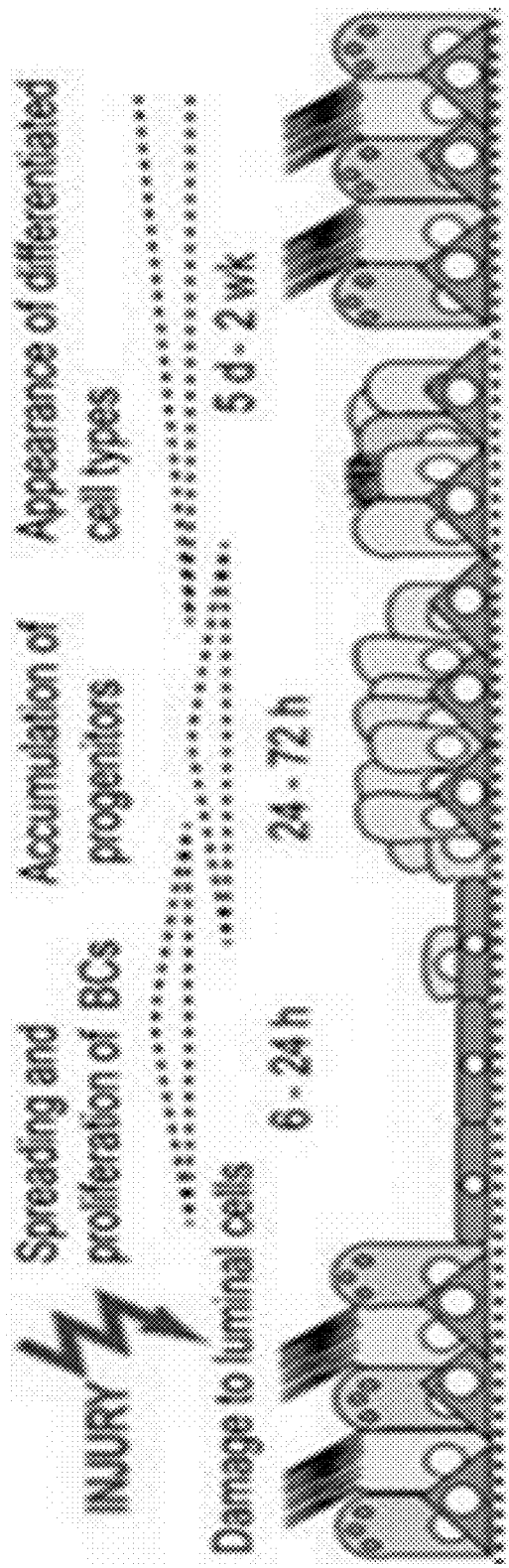
FIG. 22 is a schematic representation of a timeline of in vivo basal cell differentiation in the mouse airway epithelium following SO2 injury. Following injury-induced depletion of secretory and ciliated cells, the remaining basal cells differentiate to regenerate the mucociliary epithelium (Xia Gao, et al. J Cell Biol 2015; 211:669-682).

Example 11: Abl Kinase Inhibitor Protects Luminal Cells from Sulfur Dioxide Induced Injury To evaluate whether the Abl kinases promote basal cell differentiation in vivo, the sulfur dioxide (SO2) injury model was employed (FIG. 22). SO2 inhalation elicits cell death and sloughing of luminal (ciliated and secretory) cells, leaving a layer of intact basal cells in the tracheobronchial region (Zuo W, et al. (2015) Nature. 517(7536):616-20). Previous studies have shown that after SO2-induced destruction and sloughing of luminal cells, the surviving basal cells (Krt5+) proliferate to generate progenitor cells (Krt8+) that accumulate and subsequently undergo differentiation into ciliated (acetylated alpha-tubulin+) and secretory (Scgb1a1+) cells (5 days to 2 weeks after injury) (Hogan B L, et al. (2014) *Cell stem cell*, 15(2): 123-38). This well-defined model of airway injury and regeneration has been employed to identify signaling pathways that promote proliferation and differentiation of the lung epithelium after injury (Hogan B L, et al. (2014) *Cell stem cell*, 15(2):123-38, Tadokoro T, et al., (2014) *Proceedings of the National Academy of Sciences of the U.S.A.*, 111(35):E3641-9).

In contrast to SO2-treated control mice, a mostly intact mouse airway epithelium was found within 24 hours after SO2 injury in mice pre-treated with GNF5. The tracheas of SO2-treated control mice had complete ablation of the luminal cells.

Figure 23A:
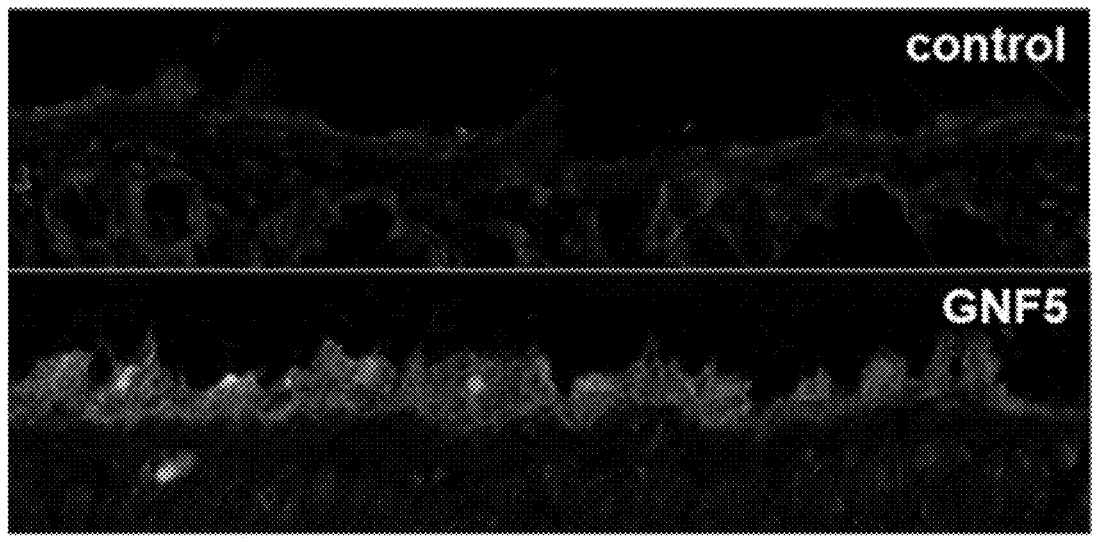
FIGS. 23A-23B show pre-treatment of mice with an Abl kinase inhibitor protects luminal cells from sulfur dioxide induced injury.
Figure 23B:
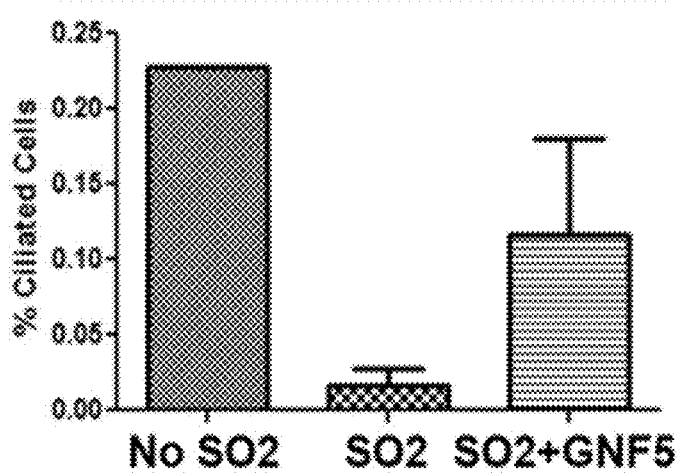

Immunofluorescence staining of sections of whole tracheas showed preservation of the pseudostratified epithelium in mice treated with GNF5 compared to untreated mice after SO2 injury (FIG. 23A). Staining for Scgb1a1+ Club cells and acetylated α-tubulin+ ciliated cells showed a mostly intact layer of secretory cells and some ciliated cells in GNF5-treated mice 24 hours after SO2 exposure (FIGS. 23A-23B). This result suggests a protective and/or a regenerative role for Abl kinase inhibition following SO2 exposure.

Example 12: Abl Kinase Inhibition Promotes Basal Cell Proliferation and Differentiation after Sulfur Dioxide Induced Injury To distinguish between protective and regenerative effects of Abl kinase inhibition, the expression of various proliferation and differentiation markers in the mouse trachea after injury was evaluated. 24 h following SO2 induced injury, basal cells in the trachea of mice treated with GNF5 showed a significant increase in the expression of Ki67 in the basal cells of mice treated with GNF5 compared to untreated mice 24 hours after exposure to SO2. Furthermore, three days after injury, SO2 induced injury, H&E staining of tracheas of mice treated with GNF5 demonstrated stratified ciliated epithelium, consistent with increased proliferation and differentiation, while tracheas of untreated mice given SO2 (middle) were lined with a non-ciliated simple columnar epithelium. Whereas untreated mice presented with a simple, columnar, non-ciliated epithelium showing initial stages of airway regeneration, mice treated with GNF5 presented with a stratified, columnar, ciliated epithelium that had almost completely recovered from injury.

These findings reveal a role for Abl kinases in airway epithelial cell regeneration after injury. The striking discovery that inhibition of Abl kinases promotes basal cell proliferation and enhances differentiation supports therapeutic targeting of Abl kinases to promote regeneration after airway damage.

Example 13: Abl Kinase Inhibition Promotes Early Differentiation of Krt5+ Basal Cells to a Krt8+ Intermediate Progenitor Cell Type The mechanism by which Abl kinase inhibition promotes differentiation of basal cells to luminal cells was investigated. The process of differentiation of basal cells to luminal cells involves differentiation of Krt5+ basal cells to an intermediate cell type (Krt8+) followed by differentiation to either ciliated (acetylated α-tubulin) or secretory (Scgb1a1+/CC 10+) cells.

Figure 24:
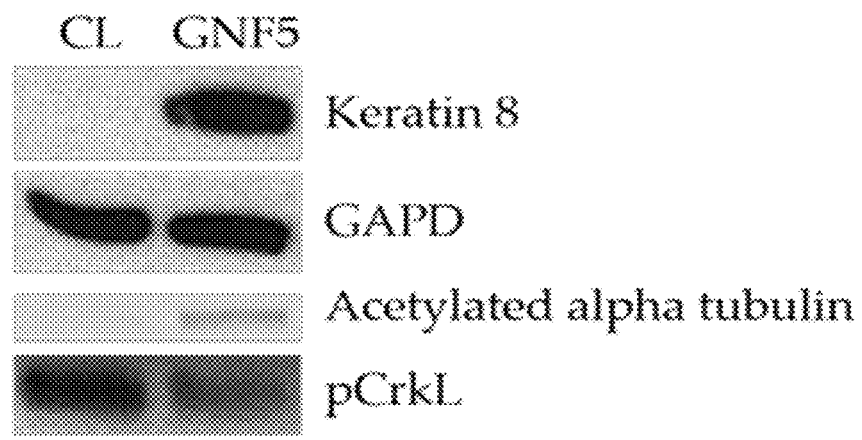
FIG. 24 is an immunoblot with the Krt8 antibody showing a significant increase in Krt8 expression in primary HBECs treated with GNF5 as compared to vehicle control. Phosphorylated CrkL (pCrkL), a downstream target of the Abl kinases, is shown as a surrogate marker for Abl kinase activity. GAPD protein is used for loading control (n=2 human patients per group, each run in duplicate).

To identify whether Abl kinase inhibition promotes early (Krt5+ cells→Krt8+ cells) or late (Krt8+→acetylated α-tubulin or Scgb1a1+ cells) differentiation, a time course experiment in primary HBEC ALI cultures was conducted. Primary HBECs were plated on polyester transwell inserts and treated with vehicle control or GNF5 24 hours after plating. A significant increase in expression of Krt8 by both immunofluorescence and Western blot analysis (FIG. 24) was found, suggesting a key role of Abl kinase inhibition in early differentiation of lung airway basal cells.

Figure 25:
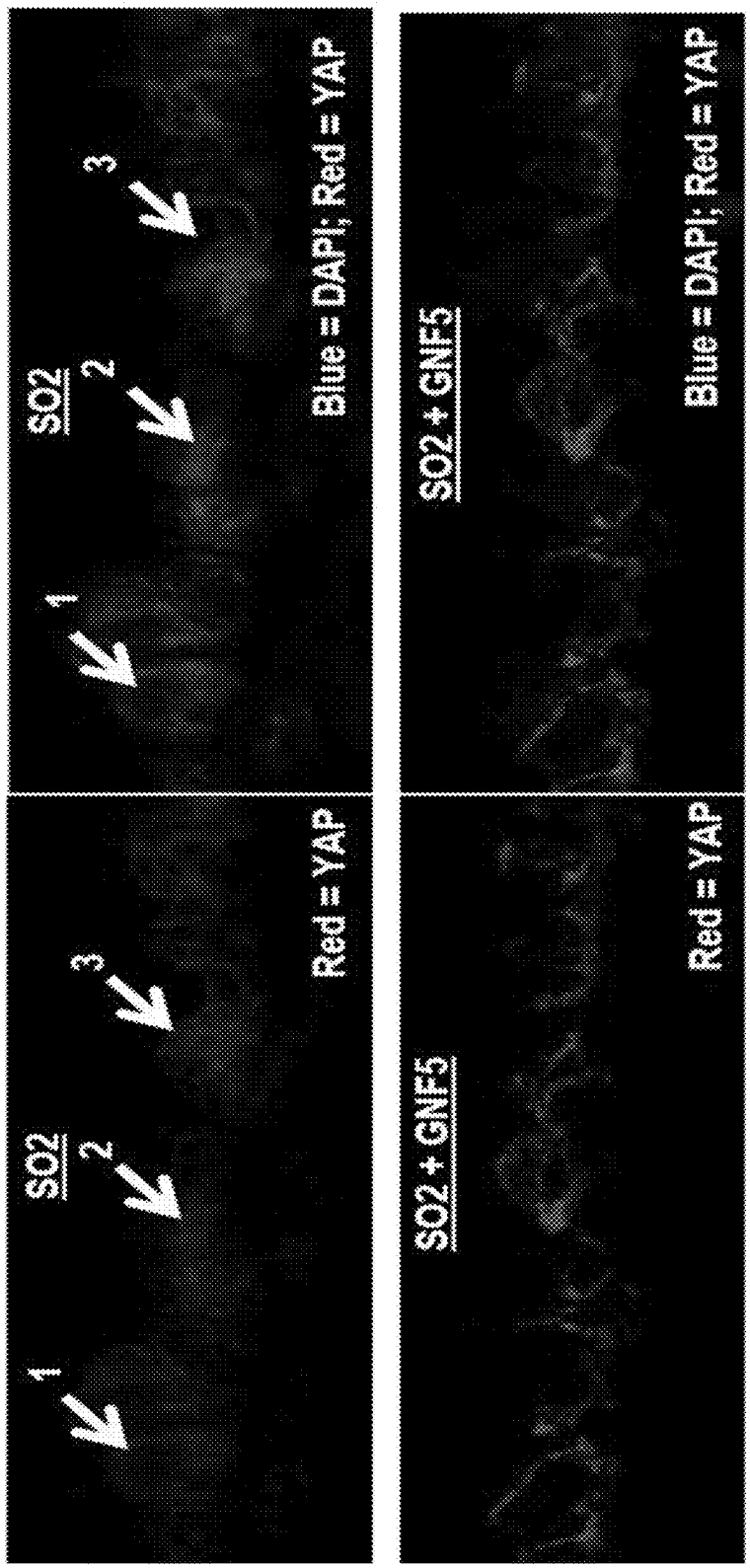
FIG. 25 is microscopy images showing that Abl kinase inhibition promotes cytoplasmic localization of Yap1 in mouse lung basal cells following sulfur dioxide induced injury.

Example 14: Abl Kinase Inhibition Promotes Cytoplasmic Localization of Yap1 to Promote Basal Cell Differentiation Following Injury Next, whether Abl kinase inhibition promotes basal cell differentiation to Krt8+ cells by affecting Yap1 signaling was investigated. Three days after SO2 injury, mouse tracheas were harvested and evaluated for Yap1 protein expression by immunofluorescence. Whereas basal cells in untreated mice demonstrated predominantly nuclear expression of Yap1, basal cells in mice treated with the Abl kinase inhibitor, GNF5, exhibited predominantly cytoplasmic localization of Yap1 (n=3 mice per group) (FIG. 25).

Discussion

The lung airway is the first line of defense against foreign agents for the lung.

Secretory, ciliated, and goblet cells function together to prevent pathogens and noxious substances from damaging airway and alveolar compartments to allow for gas exchange. Compared to distal airways and the lung parenchyma, there is a much higher turnover of cell populations in the airway, and a variety of progenitor cell populations exist to ensure airway maintenance. These include secretory (Club) and basal cells in the airway lumen and reserve cells within the submucosal glands. Despite important advances in the understanding of airway repair and regeneration, to date no targetable therapies have been devised to activate a specific progenitor population to promote regeneration after injury. In Examples 1-14, it was demonstrated that Abl kinase inhibition promotes basal cell proliferation and differentiation after injury. Targeting of the Abl kinases may substantially improve outcomes in airway pathologies such as damage following influenza or exposure to hazardous chemical agents.

It was found that following an initial proliferation phase (within 24 hours of injury in both the upper and lower airways), a switch from a proliferation phase to differentiation phase may be directed by translocation of Yap1 to the cytoplasm from the nucleus where it serves as a transcription factor for pro-proliferation genes including c-Myc, CCND3. (Cyclin D3) and CTGF.

Future studies can also be conducted in both mice treated with an Abl kinase inhibitor before exposure to sulfur dioxide as well mice treated after exposure to sulfur dioxide to differentiate between potential protective and regenerative effects of Abl kinase inhibition. That Abl kinase inhibition promoted proliferation in basal cells compared to vehicle control treated cells strongly suggests a role in regeneration of luminal cells after injury. However, Abl kinase inhibition in pre-treated mice can also prevent cell death. Indeed, both Abl kinases and Yap1 have been implicated in apoptosis pathways.

As described herein, the results uncovered a previously unknown role for the Abl kinases in the regulation of regeneration of airway epithelium after injury. Together with our findings in Examples 1-9 showing a role of Abl kinases in alveolar regeneration, these findings suggest that available Abl kinase inhibitors, which have been used for treating leukemia, might be re-purposed to treat lung epithelial damage induced by exposure to pathogens and toxins.

Example 15: Inhibition of Abl Kinases Impairs $Kras^{G12D/+}$; $p53^{-/-}$ Driven Lung Tumors To evaluate whether Abl kinases play a role in the progression of primary lung adenocarcinomas, whether pharmacological inhibition of the Abl kinases impaired tumor growth in an autochthonous $KRAS^{LSL-G12D}$; $p53^{fl/fl}$ mouse model was assessed.

Intranasal delivery of an adenovirus containing a Cre-recombinase expressing construct (Ad5-Cre) results in the activation of oncogenic KRAS and loss of p53 in infected cells.

Consequently, spontaneous lung adenocarcinomas form throughout the lung approximately 8 weeks after Adeno-Cre infection of LSL-Kras$^{G12D/+}$; p53$^{fl/fl}$ mice. Treatment with the Abl kinase inhibitor, GNF5, and/or the chemotherapeutic agent, docetaxel, was initiated once tumor formation was confirmed by μCT scans performed every two weeks starting at 8 weeks following infection. GNF5 binds specifically to the myristoyl-binding site in the kinase domain of the Abl kinases unlike the commonly used ATP-binding site inhibitors such as imatinib and nilotinib that also interact with numerous other protein kinases (Zhang J, et al., (2010) Nature. 463(7280):501-6).

Figure 26A:
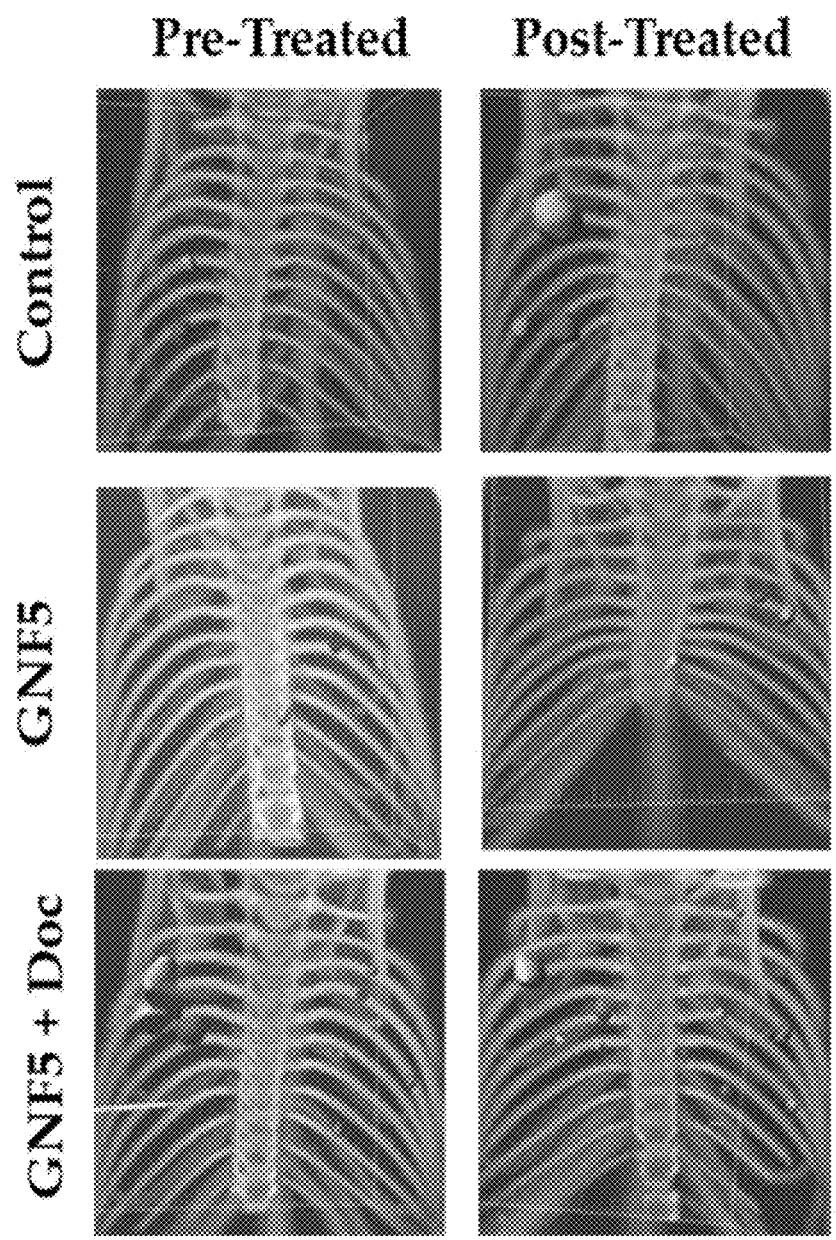
FIGS. 26A-26C show inhibition of Abl kinases impairs $Kras^{G12D/+}$; $p53^{-/-}$ driven lung tumors.
Figure 26B:
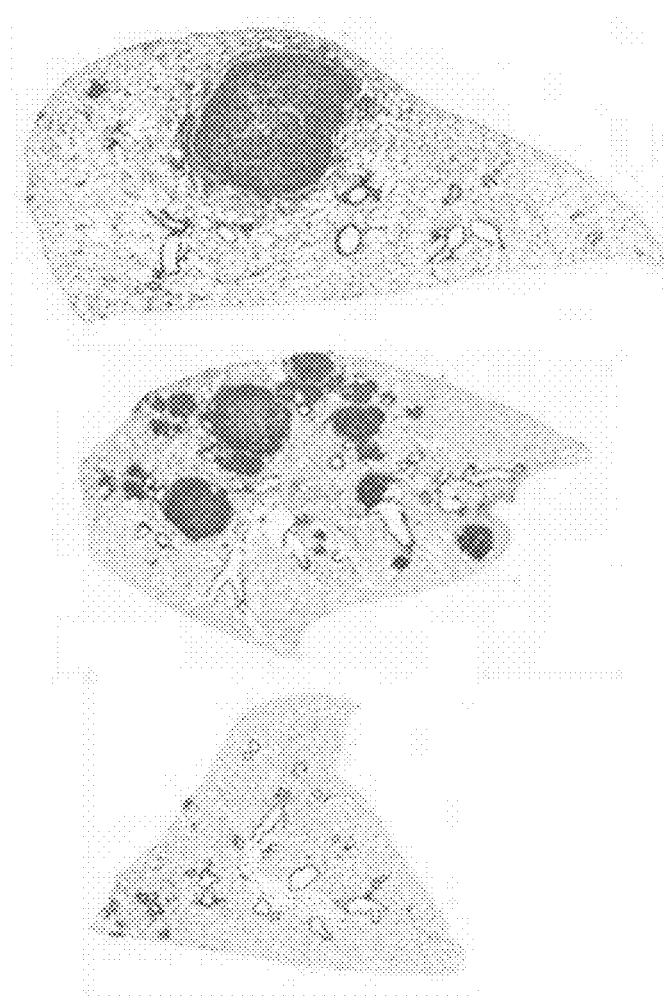
Figure 26C:
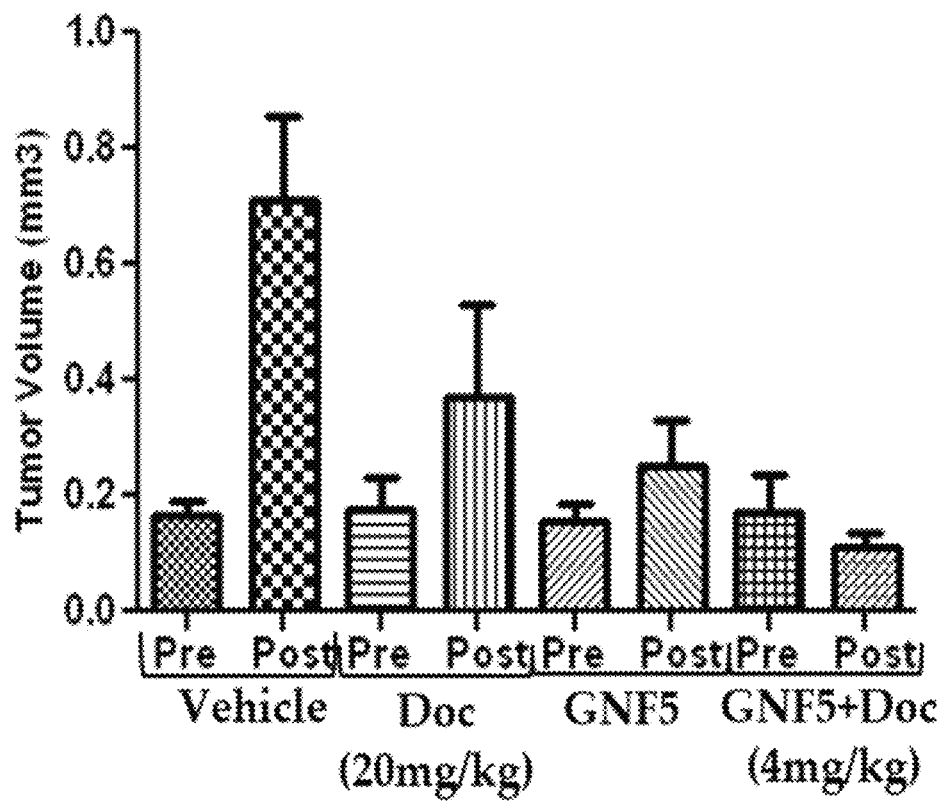

It was found that b.i.d. treatment with GNF5 or a sub-therapeutic dose of docetaxel alone slowed tumor progression (two-fold increase in tumor size over a two-week period) compared to vehicle control treated mice (four-fold increase in tumor size over a two-week period). Notably, combination treatment with both GNF5 and a sub-therapeutic dose of docetaxel decreased overall tumor size (FIGS. 26A-26C).

Example 16: Combination Treatment of an Abl Kinase Inhibitor and Docetaxel Decreases Cell Proliferation and Increases Cell Death in KRAS$^{G12D/+}$; p53$^{-/-}$ Driven Lung Tumors To evaluate the mechanism by which combination treatment of an Abl kinase inhibitor, GNF5, and docetaxel ablates lung adenocarcinomas in vivo, mouse lungs treated with vehicle control, GNF5 alone, docetaxel alone, or combination therapy were harvested two weeks after initiating treatment (10 weeks after delivery of adenovirus).

Figure 27A:
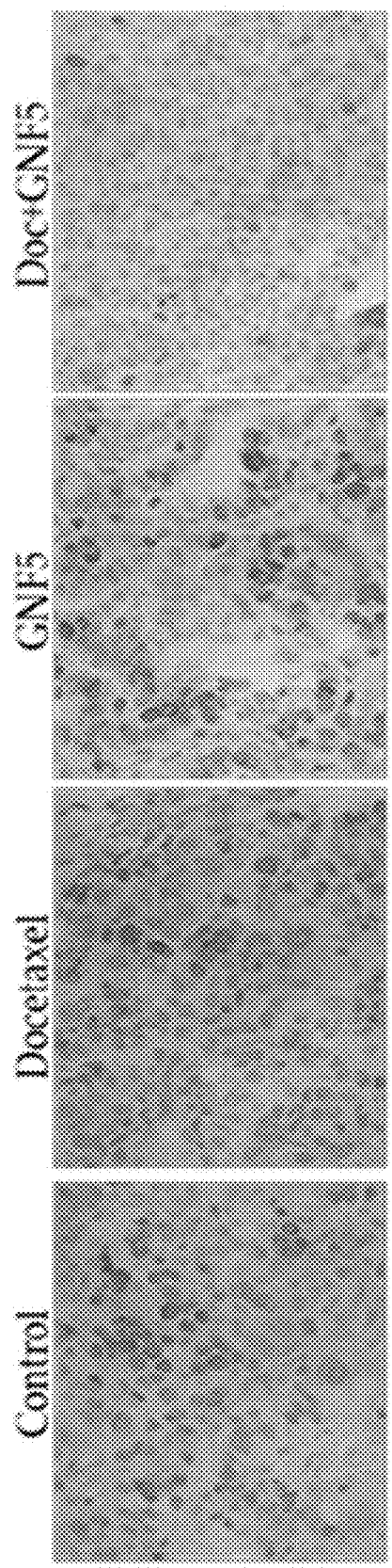
FIGS. 27A-27C show inhibition of Abl kinases decreases cell proliferation and increases cell death in $Kras^{G12D/+}$; $p53^{-/-}$ driven lung tumors. Treatments began 8 weeks after Adeno-Cre infection of Rosa26-fGFP; LSL-$Kras^{G12D/+}$; $p53^{fl/fl}$ mice. Mouse lungs were harvested at 10 weeks after Adeno-Cre infection.
Figure 27B:
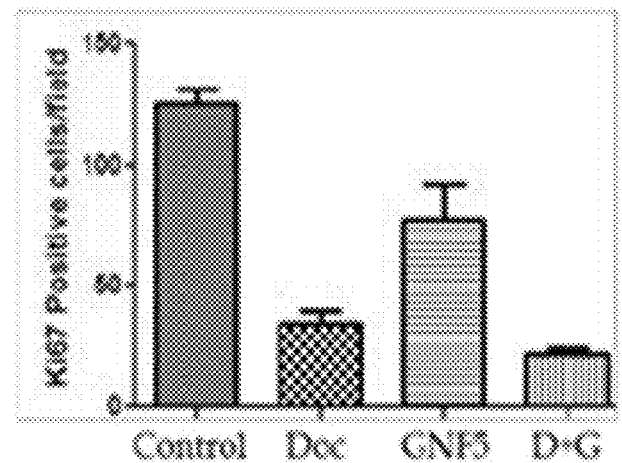
Figure 27C:
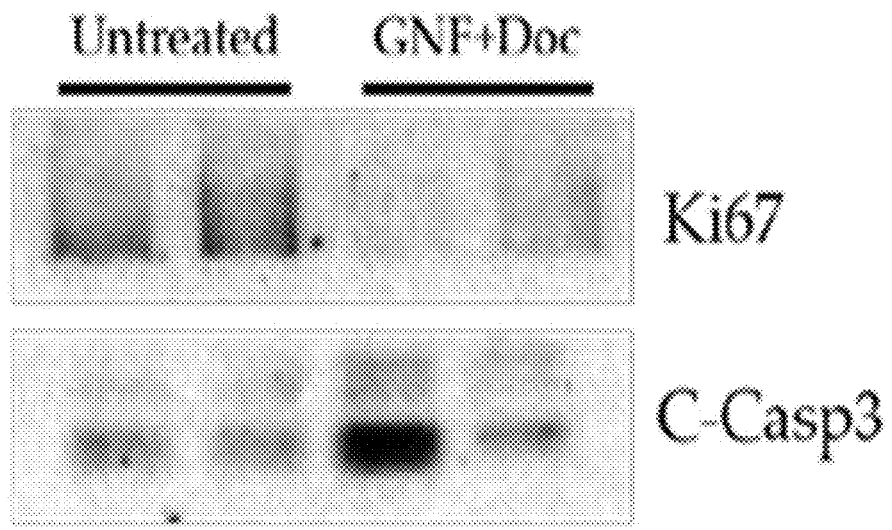

Sectioning and staining with the proliferation marker, Ki67, showed a decrease in Ki67 expression by immunohistochemistry (IHC) and immunofluorescence (IF) in double-treated mice compared to vehicle control mice or mice treated with GNF5 or docetaxel alone (FIGS. 27A-27C). To evaluate apoptosis within the tumor, KRAS$^{LSL-G12D}$; p53$^{fl/fl}$ mice were crossed with mice expressing the Rosa26-fGFP reporter allowing for isolation of GFP+ tumor cells 10 weeks after delivery of the adenovirus. Immunoblotting of protein lysate from the isolated GFP+ cells showed a significant increase in expression of cleaved caspase 3, a marker of apoptosis, in double treated mice compared to either vehicle control mice or mice treated with GNF5 or docetaxel alone (FIG. 27A).

Figure 28A:
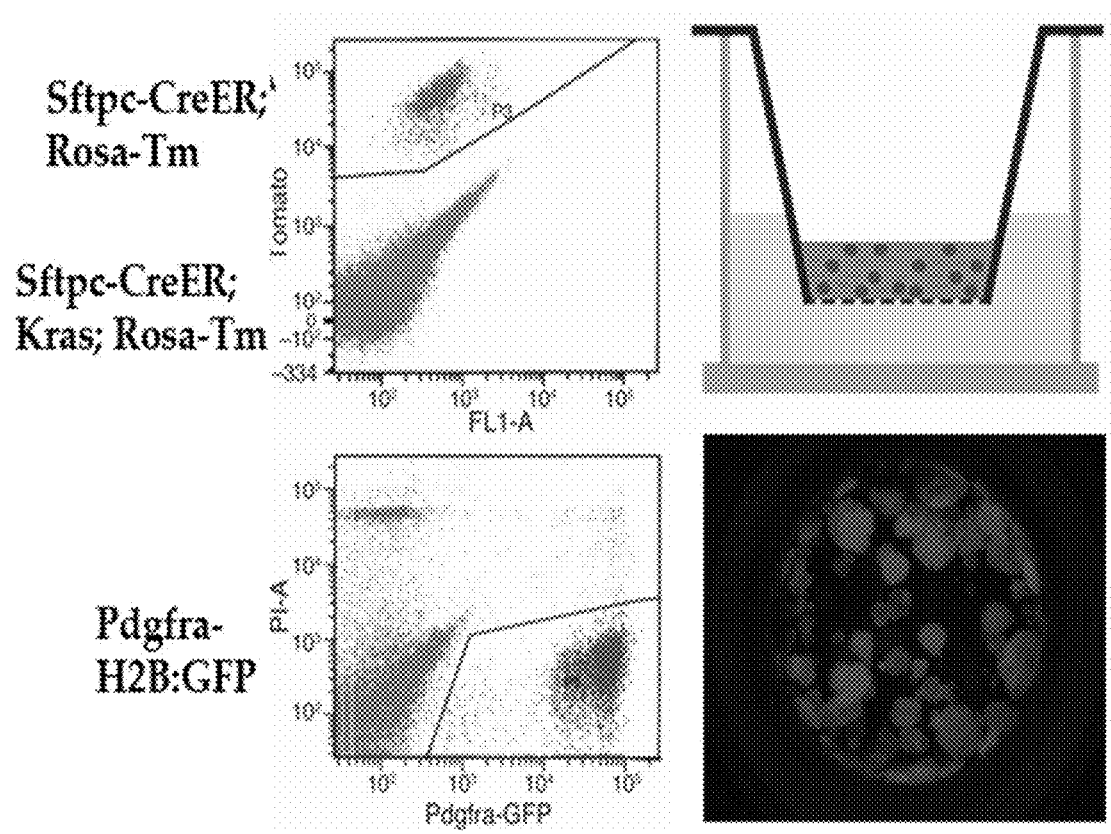
FIGS. 28A-28B show inhibition of Abl kinases sensitizes primary $Kras^{G12D/+}$; $p53^{-/-}$ derived organoid cultures to treatment with docetaxel in 3D tumor sphere assays.
Figure 28B:
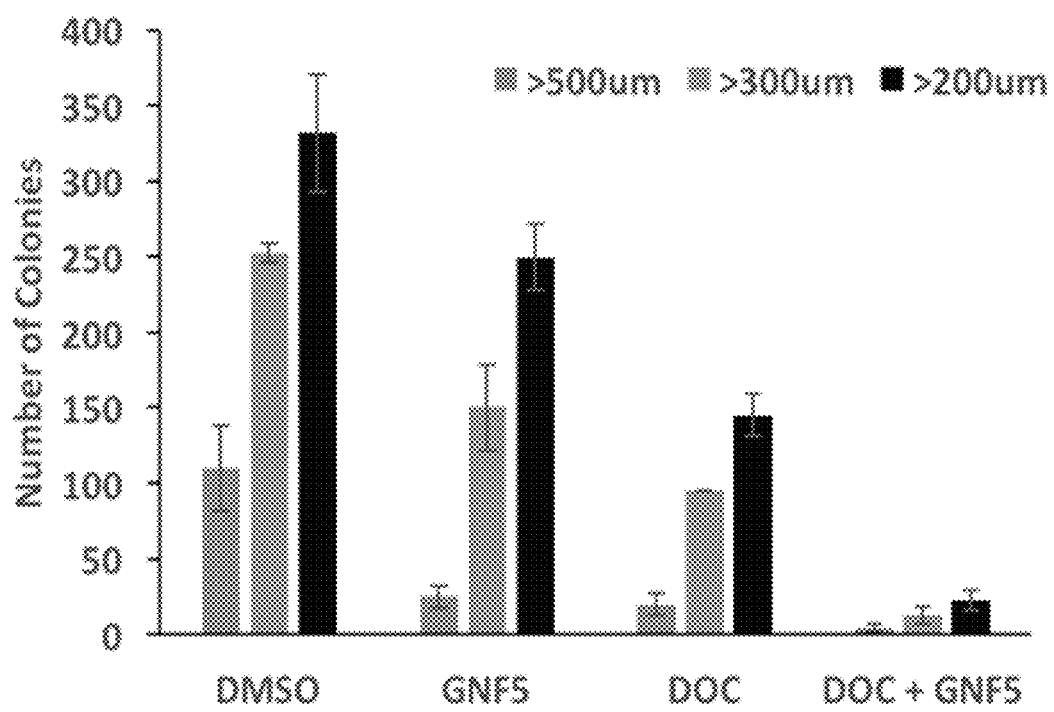

Example 17: Inhibition of Abl Kinases Sensitizes Primary Kras$^{G12D/+}$; p53$^{-/-}$-Mouse-Derived Organoids and Cell Lines to Treatment with Docetaxel To further evaluate the effect of Abl kinase inhibition on Kras$^{G12D/+}$; p53$^{-/-}$ driven lung tumors, the effect of Abl kinase inhibition on primary mouse tumor cell lines was evaluated. First, tumor organoid formation assays were performed. SPC (Sftpc)-CreERT2; KRAS$^{LSL-G12D}$; p53$^{fl/fl}$; Rosa26-tdTomato mice were given tamoxifen to induce tumor formation specifically in Type II alveolar epithelial cells through the SPC (Sftpc) driver (122). Tomato+ cells were then isolated from mice after four weeks and grown in Matrigel in the presence of primary mouse fibroblasts (GFP+) to evaluate tumor organoid formation (FIG. 28A). Organoids were treated with vehicle control, GNF5 alone, docetaxel alone, or combination therapy starting three days after plating the cells, and after the organoids were grown for two weeks, a decrease in the size of double-treated organoids compared to vehicle or single-treated organoids was observed (FIG. 28B). By comparison, no decrease in size of primary lung alveolospheres isolated from SPC (Sftpc)-CreERT2; Rosa26-tdTomato mice, expressing wild-type KRAS and p53, treated with both GNF5 and docetaxel was observed. These data are consistent with the findings in vivo showing that Abl kinase inhibition sensitizes primary lung tumors to treatment with docetaxel (FIG. 26C).

Figure 29:
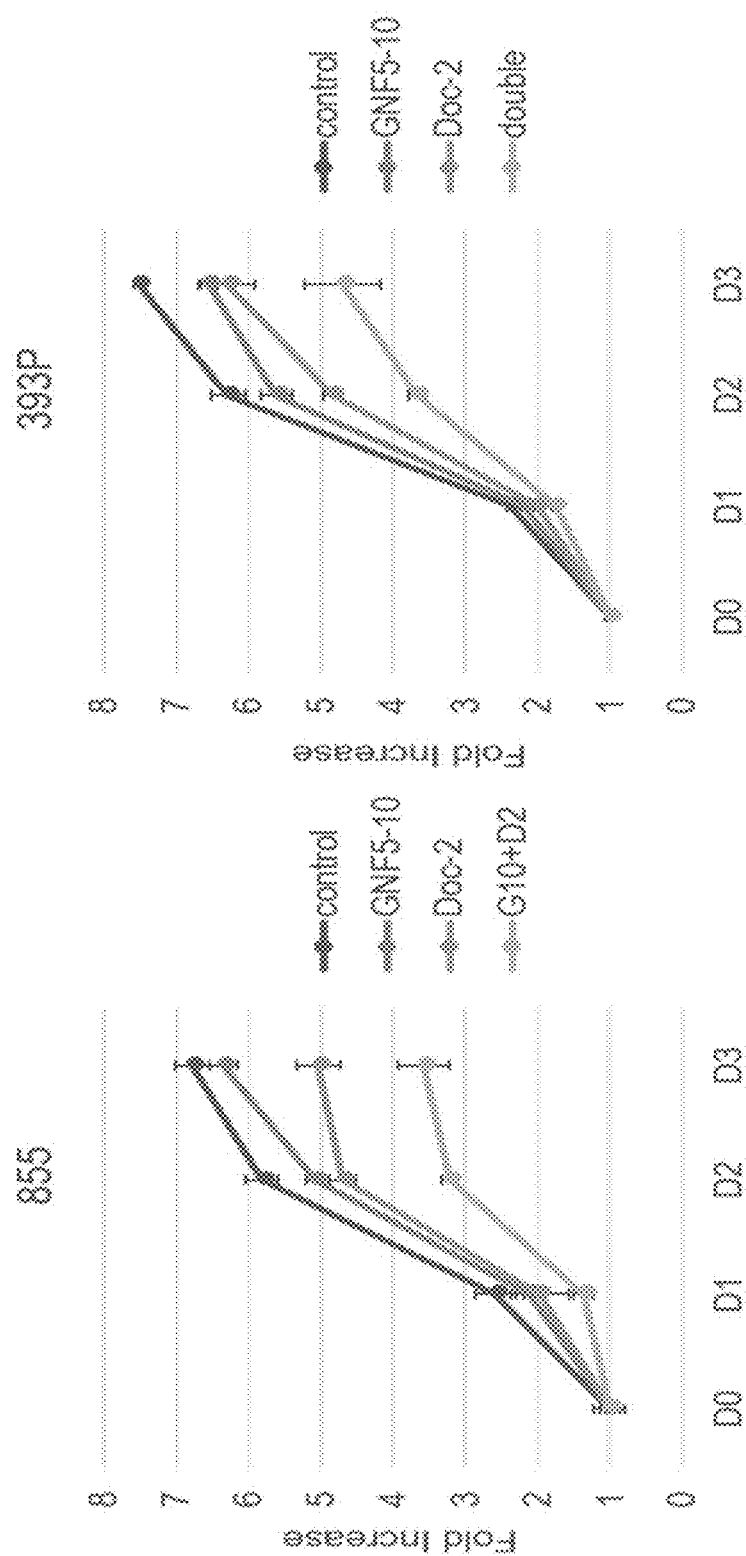
FIG. 29 is graphs showing treatment of two primary lung adenocarcinoma cell lines derived from $KRAS^{G12D+/-}$; $p53^{-/-}$ lung tumors with a combination of GNF5 (10 μM) and docetaxel (2 nM), resulted in a significant decrease in cell growth compared to treatment with either drug alone. CellTiter Glo was performed 24, 48, and 72 hours after plating.

CellTiter-Glo experiments were also performed in primary cell lines derived from Kras$^{G12D/+}$; p53$^{-/-}$ driven mouse lung tumors and found significantly reduced cell growth in the combination treatment group compared to treatment with GNF5 or docetaxel alone (FIG. 29).

Example 18: Inhibition of Abl Kinases Sensitizes Primary Kras$^{G12D/+}$; p53$^{-/-}$ Mouse Adenocarcinomas to Treatment with Docetaxel by Promoting Cell Differentiation To further define the mechanisms by which Abl kinase inhibition sensitizes Kras$^{G12D/+}$; p53$^{-/-}$ driven mouse lung tumors to docetaxel treatment, mRNA and protein expression of a variety of differentiation markers in tumor cells following treatment with the Abl kinase inhibitor, GNF5, with and without docetaxel were evaluated. Given that one of the defining characteristics of adenocarcinomas is their progressive de-differentiation from low grade, glandular structures with well-differentiated tumor cells to high grade tumors that lack any defined tissue morphology with poorly-differentiated tumor cells, it was hypothesized that Abl kinase inhibition may inhibit the natural progression of tumor de-differentiation or actively reverse it based on the data presented in Examples 1-14.

Figure 30A:
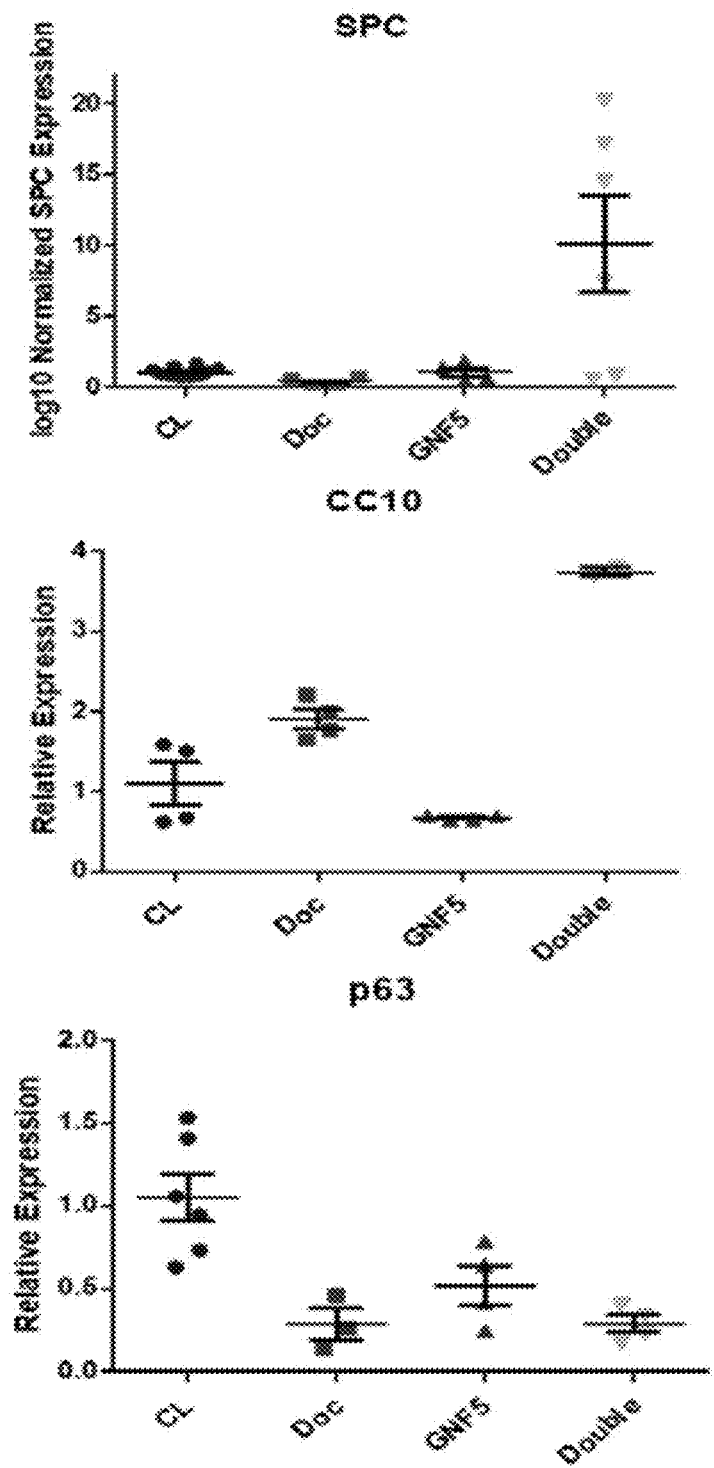
FIGS. 30A-30B show combination treatment of GNF5 and docetaxel induces lung tumor cell differentiation in vivo.
Figure 30B:
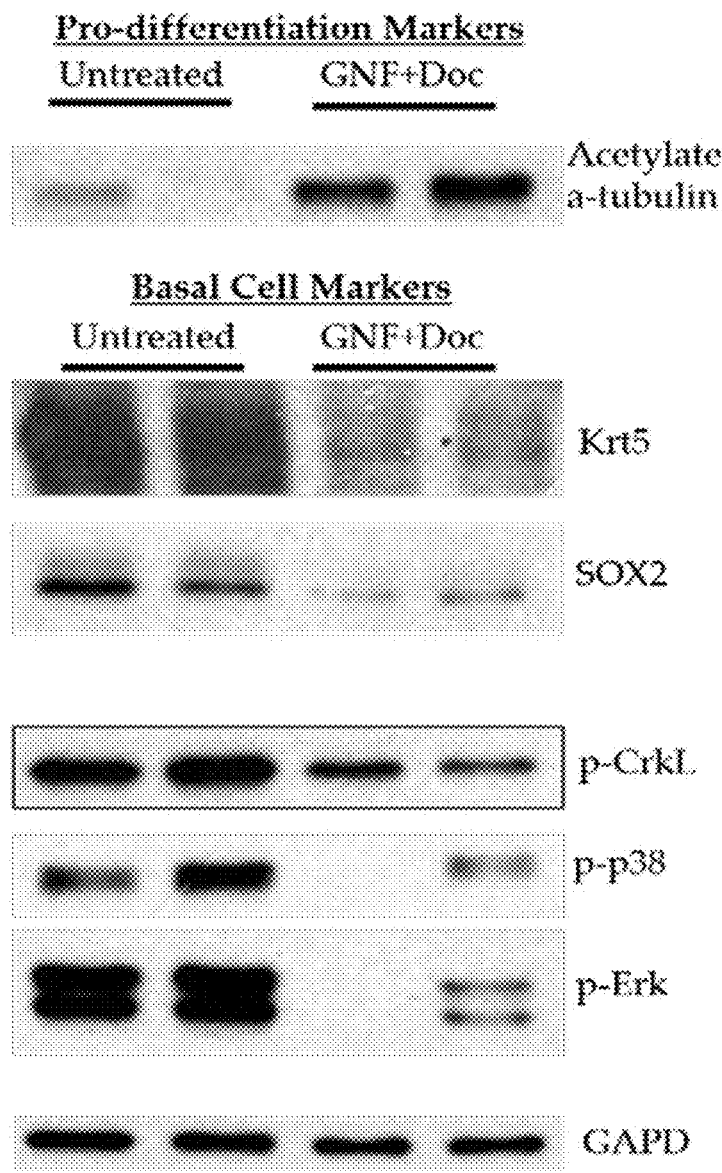

First, the expression of differentiation genes in vivo. KRAS$^{LSL-G12D}$; p53$^{fl/fl}$ mice were crossed with mice expressing the Rosa26-GFP reporter allowing for isolation of GFP+ tumor cells was evaluated by FACS. GFP+ cells were isolated from KRAS$^{LSL-G12D}$; p53$^{fl/fl}$; Rosa26-fGFP mice two weeks after treatment with vehicle, docetaxel, GNF5, or combination treatment and 10 weeks after induction of tumors with adenovirus. RT-qPCR of isolated GFP+ cells showed a significant increase in expression of terminal differentiation markers (SPC: Type II cell marker and CC10: secretory cell marker) with a concomitant decrease in expression of basal stem-cell markers (p63) (FIG. 30A). A corresponding change in protein expression of differentiation and basal markers by Western blotting of control and GNF5-treated mice was also found. Western blot analysis showed an increase in expression of the ciliated cell marker, acetylated α-tubulin, with a corresponding decrease in expression of the basal cell markers, keratin 5 and SOX2, in mice treated with docetaxel and GNF5. A decrease in phospho-p38/MAPK and phospho-ERK, signaling targets in the MAPK pathway, was also observed in mice treated with the combination therapy. (FIG. 30B).

Figure 31:
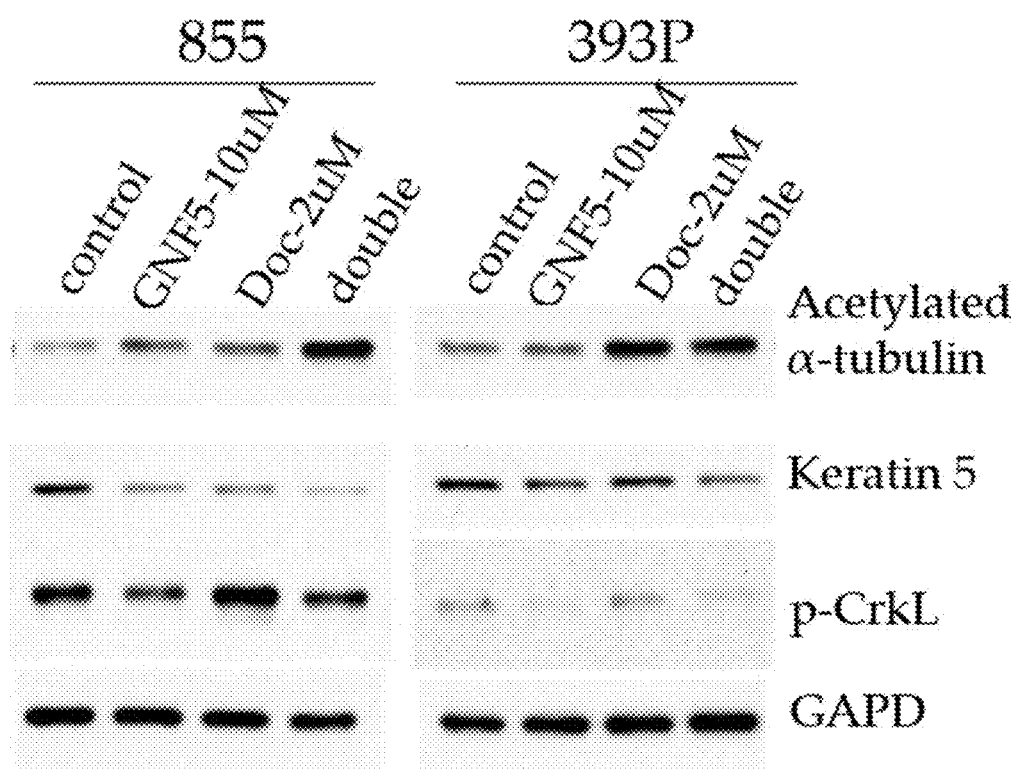
FIG. 31 is Western blots showing an increase in expression of the ciliated cell marker, acetylated α-tubulin, with a corresponding decrease in expression of the basal cell marker, keratin 5, in mice treated with docetaxel and GNF5. Phospho-CrkL is shown as a surrogate marker for Abl kinase activity along with the loading control, GAPD.

The expression of differentiation markers in vitro in primary cells isolated from KRAS$^{LSL-G12D}$; p53$^{fl/fl}$ mouse tumors was also evaluated. Primary mouse lung adenocarcinoma cell lines derived from KRAS$^{G12D+/-}$; p53$^{-/-}$ tumors were treated with vehicle control, GNF5, docetaxel, or combination treatment for 48 hours. Western blot analysis of lysate showed an increase in expression of the ciliated cell marker, acetylated α-tubulin, with a corresponding decrease in expression of the basal cell marker, keratin 5, in mice treated with docetaxel and GNF5. Consistent with the findings in vivo, an increase in expression of terminally differentiated cell markers and a decrease in expression of basal cell markers in mice treated with the combination therapy of GNF5 and docetaxel compared to vehicle control or single-agent treatment was observed (FIG. 31).

Discussion

Chemotherapy is a first-line treatment in the majority of patients with lung adenocarcinomas. Thus, combination therapies that sensitize tumors to chemotherapy would have a profound impact in the treatment of these patients. Here it was shown in the context of the autochthonous KRAS$^{LSL\text{-}G12D}$; p53$^{fl/fl}$ mouse model that Abl kinase inhibition sensitizes primary lung adenocarcinomas to treatment with docetaxel so that even sub-therapeutic doses of docetaxel confer reduced cell growth and increased cell death both in vivo and in vitro in the presence of the Abl allosteric inhibitors. Sensitization to sub-therapeutic doses of chemotherapy would significantly decrease the deleterious side effects of chemotherapy and enhance response rates in patients with lung adenocarcinomas.

Given the findings described in Examples 1-14 showing that Abl kinase inhibition promotes differentiation of lung epithelial cells, it was investigated whether Abl kinase inhibition promotes differentiation of primary lung cancer cells. Tumors frequently co-opt pathways, such as the Hippo pathway, important in development and regeneration to promote cell growth and inhibit cell death. As adenocarcinomas progress from less aggressive, well-differentiated tumors with glandular morphology reflecting their cell of origin (low grade tumors) to aggressive, poorly-differentiated tumors that lack any identifiable morphology (high grade tumors), they undergo a de-differentiation process that includes reduced expression of markers characteristic of their cell of origin and increased expression of basal cell markers or other ectopic protein expression markers. Some lung tumors even lose their epithelial morphology through an epithelial-mesenchymal transition.

The findings described herein support that inhibition of the Abl kinases promotes differentiation of lung adenocarcinomas from more de-differentiated, basal-like tumors to differentiated tumors expressing terminal cell differentiation markers such as SPC. It was found in the context of an autochthonous lung cancer mouse model, 3D lung cancer organoids, and even in primary 2D cell culture an increased expression of pro-differentiation markers and a decreased expression of basal cell markers in cells treated with the Abl kinase inhibitor, GNF5, compared to vehicle control treated mice.

In summary, Abl kinase inhibition can be a therapeutic strategy in lung pathologies, including infection and tumorigenesis. Abl kinase inhibition is fundamentally associated with epithelial cell differentiation, which is modulated in many disease states.

Any patents or publications mentioned in this specification are indicative of the levels of those skilled in the art to which the disclosure pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure is presently representative of embodiments, are exemplary, and are not intended as limitations on the scope of the invention. Changes therein and other uses will occur to those skilled in the art which are encompassed within the spirit of the disclosure as defined by the scope of the claims.

We claim:

1. A method of treating a non-small cell lung cancer in a subject in need thereof, comprising administering to the subject a therapeutically effective amount of an Abl kinase inhibitor in combination with a chemotherapeutic agent.

2. The method of claim 1, wherein the non-small cell lung cancer is a lung adenocarcinoma.

3. The method of claim 2, wherein the chemotherapeutic agent is cisplatin, carboplatin, docetaxel, gemcitabine, paclitaxel, vinorelbine, and pemetrexed, or any combination thereof.

4. The method of claim 3, wherein the chemotherapeutic agent is docetaxel or cisplatin.

5. A method of sensitizing a subject suffering from a non-small cell lung cancer to a chemotherapeutic agent comprising administering to the subject a therapeutically effective amount of an Abl kinase inhibitor, wherein the Abl kinase inhibitor is administered before, after or at the same time as the chemotherapeutic agent.

6. The method of claim 5, wherein the non-small cell lung cancer is a lung adenocarcinoma.

7. The method of claim 6, wherein the chemotherapeutic agent is cisplatin, carboplatin, docetaxel, gemcitabine, paclitaxel, vinorelbine, and pemetrexed, or any combination thereof.

8. The method of claim 7, wherein the chemotherapeutic agent is docetaxel or cisplatin.

9. The method of claim 1, wherein the Abl kinase inhibitor is selected from the group consisting of imatinib, nilotinib, dasatinib (BMS-354825), bosutinib (SKI-606), Ponatinib (AP24534), Bafetinib (INNO-406), GNF2, GNF5, ABL001, HG-7-85-01, Tozasertib (MK-0457, VX-680), Danusertib (PHA-739358), Rebastinib (DCC-2036), Axitinhib (AG013736), Vandetanib (ZD-6474), 1,3,4-thiadiazole derivatives, the compound having the structure

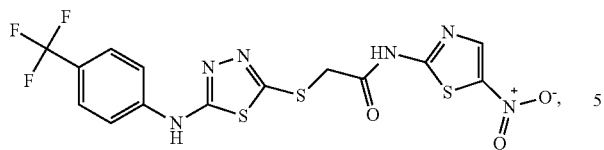

and combinations thereof.

10. The method of claim 5, wherein the Abl kinase inhibitor is selected from the group consisting of imatinib, nilotinib, dasatinib (BMS-354825), bosutinib (SKI-606), Ponatinib (AP24534), Bafetinib (INNO-406), GNF2, GNF5, ABL001, HG-7-85-01, Tozasertib (MK-0457, VX-680), Danusertib (PHA-739358), Rebastinib (DCC-2036), Axitinhib (AG013736), Vandetanib (ZD-6474), 1,3,4-thiadiazole derivatives, the compound having the structure

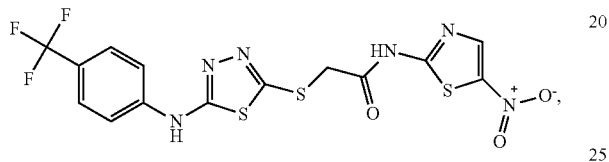

and combinations thereof.

* * * * *